US009731266B2

(12) United States Patent
Stern et al.

(10) Patent No.: US 9,731,266 B2
(45) Date of Patent: *Aug. 15, 2017

(54) LINEAR VALVE ARRAYS

(71) Applicant: IntegenX Inc., Pleasanton, CA (US)

(72) Inventors: Seth Stern, Palo Alto, CA (US); Stevan B. Jovanovich, Livermore, CA (US)

(73) Assignee: IntegenX Inc., Pleasanton, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/804,675

(22) Filed: Jul. 21, 2015

(65) Prior Publication Data

US 2016/0016140 A1    Jan. 21, 2016

Related U.S. Application Data

(63) Continuation of application No. 13/202,884, filed as application No. PCT/US2011/048528 on Aug. 20, 2011, now Pat. No. 9,121,058.

(Continued)

(51) Int. Cl.
*B01L 3/00* (2006.01)
*B01J 19/00* (2006.01)
(Continued)

(52) U.S. Cl.
CPC ..... *B01J 19/0046* (2013.01); *B01L 3/502738* (2013.01); *C12Q 1/6806* (2013.01); *C12Q 1/6869* (2013.01); *C12Q 1/6874* (2013.01); *F16K 99/0015* (2013.01); *F16K 99/0059* (2013.01); *B01J 2219/00389* (2013.01);
(Continued)

(58) Field of Classification Search
None
See application file for complete search history.

(56) References Cited

U.S. PATENT DOCUMENTS 3,075,740 A    1/1963    McIntosh
3,190,310 A    6/1965    Honsinger
(Continued)

FOREIGN PATENT DOCUMENTS

CA    2433145 A1    5/2002
CN    1109597 A     10/1995
(Continued)

OTHER PUBLICATIONS

Notice of allowance dated May 6, 2010 for U.S. Appl. No. 11/726,701.

(Continued)

*Primary Examiner* — Betty Forman
(74) *Attorney, Agent, or Firm* — Wilson Sonsini Goodrich & Rosati

(57) ABSTRACT

The invention provides systems, devices, methods, and kits for performing an integrated analysis. The integrated analysis can include sample processing, library construction, amplification, and sequencing. The integrated analysis can be performed within one or more modules that are fluidically connected to each other. The one or more modules can be controlled and/or automated by a computer. The integrated analysis can be performed on a tissue sample, a clinical sample, or an environmental sample. The integrated analysis system can have a compact format and return results within a designated period of time.

14 Claims, 18 Drawing Sheets

Related U.S. Application Data

(60) Provisional application No. 61/375,758, filed on Aug. 20, 2010, provisional application No. 61/375,791, filed on Aug. 20, 2010.

(51) Int. Cl.
   *F16K 99/00* (2006.01)
   *C12Q 1/68* (2006.01)
   *B01L 7/00* (2006.01)

(52) U.S. Cl.
   CPC ........... *B01J 2219/00599* (2013.01); *B01J 2219/00716* (2013.01); *B01J 2219/00722* (2013.01); *B01L 7/52* (2013.01); *B01L 2200/0647* (2013.01); *B01L 2200/10* (2013.01); *B01L 2200/16* (2013.01); *B01L 2300/087* (2013.01); *B01L 2300/0816* (2013.01); *B01L 2300/0867* (2013.01); *B01L 2400/043* (2013.01); *B01L 2400/0481* (2013.01); *B01L 2400/0655* (2013.01); *F16K 2099/0084* (2013.01)

(56) References Cited

U.S. PATENT DOCUMENTS

| | | |
|---|---|---|
| 3,352,643 A | 11/1967 | Ando et al. |
| 3,433,257 A | 3/1969 | Donald |
| 3,568,692 A | 3/1971 | Metzger et al. |
| 3,610,274 A | 10/1971 | Levesque et al. |
| 3,662,517 A | 5/1972 | Tascher et al. |
| 4,011,357 A | 3/1977 | Haase |
| 4,113,665 A | 9/1978 | Law et al. |
| 4,390,307 A | 6/1983 | Rice |
| 4,558,845 A | 12/1985 | Hunkapiller |
| 4,703,913 A | 11/1987 | Hunkapiller |
| 4,847,120 A | 7/1989 | Gent |
| 4,963,498 A | 10/1990 | Hillman et al. |
| 5,085,757 A | 2/1992 | Karger et al. |
| 5,275,645 A | 1/1994 | Ternoir et al. |
| 5,338,427 A | 8/1994 | Shartle et al. |
| 5,364,759 A | 11/1994 | Caskey et al. |
| 5,376,252 A | 12/1994 | Ekstrom et al. |
| 5,387,505 A | 2/1995 | Wu |
| 5,453,163 A | 9/1995 | Yan |
| 5,482,836 A | 1/1996 | Cantor et al. |
| 5,523,231 A | 6/1996 | Reeve |
| 5,571,410 A | 11/1996 | Swedberg et al. |
| 5,587,128 A | 12/1996 | Wilding et al. |
| 5,589,136 A | 12/1996 | Northrup et al. |
| 5,635,358 A | 6/1997 | Wilding et al. |
| 5,639,428 A | 6/1997 | Cottingham |
| 5,675,155 A | 10/1997 | Pentoney, Jr. et al. |
| 5,681,946 A | 10/1997 | Reeve |
| 5,705,628 A | 1/1998 | Hawkins |
| 5,705,813 A | 1/1998 | Apffel et al. |
| 5,726,026 A | 3/1998 | Wilding et al. |
| 5,741,462 A | 4/1998 | Nova et al. |
| 5,750,015 A | 5/1998 | Soane et al. |
| 5,770,029 A | 6/1998 | Nelson et al. |
| 5,775,371 A | 7/1998 | Pan et al. |
| 5,776,748 A | 7/1998 | Singhvi et al. |
| 5,830,662 A | 11/1998 | Soares et al. |
| 5,842,787 A | 12/1998 | Kopf-Sill et al. |
| 5,856,174 A | 1/1999 | Lipshutz et al. |
| 5,863,502 A | 1/1999 | Southgate et al. |
| 5,872,010 A | 2/1999 | Karger et al. |
| 5,885,470 A | 3/1999 | Parce et al. |
| 5,898,071 A | 4/1999 | Hawkins |
| 5,900,130 A | 5/1999 | Benvegnu et al. |
| 5,908,552 A | 6/1999 | Dittmann et al. |
| 5,922,591 A | 7/1999 | Anderson et al. |
| 5,942,443 A | 8/1999 | Parce et al. |
| 5,948,684 A | 9/1999 | Weigl et al. |
| 5,951,262 A | 9/1999 | Hartman |
| 5,971,158 A | 10/1999 | Yager et al. |
| 5,994,064 A | 11/1999 | Staub et al. |
| 6,001,229 A | 12/1999 | Ramsey |
| 6,007,690 A | 12/1999 | Nelson et al. |
| 6,007,775 A | 12/1999 | Yager |
| 6,010,607 A | 1/2000 | Ramsey |
| 6,027,031 A | 2/2000 | Reason et al. |
| 6,048,100 A | 4/2000 | Thrall et al. |
| 6,056,860 A | 5/2000 | Amigo et al. |
| 6,073,482 A | 6/2000 | Moles |
| 6,074,827 A | 6/2000 | Nelson et al. |
| 6,103,199 A | 8/2000 | Bjornson et al. |
| 6,110,343 A | 8/2000 | Ramsey et al. |
| 6,120,184 A | 9/2000 | Laurence et al. |
| 6,136,212 A | 10/2000 | Mastrangelo et al. |
| 6,153,389 A | 11/2000 | Haarer et al. |
| 6,168,948 B1 | 1/2001 | Anderson et al. |
| 6,176,962 B1 | 1/2001 | Soane et al. |
| 6,190,616 B1 | 2/2001 | Jovanovich et al. |
| 6,197,595 B1 | 3/2001 | Anderson et al. |
| 6,207,031 B1 | 3/2001 | Adourian et al. |
| 6,235,471 B1 | 5/2001 | Knapp et al. |
| 6,238,538 B1 | 5/2001 | Parce et al. |
| 6,251,343 B1 | 6/2001 | Dubrow et al. |
| 6,280,589 B1 | 8/2001 | Manz et al. |
| 6,319,476 B1 | 11/2001 | Victor, Jr. et al. |
| 6,321,791 B1 | 11/2001 | Chow |
| 6,322,683 B1 | 11/2001 | Wolk et al. |
| 6,326,068 B1 | 12/2001 | Kong et al. |
| 6,342,142 B1 | 1/2002 | Ramsey |
| 6,348,318 B1 | 2/2002 | Valkirs |
| 6,379,929 B1 | 4/2002 | Burns et al. |
| 6,387,234 B1 | 5/2002 | Yeung et al. |
| 6,387,707 B1 | 5/2002 | Seul et al. |
| 6,391,622 B1 | 5/2002 | Knapp et al. |
| 6,403,338 B1 | 6/2002 | Knapp et al. |
| 6,408,878 B2 | 6/2002 | Unger et al. |
| 6,423,536 B1 | 7/2002 | Jovanovich et al. |
| 6,429,025 B1 | 8/2002 | Parce et al. |
| 6,432,191 B2 | 8/2002 | Schutt |
| 6,432,290 B1 | 8/2002 | Harrison et al. |
| 6,454,924 B2 | 9/2002 | Jedrzejewski et al. |
| 6,461,492 B1 | 10/2002 | Hayashizaki et al. |
| 6,489,112 B1 | 12/2002 | Hadd et al. |
| 6,521,188 B1 | 2/2003 | Webster |
| 6,524,456 B1 | 2/2003 | Ramsey et al. |
| 6,527,003 B1 | 3/2003 | Webster |
| 6,531,041 B1 | 3/2003 | Cong et al. |
| 6,531,282 B1 | 3/2003 | Dau et al. |
| 6,532,997 B1 | 3/2003 | Bedingham et al. |
| 6,533,914 B1 | 3/2003 | Liu |
| 6,534,262 B1 | 3/2003 | McKernan et al. |
| 6,537,757 B1 | 3/2003 | Langmore et al. |
| 6,544,734 B1 | 4/2003 | Briscoe et al. |
| 6,551,839 B2 | 4/2003 | Jovanovich et al. |
| 6,581,441 B1 | 6/2003 | Paul |
| 6,581,899 B2 | 6/2003 | Williams |
| 6,605,454 B2 | 8/2003 | Barenburg et al. |
| 6,613,525 B2 | 9/2003 | Nelson et al. |
| 6,614,228 B2 | 9/2003 | Hofmann et al. |
| 6,618,679 B2 | 9/2003 | Loehrlein et al. |
| 6,620,584 B1 | 9/2003 | Chee et al. |
| 6,623,613 B1 | 9/2003 | Mathies et al. |
| 6,627,446 B1 | 9/2003 | Roach et al. |
| 6,629,820 B2 | 10/2003 | Kornelsen |
| 6,632,619 B1 | 10/2003 | Harrison et al. |
| 6,632,655 B1 | 10/2003 | Mehta et al. |
| 6,660,148 B2 | 12/2003 | Shoji et al. |
| 6,663,833 B1 | 12/2003 | Stave et al. |
| 6,685,442 B2 | 2/2004 | Chinn et al. |
| 6,685,678 B2 | 2/2004 | Evans et al. |
| 6,685,809 B1 | 2/2004 | Jacobson et al. |
| 6,705,345 B1 | 3/2004 | Bifano |
| 6,740,219 B2 | 5/2004 | Imai et al. |
| 6,752,922 B2 | 6/2004 | Huang et al. |
| 6,764,648 B1 | 7/2004 | Roach et al. |
| 6,782,746 B1 | 8/2004 | Hasselbrink, Jr. et al. |
| 6,786,708 B2 | 9/2004 | Brown et al. |
| 6,787,111 B2 | 9/2004 | Roach et al. |

(56) References Cited

U.S. PATENT DOCUMENTS

| | | |
|---|---|---|
| 6,793,753 B2 | 9/2004 | Unger et al. |
| 6,802,342 B2 | 10/2004 | Fernandes et al. |
| 6,803,019 B1 | 10/2004 | Bjornson et al. |
| 6,807,490 B1 | 10/2004 | Perlin |
| 6,824,663 B1 | 11/2004 | Boone |
| 6,829,753 B2 | 12/2004 | Lee et al. |
| 6,833,246 B2 | 12/2004 | Balasubramanian |
| 6,852,287 B2 | 2/2005 | Ganesan |
| 6,870,185 B2 | 3/2005 | Roach et al. |
| 6,883,774 B2 | 4/2005 | Nielsen et al. |
| 6,885,982 B2 | 4/2005 | Harris et al. |
| 6,899,137 B2 | 5/2005 | Unger et al. |
| 6,923,907 B2 | 8/2005 | Hobbs et al. |
| 6,929,030 B2 | 8/2005 | Unger et al. |
| 6,951,632 B2 | 10/2005 | Unger et al. |
| 6,953,058 B2 | 10/2005 | Fernandes et al. |
| 6,960,437 B2 | 11/2005 | Enzelberger et al. |
| 6,994,986 B2 | 2/2006 | Swartz et al. |
| 7,005,052 B2 | 2/2006 | Shimizu et al. |
| 7,005,292 B2 | 2/2006 | Wilding et al. |
| 7,005,493 B2 | 2/2006 | Huang et al. |
| 7,015,030 B1 | 3/2006 | Fouillet et al. |
| 7,046,357 B2 | 5/2006 | Weinberger et al. |
| 7,049,558 B2 | 5/2006 | Baer et al. |
| 7,063,304 B2 | 6/2006 | Leys |
| 7,081,191 B2 | 7/2006 | Shoji et al. |
| 7,087,380 B2 | 8/2006 | Griffiths et al. |
| 7,097,809 B2 | 8/2006 | Van Dam et al. |
| 7,105,300 B2 | 9/2006 | Parce et al. |
| 7,118,910 B2 | 10/2006 | Unger et al. |
| 7,142,987 B2 | 11/2006 | Eggers |
| 7,157,228 B2 | 1/2007 | Hashmi et al. |
| 7,169,557 B2 | 1/2007 | Rosenblum et al. |
| 7,170,050 B2 | 1/2007 | Turner et al. |
| 7,198,759 B2 | 4/2007 | Bryning et al. |
| 7,211,388 B2 | 5/2007 | Cash et al |
| 7,217,367 B2 | 5/2007 | Huang et al. |
| 7,232,656 B2 | 6/2007 | Balasubramanian et al. |
| 7,244,559 B2 | 7/2007 | Rothberg et al. |
| 7,244,567 B2 | 7/2007 | Chen et al. |
| 7,244,961 B2 | 7/2007 | Jovanovich et al. |
| 7,258,744 B2 | 8/2007 | Sakurada et al. |
| 7,258,774 B2 | 8/2007 | Chou et al. |
| 7,279,146 B2 | 10/2007 | Nassef et al. |
| 7,282,361 B2 | 10/2007 | Hodge |
| 7,312,085 B2 | 12/2007 | Chou et al. |
| 7,312,611 B1 | 12/2007 | Harrison et al. |
| 7,323,305 B2 | 1/2008 | Leamon et al. |
| 7,329,388 B2 | 2/2008 | Guzman |
| 7,361,471 B2 | 4/2008 | Gerdes et al. |
| 7,377,483 B2 | 5/2008 | Iwabuchi et al. |
| 7,416,165 B2 | 8/2008 | Ohmi et al. |
| 7,419,578 B2 | 9/2008 | Sakai et al. |
| 7,438,856 B2 | 10/2008 | Jedrzejewski et al. |
| 7,445,926 B2 | 11/2008 | Mathies et al. |
| 7,473,342 B2 | 1/2009 | Ugai et al. |
| 7,486,865 B2 | 2/2009 | Foquet et al. |
| 7,488,603 B2 | 2/2009 | Gjerde et al. |
| 7,501,237 B2 | 3/2009 | Solus et al. |
| 7,526,741 B2 | 4/2009 | Lee et al. |
| 7,531,076 B2 | 5/2009 | Hayashizaki et al. |
| 7,537,886 B1 | 5/2009 | Nazarenko et al. |
| 7,575,865 B2 | 8/2009 | Leamon et al. |
| 7,584,240 B2 | 9/2009 | Eggers |
| 7,589,184 B2 | 9/2009 | Hogan et al. |
| 7,645,580 B2 | 1/2010 | Barber et al. |
| 7,691,614 B2 | 4/2010 | Senapathy |
| 7,704,735 B2 | 4/2010 | Facer et al. |
| 7,718,442 B2 | 5/2010 | Davis et al. |
| 7,744,737 B1 | 6/2010 | James et al. |
| 7,745,207 B2 | 6/2010 | Jovanovich et al. |
| 7,749,365 B2 | 7/2010 | Nguyen et al. |
| 7,749,737 B2 | 7/2010 | McBride et al. |
| 7,763,453 B2 | 7/2010 | Clemmens et al. |
| 7,766,033 B2 | 8/2010 | Mathies et al. |
| 7,785,458 B2 | 8/2010 | Shimizu et al. |
| 7,790,368 B1 | 9/2010 | Fukuzono |
| 7,799,553 B2 | 9/2010 | Mathies et al. |
| 7,803,281 B2 | 9/2010 | Davies |
| 7,817,273 B2 | 10/2010 | Bahatt et al. |
| 7,832,429 B2 | 11/2010 | Young et al. |
| 7,863,357 B2 | 1/2011 | Madabhushi et al. |
| 7,867,713 B2 | 1/2011 | Nasarabadi |
| 7,885,770 B2 | 2/2011 | Gill et al. |
| 7,892,856 B2 | 2/2011 | Grate et al. |
| 7,942,160 B2 | 5/2011 | Jeon et al. |
| 7,943,305 B2 | 5/2011 | Korlach et al. |
| 7,959,875 B2 | 6/2011 | Zhou et al. |
| 7,972,561 B2 | 7/2011 | Viovy et al. |
| 7,976,789 B2 | 7/2011 | Kenis et al. |
| 7,976,795 B2 | 7/2011 | Zhou et al. |
| 7,998,708 B2 | 8/2011 | Handique et al. |
| 8,007,746 B2 | 8/2011 | Unger et al. |
| 8,018,593 B2 | 9/2011 | Tan et al. |
| 8,037,903 B2 | 10/2011 | Wang et al. |
| 8,053,192 B2 | 11/2011 | Bignell et al. |
| RE43,122 E | 1/2012 | Harrison et al. |
| 8,142,635 B2 | 3/2012 | Shimizu et al. |
| 8,221,990 B2 | 7/2012 | Mori et al. |
| 8,222,023 B2 | 7/2012 | Battrell et al. |
| 8,268,263 B2 | 9/2012 | Campbell et al. |
| 8,283,165 B2 | 10/2012 | Hogan et al. |
| 8,313,941 B2 | 11/2012 | Takayama et al. |
| 8,337,777 B2 | 12/2012 | Nurse et al. |
| 8,388,908 B2 | 3/2013 | Blaga et al. |
| 8,394,642 B2 | 3/2013 | Jovanovich et al. |
| 8,398,642 B2 | 3/2013 | Weekes |
| 8,420,318 B2 | 4/2013 | Mathies et al. |
| 8,431,340 B2 | 4/2013 | Jovanovich et al. |
| 8,431,384 B2 | 4/2013 | Hogan et al. |
| 8,431,390 B2 | 4/2013 | Jovanovich et al. |
| 8,476,063 B2 | 7/2013 | Jovanovich et al. |
| 8,501,305 B2 | 8/2013 | Barlow |
| 8,512,538 B2 | 8/2013 | Majlof et al. |
| 8,551,714 B2 | 10/2013 | Jovanovich et al. |
| 8,557,518 B2 | 10/2013 | Jovanovich et al. |
| 8,562,918 B2 | 10/2013 | Jovanovich et al. |
| 8,584,703 B2 | 11/2013 | Kobrin et al. |
| 8,672,532 B2 | 3/2014 | Jovanovich et al. |
| 8,748,165 B2 | 6/2014 | Vangbo et al. |
| 8,763,642 B2 | 7/2014 | Vangbo |
| 8,841,116 B2 | 9/2014 | Mathies et al. |
| 8,894,946 B2 | 11/2014 | Nielsen et al. |
| 9,012,236 B2 | 4/2015 | Jovanovich et al. |
| 9,121,058 B2 | 9/2015 | Stern et al. |
| 9,341,284 B2 | 5/2016 | Vangbo |
| 9,592,501 B2 | 3/2017 | Jarvius et al. |
| 9,663,819 B2 | 5/2017 | Jovanovich et al. |
| 2001/0012612 A1 | 8/2001 | Petersen et al. |
| 2001/0041357 A1 | 11/2001 | Fouillet et al. |
| 2002/0003895 A1 | 1/2002 | Some |
| 2002/0022261 A1 | 2/2002 | Anderson et al. |
| 2002/0022587 A1 | 2/2002 | Ferguson et al. |
| 2002/0025529 A1 | 2/2002 | Quake et al. |
| 2002/0025576 A1 | 2/2002 | Northrup et al. |
| 2002/0042125 A1 | 4/2002 | Petersen et al. |
| 2002/0047003 A1 | 4/2002 | Bedingham et al. |
| 2002/0048536 A1 | 4/2002 | Bergh et al. |
| 2002/0051992 A1 | 5/2002 | Bridgham et al. |
| 2002/0055167 A1 | 5/2002 | Pourahmadi et al. |
| 2002/0058332 A1 | 5/2002 | Quake et al. |
| 2002/0068357 A1 | 6/2002 | Mathies et al. |
| 2002/0098097 A1 | 7/2002 | Singh |
| 2002/0110900 A1 | 8/2002 | Jovanovich et al. |
| 2002/0115201 A1 | 8/2002 | Barenburg et al. |
| 2002/0119480 A1 | 8/2002 | Weir et al. |
| 2002/0119482 A1 | 8/2002 | Nelson et al. |
| 2002/0127736 A1 | 9/2002 | Chou et al. |
| 2002/0137039 A1 | 9/2002 | Gessner |
| 2002/0139084 A1 | 10/2002 | Tobolka |
| 2002/0144738 A1 | 10/2002 | Unger et al. |
| 2002/0148992 A1 | 10/2002 | Hayenga et al. |
| 2002/0151089 A1 | 10/2002 | Chapman et al. |
| 2002/0157951 A1 | 10/2002 | Foret et al. |

(56) References Cited

U.S. PATENT DOCUMENTS

| | | |
|---|---|---|
| 2002/0160361 A1 | 10/2002 | Loehrlein et al. |
| 2002/0187560 A1 | 12/2002 | Pezzuto et al. |
| 2003/0008308 A1 | 1/2003 | Enzelberger et al. |
| 2003/0019753 A1 | 1/2003 | Ogle et al. |
| 2003/0021734 A1 | 1/2003 | Vann et al. |
| 2003/0029724 A1 | 2/2003 | Derand et al. |
| 2003/0070677 A1 | 4/2003 | Handique et al. |
| 2003/0077839 A1 | 4/2003 | Takei |
| 2003/0087425 A1 | 5/2003 | Eggers |
| 2003/0087446 A1 | 5/2003 | Eggers |
| 2003/0087455 A1 | 5/2003 | Eggers et al. |
| 2003/0088657 A1 | 5/2003 | Eggers |
| 2003/0095897 A1 | 5/2003 | Grate et al. |
| 2003/0104466 A1 | 6/2003 | Knapp et al. |
| 2003/0129755 A1 | 7/2003 | Sadler et al. |
| 2003/0162304 A1 | 8/2003 | Dority et al. |
| 2003/0175706 A1 | 9/2003 | Zhang |
| 2003/0197139 A1 | 10/2003 | Williams |
| 2003/0198573 A1 | 10/2003 | Forood et al. |
| 2003/0215369 A1 | 11/2003 | Eggers et al. |
| 2003/0217923 A1 | 11/2003 | Harrison et al. |
| 2004/0003997 A1 | 1/2004 | Anazawa et al. |
| 2004/0008687 A1 | 1/2004 | Matsubara |
| 2004/0013536 A1 | 1/2004 | Hower et al. |
| 2004/0014091 A1 | 1/2004 | Duck et al. |
| 2004/0018611 A1 | 1/2004 | Ward et al. |
| 2004/0021068 A1 | 2/2004 | Staats |
| 2004/0022676 A1 | 2/2004 | Hamilton et al. |
| 2004/0037739 A1 | 2/2004 | McNeely et al. |
| 2004/0038385 A1 | 2/2004 | Langlois et al. |
| 2004/0053290 A1 | 3/2004 | Terbrueggen et al. |
| 2004/0063217 A1 | 4/2004 | Webster et al. |
| 2004/0072278 A1 | 4/2004 | Chou et al. |
| 2004/0086427 A1 | 5/2004 | Childers et al. |
| 2004/0086870 A1 | 5/2004 | Tyvoll et al. |
| 2004/0086872 A1 | 5/2004 | Childers et al. |
| 2004/0101966 A1 | 5/2004 | Davis et al. |
| 2004/0132170 A1 | 7/2004 | Storek et al. |
| 2004/0146452 A1 | 7/2004 | Fujieda et al. |
| 2004/0151629 A1 | 8/2004 | Pease et al. |
| 2004/0185484 A1 | 9/2004 | Costa et al. |
| 2004/0197845 A1 | 10/2004 | Hassibi et al. |
| 2004/0200724 A1 | 10/2004 | Fujii et al. |
| 2004/0209354 A1 | 10/2004 | Mathies et al. |
| 2004/0217004 A1 | 11/2004 | Hayashizaki et al. |
| 2004/0219533 A1 | 11/2004 | Davis et al. |
| 2004/0224380 A1 | 11/2004 | Chou et al. |
| 2005/0026181 A1 | 2/2005 | Davis et al. |
| 2005/0026300 A1 | 2/2005 | Samper et al. |
| 2005/0042656 A1 | 2/2005 | Davis et al. |
| 2005/0047967 A1 | 3/2005 | Chuang et al. |
| 2005/0053952 A1 | 3/2005 | Hong et al. |
| 2005/0142663 A1 | 6/2005 | Parthasarathy et al. |
| 2005/0161326 A1 | 7/2005 | Morita et al. |
| 2005/0161669 A1 | 7/2005 | Jovanovich et al. |
| 2005/0181394 A1 | 8/2005 | Steemers et al. |
| 2005/0201901 A1 | 9/2005 | Grossman et al. |
| 2005/0221373 A1 | 10/2005 | Enzelberger et al. |
| 2005/0224134 A1 | 10/2005 | Yin et al. |
| 2005/0224352 A1 | 10/2005 | Harrison et al. |
| 2005/0241941 A1 | 11/2005 | Parce et al. |
| 2005/0250199 A1 | 11/2005 | Anderson et al. |
| 2005/0255000 A1 | 11/2005 | Yamamoto et al. |
| 2005/0255003 A1 | 11/2005 | Summersgill et al. |
| 2005/0255007 A1 | 11/2005 | Yamada et al. |
| 2005/0266582 A1 | 12/2005 | Modlin et al. |
| 2005/0287572 A1 | 12/2005 | Mathies et al. |
| 2006/0014177 A1 | 1/2006 | Hogan et al. |
| 2006/0027456 A1 | 2/2006 | Harrison et al. |
| 2006/0040300 A1 | 2/2006 | Dapprich et al. |
| 2006/0057209 A1 | 3/2006 | Chapman et al. |
| 2006/0073484 A1 | 4/2006 | Mathies et al. |
| 2006/0076068 A1 | 4/2006 | Young et al. |
| 2006/0140051 A1 | 6/2006 | Kim et al. |
| 2006/0163143 A1 | 7/2006 | Chirica et al. |
| 2006/0177832 A1 | 8/2006 | Brenner |
| 2006/0186043 A1 | 8/2006 | Covey et al. |
| 2006/0210994 A1 | 9/2006 | Joyce |
| 2006/0210998 A1 | 9/2006 | Kettlitz et al. |
| 2006/0260941 A1 | 11/2006 | Tan et al. |
| 2006/0263789 A1 | 11/2006 | Kincaid |
| 2006/0266645 A1 | 11/2006 | Chen et al. |
| 2006/0292032 A1 | 12/2006 | Hataoka et al. |
| 2007/0015179 A1 | 1/2007 | Klapperich et al. |
| 2007/0017812 A1 | 1/2007 | Bousse |
| 2007/0020654 A1 | 1/2007 | Blume et al. |
| 2007/0031865 A1 | 2/2007 | Willoughby |
| 2007/0034025 A1 | 2/2007 | Pant et al. |
| 2007/0105163 A1 | 5/2007 | Grate et al. |
| 2007/0113908 A1 | 5/2007 | Lee et al. |
| 2007/0122819 A1 | 5/2007 | Wu et al. |
| 2007/0175756 A1 | 8/2007 | Nguyen et al. |
| 2007/0183935 A1 | 8/2007 | Clemmens et al. |
| 2007/0184463 A1 | 8/2007 | Molho et al. |
| 2007/0184547 A1 | 8/2007 | Handique et al. |
| 2007/0202531 A1 | 8/2007 | Grover et al. |
| 2007/0218485 A1 | 9/2007 | Davis et al. |
| 2007/0237686 A1 | 10/2007 | Mathies et al. |
| 2007/0238109 A1 | 10/2007 | Min et al. |
| 2007/0248958 A1 | 10/2007 | Jovanovich et al. |
| 2007/0263049 A1 | 11/2007 | Preckel et al. |
| 2007/0289941 A1 | 12/2007 | Davies et al. |
| 2007/0292941 A1 | 12/2007 | Handique et al. |
| 2007/0297947 A1 | 12/2007 | Sommers et al. |
| 2008/0014576 A1 | 1/2008 | Jovanovich et al. |
| 2008/0014589 A1 | 1/2008 | Link et al. |
| 2008/0047836 A1 | 2/2008 | Strand et al. |
| 2008/0064610 A1 | 3/2008 | Lipovsek et al. |
| 2008/0124723 A1 | 5/2008 | Dale et al. |
| 2008/0131904 A1 | 6/2008 | Parce et al. |
| 2008/0138809 A1 | 6/2008 | Kapur et al. |
| 2008/0160630 A1 | 7/2008 | Liu et al. |
| 2008/0164155 A1 | 7/2008 | Pease et al. |
| 2008/0179255 A1 | 7/2008 | Jung et al. |
| 2008/0179555 A1 | 7/2008 | Landers et al. |
| 2008/0217178 A1 | 9/2008 | Ben-Asouli et al. |
| 2008/0237146 A1 | 10/2008 | Harrison et al. |
| 2008/0241844 A1 | 10/2008 | Kellogg |
| 2008/0242560 A1 | 10/2008 | Gunderson et al. |
| 2008/0257437 A1 | 10/2008 | Fernandes et al. |
| 2008/0262747 A1 | 10/2008 | Kain et al. |
| 2008/0281090 A1 | 11/2008 | Lee et al. |
| 2008/0302732 A1 | 12/2008 | Soh et al. |
| 2008/0311585 A1 | 12/2008 | Gao et al. |
| 2009/0004494 A1 | 1/2009 | Blenke et al. |
| 2009/0011959 A1 | 1/2009 | Costa et al. |
| 2009/0020427 A1 | 1/2009 | Tan et al. |
| 2009/0023603 A1 | 1/2009 | Selden et al. |
| 2009/0026082 A1 | 1/2009 | Rothberg et al. |
| 2009/0035770 A1 | 2/2009 | Mathies et al. |
| 2009/0053799 A1 | 2/2009 | Chang-Yen et al. |
| 2009/0056822 A1 | 3/2009 | Young et al. |
| 2009/0060797 A1 | 3/2009 | Mathies et al. |
| 2009/0084679 A1 | 4/2009 | Harrison et al. |
| 2009/0087850 A1 | 4/2009 | Eid et al. |
| 2009/0092970 A1 | 4/2009 | Williams et al. |
| 2009/0134069 A1 | 5/2009 | Handique |
| 2009/0137413 A1 | 5/2009 | Mehta et al. |
| 2009/0148933 A1 | 6/2009 | Battrell et al. |
| 2009/0178934 A1 | 7/2009 | Jarvius et al. |
| 2009/0181411 A1 | 7/2009 | Battrell et al. |
| 2009/0183990 A1 | 7/2009 | Shoji et al. |
| 2009/0233325 A1 | 9/2009 | Mori et al. |
| 2009/0253181 A1 | 10/2009 | Vangbo et al. |
| 2009/0269504 A1 | 10/2009 | Liao |
| 2009/0286327 A1 | 11/2009 | Cho et al. |
| 2009/0311804 A1 | 12/2009 | Mcbrady et al. |
| 2009/0314970 A1 | 12/2009 | McAvoy et al. |
| 2009/0314972 A1 | 12/2009 | Mcavoy et al. |
| 2009/0325183 A1 | 12/2009 | Lao et al. |
| 2009/0325276 A1 | 12/2009 | Battrell et al. |
| 2009/0325277 A1 | 12/2009 | Shigeura et al. |
| 2010/0010472 A1 | 1/2010 | Moore |
| 2010/0035252 A1 | 2/2010 | Rothberg et al. |

(56) References Cited

U.S. PATENT DOCUMENTS

| | | |
|---|---|---|
| 2010/0068723 A1 | 3/2010 | Jovanovich et al. |
| 2010/0075858 A1 | 3/2010 | Davis et al. |
| 2010/0092948 A1 | 4/2010 | Davis et al. |
| 2010/0093068 A1 | 4/2010 | Williams |
| 2010/0111770 A1 | 5/2010 | Hwang et al. |
| 2010/0129810 A1 | 5/2010 | Greiner et al. |
| 2010/0137143 A1 | 6/2010 | Rothberg et al. |
| 2010/0165784 A1 | 7/2010 | Jovanovich et al. |
| 2010/0172898 A1 | 7/2010 | Doyle et al. |
| 2010/0173392 A1 | 7/2010 | Davis et al. |
| 2010/0173398 A1 | 7/2010 | Peterman |
| 2010/0178210 A1 | 7/2010 | Hogan et al. |
| 2010/0197507 A1 | 8/2010 | Rothberg et al. |
| 2010/0209957 A1 | 8/2010 | Hogan et al. |
| 2010/0210008 A1 | 8/2010 | Strand et al. |
| 2010/0218623 A1 | 9/2010 | Eggers et al. |
| 2010/0221726 A1 | 9/2010 | Zenhausern et al. |
| 2010/0224255 A1 | 9/2010 | Mathies et al. |
| 2010/0228513 A1 | 9/2010 | Roth et al. |
| 2010/0233696 A1 | 9/2010 | Joseph et al. |
| 2010/0243916 A1 | 9/2010 | Maurer et al. |
| 2010/0248363 A1 | 9/2010 | Hogan et al. |
| 2010/0252123 A1 | 10/2010 | Mathies et al. |
| 2010/0266432 A1 | 10/2010 | Pirk et al. |
| 2010/0285578 A1 | 11/2010 | Selden et al. |
| 2010/0285606 A1 | 11/2010 | Phillips et al. |
| 2010/0285975 A1 | 11/2010 | Mathies et al. |
| 2010/0291666 A1 | 11/2010 | Collier et al. |
| 2010/0303687 A1 | 12/2010 | Blaga et al. |
| 2010/0304355 A1 | 12/2010 | Shuler et al. |
| 2010/0304986 A1 | 12/2010 | Chen et al. |
| 2010/0326826 A1 | 12/2010 | Harrison et al. |
| 2011/0003301 A1 | 1/2011 | Raymond et al. |
| 2011/0005932 A1 | 1/2011 | Jovanovich et al. |
| 2011/0008785 A1 | 1/2011 | Tan et al. |
| 2011/0008813 A1 | 1/2011 | Dilleen et al. |
| 2011/0020920 A1 | 1/2011 | Mathies et al. |
| 2011/0027913 A1 | 2/2011 | Bau et al. |
| 2011/0038758 A1 | 2/2011 | Akaba et al. |
| 2011/0039303 A1 | 2/2011 | Jovanovich et al. |
| 2011/0041935 A1 | 2/2011 | Zhou et al. |
| 2011/0045505 A1 | 2/2011 | Warthoe et al. |
| 2011/0048945 A1 | 3/2011 | Harrison et al. |
| 2011/0053784 A1 | 3/2011 | Unger et al. |
| 2011/0070578 A1 | 3/2011 | Bell et al. |
| 2011/0076735 A1 | 3/2011 | Jovanovich et al. |
| 2011/0124049 A1 | 5/2011 | Li et al. |
| 2011/0126910 A1 | 6/2011 | May |
| 2011/0126911 A1 | 6/2011 | Kobrin et al. |
| 2011/0127222 A1 | 6/2011 | Chang-Yen et al. |
| 2011/0136179 A1 | 6/2011 | Bin/Lee et al. |
| 2011/0137018 A1 | 6/2011 | Chang-Yen et al. |
| 2011/0171086 A1 | 7/2011 | Prins et al. |
| 2011/0172403 A1 | 7/2011 | Harrold |
| 2011/0186466 A1 | 8/2011 | Kurowski et al. |
| 2011/0189678 A1 | 8/2011 | McBride et al. |
| 2011/0195495 A1 | 8/2011 | Selden et al. |
| 2011/0206576 A1 | 8/2011 | Woudenberg et al. |
| 2011/0207140 A1 | 8/2011 | Handique et al. |
| 2011/0212440 A1 | 9/2011 | Viovy et al. |
| 2011/0212446 A1 | 9/2011 | Wang et al. |
| 2011/0223605 A1 | 9/2011 | Bienvenue et al. |
| 2011/0229897 A1 | 9/2011 | Bell et al. |
| 2011/0229898 A1 | 9/2011 | Bell et al. |
| 2011/0256530 A1 | 10/2011 | Hogan |
| 2011/0312614 A1 | 12/2011 | Selden et al. |
| 2012/0055798 A1 | 3/2012 | Selden et al. |
| 2012/0100522 A1 | 4/2012 | Saghbini et al. |
| 2012/0181460 A1 | 7/2012 | Eberhart et al. |
| 2012/0240127 A1 | 9/2012 | Brittenham et al. |
| 2012/0267247 A1 | 10/2012 | Tan et al. |
| 2012/0279638 A1 | 11/2012 | Zhou et al. |
| 2012/0290648 A1 | 11/2012 | Sharkey |
| 2012/0308987 A1 | 12/2012 | Hogan et al. |
| 2012/0309637 A1 | 12/2012 | Schumm et al. |
| 2012/0315635 A1 | 12/2012 | Vangbo et al. |
| 2012/0322666 A1 | 12/2012 | Pham et al. |
| 2013/0029338 A1 | 1/2013 | Jovanovich et al. |
| 2013/0053255 A1 | 2/2013 | Vangbo et al. |
| 2013/0074944 A1 | 3/2013 | Van Gelder |
| 2013/0084565 A1 | 4/2013 | Landers et al. |
| 2013/0105017 A1 | 5/2013 | Zhou et al. |
| 2013/0115607 A1 | 5/2013 | Nielsen et al. |
| 2013/0139895 A1 | 6/2013 | Vangbo |
| 2013/0203634 A1 | 8/2013 | Jovanovich et al. |
| 2013/0210129 A1 | 8/2013 | Selden et al. |
| 2013/0213810 A1 | 8/2013 | Tan et al. |
| 2013/0217026 A1 | 8/2013 | Egan et al. |
| 2013/0224846 A1 | 8/2013 | Jovanovich et al. |
| 2013/0240140 A1 | 9/2013 | Kurowski et al. |
| 2013/0260380 A1 | 10/2013 | Hall et al. |
| 2013/0344475 A1 | 12/2013 | Jovanovich et al. |
| 2014/0045704 A1 | 2/2014 | Jovanovich et al. |
| 2014/0065628 A1 | 3/2014 | Van Gelder et al. |
| 2014/0065689 A1 | 3/2014 | Hogan et al. |
| 2014/0073043 A1 | 3/2014 | Holmes |
| 2014/0161686 A1 | 6/2014 | Bort et al. |
| 2014/0170645 A1 | 6/2014 | Jovanovich et al. |
| 2014/0246618 A1 | 9/2014 | Zhou et al. |
| 2014/0370519 A1 | 12/2014 | Vangbo et al. |
| 2015/0021502 A1 | 1/2015 | Vangbo |
| 2015/0024436 A1 | 1/2015 | Eberhart et al. |
| 2015/0136602 A1 | 5/2015 | Jovanovich et al. |
| 2015/0136604 A1 | 5/2015 | Nielsen et al. |
| 2016/0053314 A1 | 2/2016 | Jovanovich et al. |
| 2016/0096176 A1 | 4/2016 | Jarvius et al. |
| 2016/0116439 A1 | 4/2016 | Kindwall et al. |
| 2016/0305972 A1 | 10/2016 | Ogg et al. |
| 2016/0367981 A1 | 12/2016 | Wunderle et al. |
| 2017/0002399 A1 | 1/2017 | Eberhart et al. |

FOREIGN PATENT DOCUMENTS

| | | |
|---|---|---|
| CN | 1146017 A | 3/1997 |
| CN | 1354692 A | 6/2002 |
| CN | 1593338 A | 3/2005 |
| CN | 101004423 A | 7/2007 |
| CN | 101312759 A | 11/2008 |
| EP | 0459241 B1 | 10/1994 |
| EP | 0637999 A1 | 2/1995 |
| EP | 0527905 B1 | 11/1995 |
| EP | 1065378 B1 | 4/2002 |
| EP | 1411340 A2 | 4/2004 |
| EP | 1411340 A3 | 5/2004 |
| EP | 1345697 B1 | 6/2007 |
| EP | 1658890 B1 | 5/2008 |
| EP | 1345551 B1 | 4/2009 |
| EP | 2345739 A2 | 7/2011 |
| EP | 2345739 A3 | 10/2011 |
| JP | H08327594 A | 12/1996 |
| JP | H10206384 A | 8/1998 |
| JP | 2001500966 A | 1/2001 |
| JP | 2001521818 A | 11/2001 |
| JP | 2002370200 A | 12/2002 |
| JP | 2003074462 A | 3/2003 |
| JP | 2003536058 A | 12/2003 |
| JP | 2004025159 A | 1/2004 |
| JP | 2004108285 A | 4/2004 |
| JP | 2004180594 A | 7/2004 |
| JP | 2005323519 A | 11/2005 |
| JP | 2005337415 A | 12/2005 |
| JP | 2005345463 A | 12/2005 |
| JP | 2007506430 A | 3/2007 |
| JP | 2007155491 A | 6/2007 |
| JP | 2007198765 A | 8/2007 |
| JP | 2008513022 A | 5/2008 |
| WO | WO-9322053 A1 | 11/1993 |
| WO | WO-9604547 A1 | 2/1996 |
| WO | WO-9614934 A1 | 5/1996 |
| WO | WO-9810277 A1 | 3/1998 |
| WO | WO-9852691 A1 | 11/1998 |
| WO | WO-9853300 A2 | 11/1998 |
| WO | WO-9853300 A3 | 2/1999 |
| WO | WO-9922868 A1 | 5/1999 |

(56) References Cited

FOREIGN PATENT DOCUMENTS

| | | |
|---|---|---|
| WO | WO-9933559 A1 | 7/1999 |
| WO | WO-9936766 A1 | 7/1999 |
| WO | WO-9940174 A1 | 8/1999 |
| WO | WO-0040712 A1 | 7/2000 |
| WO | WO-0060362 A1 | 10/2000 |
| WO | WO-0061198 A1 | 10/2000 |
| WO | WO-0101025 A2 | 1/2001 |
| WO | WO-0132930 A1 | 5/2001 |
| WO | WO-0138865 A1 | 5/2001 |
| WO | WO-0101025 A3 | 7/2001 |
| WO | WO-0185341 A1 | 11/2001 |
| WO | WO-0192575 A1 | 12/2001 |
| WO | WO-0224949 A1 | 3/2002 |
| WO | WO-0241995 A1 | 5/2002 |
| WO | WO-0243615 A2 | 6/2002 |
| WO | WO-0243864 A2 | 6/2002 |
| WO | WO-0243864 A3 | 8/2002 |
| WO | WO-0243615 A3 | 3/2003 |
| WO | WO-03044528 A2 | 5/2003 |
| WO | WO-03062462 A2 | 7/2003 |
| WO | WO-03085379 A2 | 10/2003 |
| WO | WO-03085379 A3 | 12/2003 |
| WO | WO-2004038363 A2 | 5/2004 |
| WO | WO-03044528 A3 | 6/2004 |
| WO | WO-2004061085 A2 | 7/2004 |
| WO | WO-2004062804 A1 | 7/2004 |
| WO | WO-2004080597 A2 | 9/2004 |
| WO | WO-2004061085 A3 | 10/2004 |
| WO | WO-2004098757 A2 | 11/2004 |
| WO | WO-2004038363 A3 | 12/2004 |
| WO | WO-2005072858 A1 | 8/2005 |
| WO | WO-2005075081 A1 | 8/2005 |
| WO | WO-2005091820 A2 | 10/2005 |
| WO | WO-2005108620 A2 | 11/2005 |
| WO | WO-2005118867 A2 | 12/2005 |
| WO | WO-2005121308 A1 | 12/2005 |
| WO | WO-2005123950 A2 | 12/2005 |
| WO | WO-2006032044 A2 | 3/2006 |
| WO | WO-2005108620 A3 | 4/2006 |
| WO | WO-2004098757 A3 | 5/2006 |
| WO | WO-2005091820 A3 | 10/2006 |
| WO | WO-2006032044 A3 | 1/2007 |
| WO | WO-2007002579 A2 | 1/2007 |
| WO | WO-2007064635 A1 | 6/2007 |
| WO | WO-2007082480 A1 | 7/2007 |
| WO | WO-2007109375 A2 | 9/2007 |
| WO | WO-2005118867 A3 | 12/2007 |
| WO | WO-2008012104 A2 | 1/2008 |
| WO | WO-2008024319 A2 | 2/2008 |
| WO | WO-2008030631 A2 | 3/2008 |
| WO | WO-2008024319 A3 | 4/2008 |
| WO | WO-2008039875 A1 | 4/2008 |
| WO | WO-2008012104 A3 | 5/2008 |
| WO | WO-2008115626 A2 | 9/2008 |
| WO | WO-2007109375 A3 | 10/2008 |
| WO | WO-2008115626 A3 | 11/2008 |
| WO | WO-2009008236 A1 | 1/2009 |
| WO | WO-2009015296 A1 | 1/2009 |
| WO | WO-2007002579 A3 | 9/2009 |
| WO | WO-2009108260 A2 | 9/2009 |
| WO | WO-2009129415 A1 | 10/2009 |
| WO | WO-2009108260 A3 | 12/2009 |
| WO | WO-2010041174 A1 | 4/2010 |
| WO | WO-2010041231 A2 | 4/2010 |
| WO | WO-2010042784 A3 | 7/2010 |
| WO | WO-2010041231 A3 | 9/2010 |
| WO | WO-2010109392 A1 | 9/2010 |
| WO | WO-2010130762 A2 | 11/2010 |
| WO | WO-2010141921 A1 | 12/2010 |
| WO | WO-2011003941 A1 | 1/2011 |
| WO | WO-2011011172 A1 | 1/2011 |
| WO | WO-2010130762 A3 | 2/2011 |
| WO | WO-2011012621 A1 | 2/2011 |
| WO | WO-2011034621 A2 | 3/2011 |
| WO | WO-2011056215 A1 | 5/2011 |
| WO | WO-2011084703 A2 | 7/2011 |
| WO | WO-2011094577 A2 | 8/2011 |
| WO | WO-2011034621 A3 | 11/2011 |
| WO | WO-2011084703 A3 | 12/2011 |
| WO | WO-2012024657 A1 | 2/2012 |
| WO | WO-2012024658 A2 | 2/2012 |
| WO | WO-2012136333 A2 | 10/2012 |
| WO | WO-2013130910 A1 | 9/2013 |
| WO | WO-2014014587 A2 | 1/2014 |
| WO | WO-2014055936 A1 | 4/2014 |

OTHER PUBLICATIONS

Notice of allowance dated Jul. 1, 2010 for U.S. Appl. No. 11/139,018.
Notice of allowance dated Aug. 13, 2008 for U.S. Appl. No. 10/750,533.
Amendment and Request for Correction of Inventorship mailed Jan. 10, 2008 in U.S. Appl. No. 10/750,533.
Anderson, et al. A miniature integrated device for automated multistep genetic assays. Nucleic Acids Research. 2000;28:e60.
Armani, et al. Re-configurable fluid circuits by PDMS elastomer micromachining. Proceedings of IEEE Micro Electro Mechanical Systems: MEMS. 1999; 222-227.
Auroux, et al. Micro Total Analysis Systems 2. Analytical Standard Operations and Applications. Anal. Chem. 2002; 2637-2652.
Belgrader, et al. A Minisonicator to Rapidly Disrupt Bacterial Spores for DNA Analysis. Anal. Che. 1999; 4232-4236.
Belgrader, et al. PCR Detection of Bacteria in Seven Minutes. Science Magazin. 1999; 284(5413):449-450.
Belgrader, et al. Rapid PCR for Identity Testing Using a Battery-Powered Miniature Thermal Cycler. J Forensic Sci. 1998; 315-319.
Bennett, et al. Toward the 1,000 dollars human genome. Pharmacogenomics, 6 (4) 373-382. (Jun. 2005).
Bianco, et al. Teflon-like coatings for micro devices. CPAC Satellite Workshops. Rome, Italy. Mar. 23, 2009.
Bings, et al. Microfluidic Devices Connected to Fused-Silica Capillaries with Minimal Dead Dead Volume. Analytical Chemistry. 1999;71(15):3292-3296.
Birnboim. A Rapid Alkaline Extraction Method for the Isolation of Plasmid DNA. Methods of Enzymology. 1983; 100:243-255.
Blaga, et al. Microfluidic device for automated sample preparation. Poster. MSB Conference. Dalian, China. Oct. 2009.
Blaga, et al. Plastic chips with valves and pumps. MSB Conference. Berlin, Germany. Mar. 2008. Abstract only.
Blazej, et al. Inline injection microdevice for attomole-scale sanger DNA sequencing. Anal Chem. Jun. 15, 2007;79(12):4499-506. Epub May 12, 2007.
Blazej, et al. Microfabricated bioprocessor for integrated nanoliter-scale Sanger DNA sequencing. Proc. Natl. Acad. Sci. USA 2006;103:7240-7245.
Blazej, et al. Polymorphism Ratio Sequencing: A New Approach for Single Nucleotide Polymorphism Discovery and Genotyping. Genome Research. 2003;13:287-293.
Branton, et al. The potential and challenges of nanopore sequencing. Nat Biotechnol. Oct. 2008;26(10):1146-53. doi: 10.1038/nbt.1495.
Brenner, et al. Gene expression analysis by massively parallel signature sequencing (MPSS) on microbead arrays. Nature Biotechnology, 18: 630-634 (2000).
Buchholz, et al. The use of light scattering for precise characterization of polymers for DNA sequencing by capillary electrophoresis. Electrophoresis. 2001;22:4118-4128.
Burns, et al. An Integrated Nanoliter DBA Analysis Device. Science Magazine. 1998; 484-487.
Call, et al. Detecting and genotyping *Escherichia coli* 0157:H7 using multiplexed PCR and nucleic acid microarrays. International Journal of Food Microbiology. 2001; 67:71-80.
Cameron, et al. High Internal Phase Emulsions (HIPEs) Structure, Properties and Use in Polymer Preparation. University of Strathclyde. 1995; 163-214.
Canadian Office Action dated Jun. 10, 2011 for CA Application No. 2512071.

(56) References Cited

OTHER PUBLICATIONS

Capanu, et al. Design Fabrication and Testing of a Bistable Electromagnetically Actuated Microvalve. Journal of Microeclectromechanical System. 2000; 9:181-189.

Caplus abstract of Krohkin et al. Modified silica as a stationary phase for ion chromatography. Journal of Chromatography A. 1995;706:93-8.

Chan, et al. Microfabricated Polymer Devices for Automated Sample Delivery of Peptides for Analysis by Electrospray Ionization Tandem Mass Spectrometry. Analytical Chemistry. 1999;71(20):4437-4444.

Chandler, et al. Automated immunomagnetic separation and microarray detection of E. coli 0157:H7 from poultry carcass rinse. International Journal of Food Microbiology. 2001; 70:143-154.

Charlieu, et al. 3' Alu PCR: a simple and rapid method to isolate human polymorphic markers. Nucleic Acids Res. Mar. 25, 1992;20(6):1333-7.

Chiem, et al. Microchip systems for immunoassay: an integrated immunoreactor with electrophoretic separation for serum theophylline determination. Clinical Chemistry.1998;44(3):591-598.

Chiem, et al. Room temperature bonding of micromachined glass devices for capillary electrophoresis. Sensors and Actuators. 2000;B63(3):147-152.

Chinese office action dated Jan. 18, 2012 for CN 200980108368.7. (In Chinese with English translation).

Chinese Office Action dated Jan. 25, 2008 for Application No. 2003801100666.

Chinese office action dated Jan. 31, 2011 for CN 200580035911.7. (In Chinese with English translation).

Chinese office action dated Feb. 24, 2010 for CN Application No. 200780018073.1.

Chinese office action dated Jul. 8, 2011 for CN 200580035911.7. (In Chinese with English translation).

Coleman, et al. A sequential injection microfluidic mixing strategy. Microfluidics and Nanofluidics. 2005;319-327.

Co-pending U.S. Appl. No. 14/659,108, filed Mar. 16, 2015.
Co-pending U.S. Appl. No. 14/824,333, filed Aug. 12, 2015.
Co-pending U.S. Appl. No. 14/919,620, filed Oct. 21, 2015.
Co-pending U.S. Appl. No. 15/037,039, filed May 16, 2016.
Co-pending U.S. Appl. No. 15/117,053, filed Aug. 5, 2016.
Co-pending U.S. Appl. No. 15/154,086, filed May 13, 2016.

Curcio, et al. Continuous Segmented-Flow Polymerase Chain Reaction for High-Throughput Miniaturized DNA Amplification. Analytical Chemistry. 2003;75(1):1-7.

Datasheet Cycle Sequencing, Retrieved from the internet, URL:http//answers.com/topic/cycle sequencing. Printed Sep. 3, 2010, pp. 1-2.

Delehanty, et al. A Microarray Immunoassay for Simultaneous Detection of Proteins and Bacteria. Anal. Chem. 2002; 74:5681-5687.

Diehl et al. BEAMing: single-molecule PCR on microparticles in water-in-oil emulsions. Nature Methods 3(7):551-559 (2006).

Dodson, et al. Fluidics Cube for Biosensor Miniaturization. Anal. Chem. 2001; 3776-3780.

Doherty, et al. Sparsely Cross-linked "Nanogel" Matrices as Fluid, Mechanically Stablized Polymer Networks for High-Throughput Microchannel DNA Sequencing. Analytical Chemistry. 2004;76:5249-5256.

Doherty, et al. Sparsely cross-linked "nanogels" for microchannel DNA sequencing. Electrophoresis. 2003;24(24):4170-4180.

Dorfman, et al. Contamination-Free Continuous Flow Microfluidic Polymerase Chain Reaction for Quantitative and Clinical Applications. Analytical Chemistry. 2005;77(11):3700-3704.

Doyle, et al. Self-Assembled Magnetic Matrices for DNA Separation Chips. Science. 2000;295:2237.

Dressman, et al. Transforming single DNA molecules into fluorescent magnetic particles for detection and enumeration of genetic variations. Proc Natl Acad Sci USA. 2003;100(15):8817-8822.

Duffy, et al. Rapid Prototyping of Microfluidic Systems in Poly(dimethylsiloxane). Anal. Chem. 1998; 4974-4984.

Eid, et al. Real-time DNA sequencing from single polymerase molecules. Science. Jan. 2, 2009;323(5910):133-8. doi: 10.1126/science.1162986. Epub Nov. 20, 2008.

Emrich, et al. Microfabricated 384-Lane Capillary Array Electrophoresis Bioanalyzer for Ultrahigh-Throughput Genetic Analysis. Analytical Chemistry. 2002;74(19):5076-5083.

Ericson, et al. Electroosmosis- and Pressure-Driven Chromatography in Chips Using Continuous Beds. Analytical Chemistry. 2000;72(1):81-87.

Erratum for Margulies, et al. Genome sequencing in microfabricated high-density picolitre reactors. Nature. 2005;437(7057):376-80.

European office action dated Apr. 7, 2011 for EP Application No. 05804847.1.

European search report and search opinion dated Jun. 6, 2011 for Application No. 10011511.2.

European search report and search opinion dated Jun. 22, 2016 for EP Application No. 11818879.6.

European search report and search opinion dated Aug. 17, 2011 for Application No. 08799648.4.

European search report dated Dec. 18, 2009 for Application No. 03808583.3.

European search report dated Sep. 1, 2010 for Application No. 5804847.1.

Ewing, et al. Base-Calling of Automated Sequencer Traces Using Phred. I. Accuracy Assessment. Genome Research. 1998;8:175-185.

Ewing, et al. Base-Calling of Automated Sequencer Traces Using Phred. II. Error probabilities. Genome Research. 1998;8:186-194.

Figeys, et al. A Microfabricated Device for Rapid Protein Identification by Microelectrospray Ion Trap Mass Spectrometry. Analytical Chemistry. 1997;69(16):3153-3160.

Figeys, et al. An Integrated Microfluidics-Tandem Mass Spectrometry System for Automated Protein Analysis. Analytical Chemistry. 1998;70(18):3728-3734.

Figeys, et al. Microfabricated Device Coupled with an Electrospray Ionization Quadrupole Time-of-Flight Mass Spectrometer: Protein Identifications Based on Enhanced-Resolution Mass Spectrometry and Tandem Mass Spectrometry Data. Rapid Communications in Mass Spectrometry. 1998;12:1435-1444.

Figeys, et al. Nanoflow Solvent Gradient Delivery from a Microfabricated Device for Protein Identifications by Electrospray Ionization Mass Spectrometry. Analytical Chemistry. 1998;70(18):3721-3727.

Francis, et al. Flow analysis based on a pulsed flow of solution: theory, instrumentation and applications. Talanta. 2002;58(6):1029-1042.

Franklin, et al. Apollo 200: an integrated platform for DNA profiling. Poster. MCB Conference. Prague, Czech Republic. Mar. 2010.

Fuentes, et al. Detecting minimal traces of DNA using DNA covalently attached to superparamagnetic nanoparticles and direct PCR-ELISA. Biosens Bioelectron. Feb. 15, 2006;21(8):1574-80. Epub Aug. 29, 2005.

Fuller, et al. The challenges of sequencing by synthesis. Nat Biotechnol. Nov. 2009;27(11):1013-23. doi: 10.1038/nbt.1585. Epub Nov. 6, 2009.

Gau, et al. A MEMS based amperometric detector for E. coli bacteria using self-assembled monolayers. Biosensors & Bioelectronic. 2001; 16:745-755.

Ghadessy, et al. Directed evolution of polymerase function by compartmentalized self-replication. Proc Natl Acad Sci USA. 2001;98:4552-4557.

Giddings, et al. A software system for data analysis in automated DNA sequencing. Genome Research. 1998;8:644-665.

Goll, et al. Microvalves with bistable buckled polymer diaphragms. Journal of Micromechanics and Microengineering. 1996;6:77-79.

Grover, et al. An integrated microfluidic processor for single nucleotide polymorphism-based DNA computing. Lab on a Chip. 2005;5(10):1033-1040.

Grover, et al. Development and multiplexed control of latching pneumatic valves using microfluidic logical structures. Lab on a chip. 2006;6:623-631.

(56) References Cited

OTHER PUBLICATIONS

Grover, et al. Monolithic membrane valves and diaphragm pumps for practical large-scale integration into glass microfluidic devices. Sensors and Actuators. 2003;B89:315-323.
Grover, et al. Practical Valves and Pumps for Large-Scale Integration into Microfludic Analysis Devices. Micro Total Analysis Systems. 2002;1:136-138.
Hansen, et al. A robust and scalable microfluidic metering method that allows protein crystal growth by free interface diffusion. Proc Natl Acad Sci USA. 2002;99(26):16531-16536.
Hansen, et al. Polymerase chain reaction assay for the detection of *Bacillus cereus* group cells. FEMS Microbology Letters. 2001; 202:209-213.
Harrison, et al. Micromachining a Miniaturized Capillary Electrophoresis-Based Chemical Analysis System on a Chip. Science. 1993;261(5123):895-897.
Hartmann, et al. Direct immobilization of antibodies on phthalocyaninato-polysiloxane photopolymers. Thin Solid Films. 1994; 245:206-210.
Hartmann, et al. One-step immobilization of immunoglobulin G and potential of the method for application in immunosensors. Sensors and Actuators. 1995; 28 (2):143-149.
Hayes, et al. Edge: A Centralized Resource for the Comparison, Analysis, and Distribution of Toxicogenomic Information. Molecular Pharmacology. 2005;67(4):1360-1368.
He, et al. Fabrication of Nanocolumns for Liquid Chromatography. Anal. Chem. 1998; 3790-3797.
Heath, et al. PCR primed with VNTR core sequences yields species specific patterns and hypervariable probes. Nucleic Acids Res. Dec. 11, 1993;21(24):5782-5.
Hjerten. High-performance electrophoresis : Elimination of electroendosmosis and solute adsorption. J. Chromotography. 1985; 347:191-198.
Hosokawa, et al. A Pneumatically-Actuated Three-Way Microvalve Fabricated with Polydimcthylsiloxanc Using the Membrane Transfer Technique. J. Micinicch. Microcng. 2000; 10:415-420.
Hultman, et al. Bidirectional Solid-Phase Sequencing of in Vitro-Amplified Plasmid DNA. BioTechniques. 1991;10(1):84-93.
International Preliminary Report for corresponding PCT Application No. PCT/CA2000/01421 dated Feb. 14, 2002.
International Preliminary Report for corresponding PCT Application No. PCT/US2005/018678 dated Nov. 13, 2007.
International Preliminary Report for corresponding PCT Application No. PCT/US2005/033347 dated Mar. 20, 2007.
International Preliminary Report for corresponding PCT Application No. PCT/US2007/007381 dated Sep. 23, 2008.
International Preliminary Report for corresponding PCT Application No. PCT/US2007/02721 dated Aug. 5, 2008.
International Preliminary Report for corresponding PCT Application No. PCT/US2007/061573 dated Aug. 26, 2008.
International search report and written opinion dated Oct. 29, 2007 for PCT/US2005/018678.
International search report and written opinion dated Jan. 5, 2012 for PCT Application No. US2011/048527.
International search report and written opinion dated Mar. 16, 2012 for PCT/US2011/048528.
International search report and written opinion dated Mar. 24, 2011 for PCT Application No. US2010/58227.
International search report and written opinion dated Apr. 30, 2012 for PCT/US2012/021217.
International search report and written opinion dated Jun. 9, 2011 for PCT Application No. US2011/30973.
International search report and written opinion dated Jul. 15, 2008 for PCT/US2007/007381.
International search report and written opinion dated Sep. 1, 2010 for PCT Application No. US2010/040490.
International search report and written opinion dated Oct. 26, 2011 for PCT Application No. US11/38180.
International search report dated Sep. 1, 2010 for PCT/US2010/040490.
International search report dated Oct. 6, 2010 for PCT Application No. US10/37545.
International search report dated Apr. 5, 2001 for PCT Application No. CA2000/01421.
International search report dated May 14, 2010 for PCT Application No. US2009/06640.
International search report dated Jul. 11, 2008 for PCT Application No. US07/61573.
International search report dated Jul. 30, 2010 for PCT Application No. US2010/36464.
International search report dated Aug. 18, 2009 for PCT Application No. US09/00419.
International search report dated Aug. 23, 2006 for PCT Application No. US2005/033347.
International search report dated Aug. 26, 2004 PCT Application No. US2003/41466.
International search report dated Sep. 25, 2007 for PCT Application No. US2007/02721.
International Search Report for PCT/US2005/033347.
International written opinion dated Oct. 6, 2010 for PCT Application No. US10/37545.
International written opinion report dated Jul. 30, 2010 for PCT Application No. US2010/36464.
Jacobson, et al. Electrokinetic Focusing in Microfabricated Channel Structures. Anal. Chem., 1997, 69 (16), pp. 3212-3217.
Jacobson, et al. High-Speed Separations on a Microchip. Anal. Chem. 1994; 1114-1118.
Jacobson, et al. Integrated Microdevice for DNA Restriction Fragment Analysis Anal. Chem. 1996; 720-723.
Japanese office action dated Jan. 5, 2012 for Application No. 2007-532553 (in Japanese with English translation).
Japanese Office Action dated Jan. 13, 2010 for JP Application No. 2005-508628.
Japanese office action dated Mar. 1, 2011 for JP Application. No. 2007-515379.
Japanese office action dated May 11, 2012 for Application No. 2008-553535 (English translation).
Japanese office action dated May 27, 2011 for Application No. 2007-532553 (in Japanese with English translation).
Japanese office action dated Jul. 28, 2011 for Application No. 2008-553535 (in Japanese with English translation).
Japanese Office Action dated Aug. 10, 2010 for JP Application No. 2005-508628.
Japanese Office Action dated Dec. 21, 2010 for Application No. JP2001-540363 (in Japanese with English translation).
Japanese Office Action dated Apr. 27, 2010 for Application No. JP2001-540363 (in Japanese with English translation).
Ju, et al. Fluorescence energy transfer dye-labeled primers for DNA sequencing and analysis. Proc. Natl. Acad. Sci. USA. 1995;92:4347-4351.
Kamei, et al. Integrated Amorphous Silicon Photodiode Detector for Microfabricaqted Capillary Electrophoresis Devices. Micro Total Analysis Systems. 2002; 257-259.
Kamei, et al. Integrated hydrogenated amorphous Si photodiode detector for microfluidic bioanalytical devices. Anal Chem. Oct. 15, 2003;75(20):5300-5.
Kan, et al. A novel thermogelling matrix for microchannel DNA sequencing based on poly-N-alkoxyalkylaclylamide copolymers. Electrophoresis. 2003;24(24):4161-4169.
Kimura, et al. Restriction-Site-Specific PCR as a Rapid Test to Detect Enterohemorrhagic *Escherichia coli* 0157:H7 Strains in Environmental Samples. Applied and Environmental Microbiology. Jun. 2000; 2513-2519.
Koch, et al. Optical flow-cell multichannel immunosensor for the detection of biological warfare agents. Biosens Bioelectron. Jan. 2000;14(10-11):779-84.
Koh, et al. Integrating Polymerase Chain Reaction, Valving, and Electrophoresis in a Plastic Device for Bacterial Detection. Analytical Chemistry. 2003;75(17):4591-4598.
Kong, et al. Rapid detection of six types of bacterial pathogens in marine waters by multiplex PCR. Water Research. 2002; 36: 2802-2812.

(56) References Cited

OTHER PUBLICATIONS

Kopp, et al. Chemical Amplification Continuous-Flow PCR on a Chip. Science. 1998;280:1046-1048.
Korean office action dated Mar. 5, 2012 for KR 10-2007-7008423. (In Korean with English translation).
Kourentzi, et al. Microbial identification by immunohybridization assay of artificial RNA labels. Journal of Microbiological Methods. 2002; 49:301-306.
Kuhnert, et al. Detection System for *Escherichia coli*-Specific Virulence Genes: Absence of Virulence Determinants in B and C Strains. applied and Environmental Microbiology. 1997:703-709.
Lagally, et al. Fully integrated PCR-capillary electrophoresis microsystem for DNA analysis. Lab on a Chip. 2001;1(2):102-107.
Lagally, et al. Integrated Portable Genetic Analysis Microsystem for Pathogen/Infectious Disease Detection. Analytical Chemistry. 2004;76:3162-3170.
Lagally, et al. Monolithic integrated microfluidic DNA amplification and capillary electrophoresis analysis system. Sensors and Actuators. 2000;B63(3)138-146.
Lagally, et al. Single-Molecule DNA Amplification and Analysis in an Integrated Microfluidic Device. Analytical Chemistry. 2001;73(3): 565-570.
Lazar, et al. Subattomole-Sensitivity Microchip Nanoelectrospray Source with Time-of-Flight Mass Spectrometry Detection. Analytical Chemistry. 1999;71(17):3627-3631.
Lee, et al. Polymer nanoengineering for biomedical applications. Annals Biomed. Eng. 2006;34:75-88.
Li, et al. Integration of Microfabricated Devices to Capillary Electrophoresis-Electrospray Mass Spectrometry Using a Low Dead Volume Connection: Application to Rapid Analyses of Proteolytic Digests. Analytical Chemistry. 1999;71(15):3036-3045.
Li, et al. Rapid and sensitive separation of trace level protein digests using microfabricated devices coupled to a quadrupole—time-of-flight mass spectrometer. Electrophoresis. 2000;21:198-210.
Li, et al. Separation and Identification of Peptides from Gel-Isolated Membrane Proteins Using a Microfabricated Device for Combined Capillary Electrophoresis/Nanoelectrospray Mass Spectrometry. Analytical Chemistry. 2000;72(3):599-609.
Licklider, et al. A Micromachined Chip-Based Electrospray Source for Mass Spectrometry. Analytical Chemistry. 2000;72(2):367-375.
Ligler, et al. Integrating Waveguide Biosensor. Anal Chem. Feb. 1, 2002;74(3):713-9.
Lisec, et al. A bistable pneumatic microswitch for driving fluidic components. Sensors and Actuators. 1996;A54:746-749.
Liu, et al. Automated parallel DNA sequencing on multiple channel microchips. Proc. Natl. Acad. Sci. USA. 2000;97(10):5369-5374.
Liu, et al. Optimization of High-Speed DNA Sequencing on Microfabricated Capillary Electrophoresis Channels. Analytical Chemistry. 1999;71:566-573.
Lu, et al. New valve and bonding designs for microfluidic biochips containing proteins. Anal. Chem. 2007; 79:994-1001.
Mamanova, et al. FRT-seq: amplification-free, strand-specific transcriptome sequencing. Nat Methods. Feb. 2010;7(2):130-2. doi: 10.1038/nmeth.1417. Epub Jan. 17, 2010.
Manz, et al. Miniaturized Total Chemical Analysis Systems: A Novel Concept for Chemical Sensing. Sensors & Actuators. 1990; 244-248.
McLaughlin, et al. Molecular Approaches to the Identification of *Streptococci*. Methods in Molecular Medicine. 1998; 15:117-139.
Medintz, et al. Genotyping Energy-Transfer Cassette Labeled Short Tandem Repeat Amplicons with Capillary Array Electrophoresis Microchannel Plates. Clinical Chemistry. 2001; 1614-1621.
Medintz, et al. High-Performance Genetic Analysis Using Microfabricated Capillary Array Electroporesis Microplates. Electrophoresis. 2001; 3845-3856.
Medintz, et al. High-Performance Multiplex SNP Analysis of Three Hemochmromatosis-Related Mutations with Capillary Array Electrophoresis Microplates. Genome Research. 2001; 413-421.
Medintz, et al. Novel Energy Transfer Fluorescence Labeling Cassette. BioTechniques. 2002; 32(2):270.
Melin, et al. A Passive 2-Dimensional Liquid Sample Micromixer. 7th International Conference on Miniaturized Chemical and Biochemical Analysis Systems. 2003;167-170.
Metzker, M. Sequencing technologies—the next generation. Nat Rev Genet. Jan. 2010;11(1):31-46. doi: 10.1038/nrg2626. Epub Dec. 8, 2009.
MillGat pump user manual, version 2.12, published 2005, pp. 1-28.
Mitra, et al. Digital genotyping and haplotyping with polymerase colonies. Proc Natl Acad Sci USA 2003.100(10):15926-5931.
Nataro, et al. Diarrheagenic *Escherichia coli*. Clinical MicroBiology Reviews. Jan. 1998;142-201.
Norris, et al. Fully-integrated, multiplexed STR-based human identification using a single microfluidic chip and automated instrument. Available at http://www.promega.com/geneticidproc/ussymp20proc/oralpresentations/landersbienvenue.pdf. Accessed Jun. 2, 2010.
Notice of allowance dated May 5, 2015 for U.S. Appl. No. 13/202,884.
Notice of allowance dated Jun. 9, 2011 for U.S. Appl. No. 12/831,949.
Notice of allowance dated Sep. 8, 2011 for U.S. Appl. No. 12/820,390.
Obeid, et al. Microfabricated Device for DNA and RNA Amplification by Continuous-Flow Polymerase Chain Reaction and Reverse Transcription-Polymerase Chain Reaction with Cycle Number Selection. Analytical Chemistry. 2003;75(2): 288-295.
Ocvirk, et al. High Performance Liquid Chromatography Partially Integrated onto a Silicon Chip. Analytical Methods and Instrumentation. 1995;2:74-82.
Ocvirk, et al. Optimization of confocal epifluorescence microscopy for microchip-based miniaturized total analysis systems. The Analyst. 1998;123:1429-1434.
Office action dated Jan. 7, 2011 for U.S. Appl. No. 12/844,544.
Office action dated Jan. 20, 2010 for U.S. Appl. No. 11/978,224.
Office action dated Feb. 22, 2010 for U.S. Appl. No. 11/139,018.
Office action dated Mar. 2, 2008 for U.S. Appl. No. 10/540,658.
Office action dated Mar. 24, 2015 for U.S. Appl. No. 13/202,884.
Office action dated Mar. 29, 2012 for U.S. Appl. No. 12/789,186.
Office action dated Mar. 30, 2012 for U.S. Appl. No. 12/795,515.
Office action dated Apr. 11, 2012 for U.S. Appl. No. 11/139,018.
Office action dated Apr. 29, 2009 for U.S. Appl. No. 11/139,018.
Office action dated May 22, 2012 for U.S. Appl. No. 12/526,015.
Office action dated Aug. 27, 2008 for U.S. Appl. No. 11/139,018.
Office action dated Oct. 8, 2008 for U.S. Appl. No. 10/540,658.
Office action dated Oct. 25, 2010 for U.S. Appl. No. 11/978,224.
Office action dated Nov. 6, 2009 for U.S. Appl. No. 11/139,018.
Office action dated Dec. 11, 2009 for U.S. Appl. No. 11/726,701.
Office Action Final dated Feb. 6, 2008 issued in U.S. Appl. No. 11/139,018.
Office Action dated Apr. 27 2007 in U.S. Appl. No. 11/139,018, filed May 25, 2005.
Office Action dated Jul. 2, 2007 in U.S. Appl. No. 10/540,658, filed Jun. 23, 2005.
Office Action dated Jul. 12, 2007 in U.S. Appl. No. 10/750,533, filed Dec. 29, 2003.
Oh, et al. A review of microvalves. J. Micromech. Microeng. 2006; 16:R13-R39.
Ohori, et al. Partly disposable three-way mirovalve for a medical micro total analysis system (muTAS). Sensors and Actuators. 1998;A64(1): 57-62.
Oleschuk, et al. Trapping of Bead-Based Reagents within Microfluidic Systems: On-Chip Solid-Phase Extraction and Electrochromatography. Analytical Chemistry. 2000;72:585-590.
Olsen, et al. Immobilization of DNA Hydrogel Plugs in Microfluidic Channels. Analytical Chemistry. 2002;74:1436-1441.
O'Mahony, et al. A real time PCR assay for the detection and quantitation of Mycobacterium avium subsp. Paratuberculosis using SyBR Green and the Light Cycler. Journal of Microbiological Methods. 2002; 51:283-293.
Paegel, et al. High-throughput DNA sequencing with a 96-lane capillary array electrophoresis bioprocessor. Proc Natl Acad Sci USA. 2002;99:574-579.

(56) References Cited

OTHER PUBLICATIONS

Paegel, et al. Microchip Bioprocessor for Integrated Nanovolume Sample Purification and DNA Sequencing. Analytical Chemistry. 2002;74(19):5092-5098.
Paegel, et al. Microfluidic devices for DNA sequencing: sample preparation and electrophoretic analysis. Current Opinion in Biotechnology. 2003;14(1):42-50.
Paegel, et al. Turn Geometry for Minimizing Band Broadening in Microfabricated Capillary Electrophoresis Channels. Analytical Chemistry. 2000;72:3030-3037.
Papadelli, et al. Rapid detection and identification of *Streptococcus macedonicus* by species-specific PCR and DNA hybridisation. International Journal of Food Microbiology. 2003; 81:231-239.
PCT Notification of Transmittal of the International Search Report and The Written Opinion of the International Searching Authority, or the Declaration, dated Jun. 17, 2008, Application No. PCT/US2007/082568 (UCALP067WO).
Peng, et al. Immuno-capture PCR for detection of Aeromonas hydrophila Journal of Microbiological Methods. 2002; 49:335-338.
Peterson, et al. Enzymatic Microreactor-on-a-Chip: Protein Mapping Using Trypsin Immobilized on Porous Polymer Monoliths Molded in Channels of Microfluidic Devices. Analytical Chemistry. 2002;74:4081-4088.
Press, et al., An Integrated Microfluidic Processor for Single Nucleotide Polymorphism-based DNA Computing, Lab on a Chip. 2005, 5:10, 8 pages.
Press, et al., The Art of Scientific Computing, Numerical Recipes in C, 2nd Edition, Cambridge University Press, 1992, (table of Contents).
Quake, et al. From Micro-to Nanofabrication with Soft Materials. Science Magazine. 2000; 1536-1540.
Ramsey, et al. Generating Electrospray from Microchip Devices Using Electroosmotic Pumping. Analytical Chemistry. 1997;69(6):1174-1178.
Reyes, et al. Micro Total Analysis Systems. 1. Introduction Theory and Technology. Anal Chem. 2002; 2623-2636.
Rohr, et al. Porous polymer monoliths: Simple and efficient mixers prepared by direct polymerization in the channels of microfluidic chips. Electrophoresis. 2001;22:3959-3967.
Roth, et al. Fundamentals of Logic Design, 3rd Edition, West Publishing Company, 1985 (Table of Content).
Rowe, et al. Array Biosensor for Simultaneous Identification of Bacterial, Viral and Protein Analytes. Anal. Chem. 1999; 71:3846-3852.
Rowe-Taitt, et al., Simultaneous detection of six biohazardous agents using a planar waveguide array biosensor. Biosensors & Bioelectronics. 2000; 15:579-589.
Ruan, et al. Immunobiosensor Chips for Detection of *Escherichia coli* 0157:H7 Using Electrochemical Impedance Spectroscopy. Anal. Chem. 2002; 74:4814-4820.
Rye, et al. High-sensitivity two-color detection of double-stranded DNA with a confocal fluorescence gel scanner using ethidium homodimer and thiazole orange. Nucleic Acids Research. 1991;19(2):327-333.
Samel. Novel Microfluidic devices based on a thermally responsive PDMS composite. KTH Royal Institute of Technology, Stockholm, Sweden. 2007; 1-80.
Sanford, et al. Photoactivatable Cross-Linked Polyacrylamide for the Site-Selective Immobilization of Antigens and Antibodies Chem Mater. 1998; 10(6): 1510-1520.
Scherer, et al. High-Pressure Gel Loader for Capillary Array Electrophoresis Microchannel Plates. Biotechniques. 2001;31(5):1150-1154.
Schomburg, et al. Design Optimization of Bistable Microdiaphragm Valves. Sensors and Actuators. 1998;A64:259-264.
Seifar, et al. Capillary electrochromatography with 1.8-mum ODS-modified porous silica particles. Journal of Chromatography. 1998; A808:71-77.
Shaikh, et al. A modular microfluidic architecture for integrated biochemical analysis. Proc Natl Acad Sci U S A. Jul. 12, 2005;102(28):9745-50. Epub Jun. 28, 2005.
Shendure, et al. Next-generation DNA sequencing. Nat Biotechnol. Oct. 2008;26(10):1135-45. doi: 10.1038/nbt1486.
Shi, et al. Radial Capillary Array Electrophoresis Microplate and Scanner for High Performance Nucleic Acid Analysis. Anal. Chem. 1999; 5354-5361.
Simpson, et al. High-throughput genetic analysis using microfabricated 96-sample capillary array electrophoresis microplates. Proc Natl Acad Sci USA. 1998;95:2256-2261.
Simpson, et al. Microfabrication Technology for the Production of Capillary Array Electrophoresis Chips. Biomedical Microdevices. 1998;1:7-26.
Soper, et al. Polymeric Microelectro-mechanical Systems. Anal. Chem 2000; 643-651.
Soper, et al. Sanger DNA Sequencing Reactions Performed in a Solid-Phase Nanoreactor Directly Coupled to Capillary Gel Electrophoresis. Analytical Chemistry. 1998;70:4036-4043.
Spiering, et al. Novel microstructures and technologies applied in chemical analysis techniques. 1997 International Conference on Solid-State Sensors and Actuators. 1997;1:511-514.
Stumpfle, et al. Absence of DNA sequence homology with genes of the *Excherichia coli* hemB locus in Shiga-toxin producing *E. coli* (STEC) 0157 Strains. FEMS Microbiology Letters. 1999; 174:97-103.
Sun, et al. A Heater-Integrated Transparent Microchannel Chip for Continuous Flow PCR. Sensors and Actuators B. 2002; 84:283-289.
Tajima, et al. Physiochemical properties and morphology of fluorocarbon films synthesized on crosslinked polyethylene by capacitively coupled octafluorocyclobutane plasma. J. Phys. Chem. C. 2007; 111(11):4358-4367.
Takao, et al. A Pneumatically Actuated Full In-Channel Microvalve With MOSFET-Like Function in Fluid Channel Networks. Journal of Microelectromechanical Systems. 2002;11(5):421-426.
Takao, et al. Microfluidic Integrated Circuits for Signal Processing Using Analogous Relationship Betweeen Pneumatic Microvalve and MOSFET. Journal of Microelectromechanical Systems. 2003;12(4):497-505.
Thomas, et al. Application of Genomics to Toxicology Research. Environmental Health Perspectives. 2002;110(6):919-923.
Tian, et al. Evaluation of Silica Resins for Direct and Efficient Extraction of DNA from Complex Biological Matrices in a Miniaturized Format. Analytical Biochemistry. 2000; 283:175-191.
Tice, et al. Formation of Droplets and Mixing in Multiphase Microfluidics at Low Values of the Reynolds and the Capillary Numbers. Langmuir. 2003;19:9127-9133.
Todd Thorsen, et al., "Microfluidic Large-Scale Integration", www.sciencemag.org, Science, vol. 298, Oct. 18, 2002, pp. 580-584.
U.S. Appl. No. 10/540,658 Office Action Final dated Feb. 19, 2008.
U.S. Appl. No. 90/011,453, filed Jan. 21, 2011.
U.S. Appl. No. 12/026,510, filed Feb. 5, 2008.
U.S. Appl. No. 12/820,390, filed Jun. 22, 2010.
U.S. Appl. No. 12/845,650, filed Jul. 28, 2010.
U.S. Appl. No. 13/075,165, filed Mar. 29, 2011.
U.S. Appl. No. 13/113,968, filed May 23, 2011.
U.S. Appl. No. 13/202,877, filed Sep. 19, 2011.
U.S. Appl. No. 13/202,884, filed Sep. 19, 2011.
U.S. Appl. No. 13/287,398, filed Nov. 2, 2011.
U.S. Appl. No. 13/349,832, filed Jan. 13, 2012.
U.S. Appl. No. 13/367,326, filed Feb. 6, 2012.
U.S. Appl. No. 13/384,753, filed Mar. 15, 2012.
U.S. Appl. No. 14/032,173, filed Sep. 10, 2013.
U.S. Appl. No. 14/474,047, filed Aug. 29, 2014.
Van Der Moolen, et al. A Micromachined Injection Device for CZE: Application to Correlation CZE. Analytical Chemistry. 1997;69(20):4220-4225.
Van Der Moolen, et al. Correlation Capillary Zone Electrophoresis, a Novel Technique to Decrease Detection Limits. Chromatographia. 1995;40(7/8):368-374.
Vazquez, et al. Electrophoretic Injection within Microdevices. Analytical Chemistry. 2002;74:1952-1961.

(56) References Cited

OTHER PUBLICATIONS

Veenstra, et al. The design of an in-plane compliance structure for microfluidical systems. Sensors and Actuators. 2002;B81:377-383.
Verlee, et al. .Fluid Circuit Technology: Integrated Interconnect Technology for Miniature Fluidic Devices. Abbott Laboratories Hospital Division, Abbott Park, IL. 1996; 9-14.
Waller, et al. Quantitative Immunocapture PCR Assay for Detection of Campylobacter jejuni in Foods. Applied Environmental Microbiology. 2000; 66(9):4115-4118.
Walt, et al. Biological Warefare Detection. Analytical Chemistry 2000; 739-746.
Waters, et al. Microchip Device for Cell Lysis, Multiplex PCR Amplification, and Electrophoretic Sizing. Anal. Chem. 1999; 158-162.
Webster, et al. Monolithic Capillary Electrophoresis Device with Integrated Flurorescence Detector. Anal. Chem. 2001;1622-1626.
Weimer, et al. Solid-Phase Capture of Proteins, Spores, and Bacteria. Applied Environmental Microbiology. 2001;67(3):1300-1307.
Wen, et al. Microfabricated isoelectric focusing device for direct electrospray ionization-mass spectrometry. Electrophoresis. 2000;21:191-197.
White, et al. Flash detection/identification of pathogens, bacterial spores and bioterrorism agent biomarker from clinical and environmental matrices. Journal of Microbiological Methods. 2002; 48:139-147.
Wikipedia brochure for defining stocahstic process. Sep. 2, 2009.
Williams, et al. Amplification of complex gene libraries by emulsion PCR. Nature Methods. 2006;3(7):545-50.
Willis, et al. Monolithic teflon membrane valves and pumps for harsh chemical and low-temperature use. Lab Chip. 2007; 7:1469-1474.
WOOLLEy, et al. Functional Integration of PCR Amplification and Capillary Electrophoresis in a Microfabricated DNA Analysis Device. Analytical Chemistry. 1996;68(23):4081-4086.
Wright, et al. Behavior and Use of Nonaqueous Media without Supporting Electrolyte in Capillary Electrophoresis and Capillary Electrochromatography. Analytical Chemistry. 1997;69(16):3251-3259.
Xiang, et al. An Integrated Microfabricated Device for Dual Microdialysis and On-Line ESI-Ion Trap Mass Spectrometry for Analysis of Complex Biological Samples. Analytical Chemistry. 1999;71(8):1485-1490.
Xue, et al. Integrated Multichannel Microchip Electrospray Ionization Mass Spectrometry: Analysis of Peptides from On-Chip Tryptic Digestion of Melittin. Rapid Communications in Mass Spectrometry. 1997;11:1253-1256.
Xue, et al. Multichannel Microchip Electrospray Mass Spectrometry. Analytical Chemistry. 1997;69(3):426-430.
Yacoub-George, et al. Chemiluminescence multichannel immunosensor for biodetection Analytica Chimica Acta. 2002; 457:3-12.
Yang, et al. A MEMS thermopneumatic silicone rubber membrane valve. Sensors and Actuators. 1998;A64(1):101-108.
Yang, et al. An Integrated Stacked Microlaboratory for Biological Agent Detection with DNA and Immunoassays. Biosensors & Bioelectronics. 2002; 17:605-618.
Yu, et al. Preparation of Monolithic Polymers with Controlled Porous Properties for Microfluidic Chip Applications Using Photoinitiated Free Radial Polymerization. Journal of Polymer Science. 2002;40:755-769.
Yu, et al. Towards stationary phases for chromatography on a microchip: Molded porous polymer monoliths prepared in capillaries by photoinitiated in situ polymerization as separation media for electrochromatography. Electrophoresis. 2000;21:120-127.
Zhang, et al. A Microdevice with Integrated Liquid Junction for Facile Peptide and Protein Analysis by Capillary Electrophoresis/Electrospray Mass Spectrometry. Analytical Chemistry. 2000;72(5):1015-1022.
Zhang, et al. Microfabricated Devices for Capillary Electrophoresis-Electrospray Mass Spectrometry. Analytical Chemistry. 1999;71(15):3258-3264.
Zhang, et al. PMMA/PDMS valves and pumps for disposable microfluidics. Lap Chip. 2009; 9:3088-3094.
Zhu, et al. High-Sensitivity Capillary Electrophoresis of Double-Stranded DNA Fragments Using Monomeric and Dimeric Fluorescent Intercalating Dyes. Anal Chem. 1994; 1941-1948.
Office action dated Apr. 1, 2014 for U.S. Appl. No. 13/202,884.
Office action dated Oct. 29, 2013 for U.S. Appl. No. 13/202,884.
Co-pending U.S. Appl. No. 15/342,914, filed Nov. 3, 2016.
Krsek, et al. Comparison of different methods for the isolation and purification of total community DNA from soil. Journal of Microbiological Methods 39.1 (1999): 1-16.
Van Ness, et al. Isothermal Reactions for the Amplification of Oligonucleotides. Proc. Nat. Acad. Sci. USA. 2003;100 (8):4504-4509.
European search report and search opinion dated Sep. 11, 2013 for EP Application No. 10784213.
European search report dated Jul. 13, 2016 for EP Application No. 09714332.5.
European search report dated Oct. 29, 2012 for EP Application No. 07853470.8.
Grodzinski, et al. Microfluidic System Integration in Sample Preparation Chip-Sets—a Summary. Conf. Proc. IEEE Eng. Med. Biol. Soc. 2004;4:2615-2618.
Holland, et al. Point-of-care molecular diagnostic systems—past, present and future. Curr Opin Microbiol. Oct. 2005;8(5):504-9.
International search report and written opinion dated Jan. 29, 2016 for PCT Application No. PCT/US2015/056764.
International search report and written opinion dated Mar. 3, 2015 for PCT Application No. PCT/US2014/066008.
International search report and written opinion dated Mar. 8, 2013 for PCT/US2012/061223.
International search report and written opinion dated Jul. 22, 2013 for PCT Application No. PCT/US2013/028462.
International search report and written opinion dated Oct. 26, 2015 for PCT/US2015/028510.
Lund-Olesen, et al. Capture of DNA in microfluidic channel using magnetic beads: Increasing capture efficiency with integrated microfluidic mixer. Journal of Magnetism and Magnetic Materials 311 (2007): 396-400.
Notice of allowance dated Jan. 31, 2017 for U.S. Appl. No. 14/552,389.
Notice of allowance dated Feb. 19, 2013 for U.S. Appl. No. 12/845,650.
Notice of allowance dated Apr. 25, 2013 for U.S. Appl. No. 12/815,685.
Notice of allowance dated May 3, 2010 for U.S. Appl. No. 11/670,866.
Notice of allowance dated Jun. 25, 2014 for U.S. Appl. No. 13/656,503.
Notice of allowance dated Jul. 8, 2013 for U.S. Appl. No. 13/717,585.
Notice of allowance dated Nov. 12, 2014 for U.S. Appl. No. 13/967,957.
Notice of allowance dated Nov. 22, 2013 for U.S. Appl. No. 13/590,965.
Notice of allowance dated Dec. 7, 2012 for U.S. Appl. No. 12/795,515.
Office action dated Jan. 13, 2017 for U.S. Appl. No. 14/253,622.
Office action dated Jan. 17, 2014 for U.S. Appl. No. 13/656,503.
Office action dated Jan. 22, 2013 for U.S. Appl. No. 12/845,650.
Office action dated Feb. 28, 2013 for U.S. Appl. No. 13/113,968.
Office action dated Mar. 19, 2009 for U.S. Appl. No. 11/670,866.
Office action dated Mar. 24, 2010 for U.S. Appl. No. 11/670,866.
Office action dated Apr. 15, 2015 for U.S. Appl. No. 13/896,581.
Office action dated May 30, 2014 for U.S. Appl. No. 13/656,503.
Office action dated Jul. 1, 2016 for U.S. Appl. No. 14/253,622.
Office action dated Jul. 26, 2012 for U.S. Appl. No. 12/845,650.
Office action dated Aug. 9, 2016 for U.S. Appl. No. 14/500,846.
Office action dated Aug. 23, 2012 for U.S. Appl. No. 13/287,398.
Office action dated Aug. 24, 2012 for U.S. Appl. No. 12/026,510.

(56) References Cited

OTHER PUBLICATIONS

Office action dated Aug. 29, 2012 for U.S. Appl. No. 12/605,217.
Office action dated Sep. 11, 2014 for U.S. Appl. No. 13/967,957.
Office action dated Sep. 15, 2014 for U.S. Appl. No. 13/886,068.
Office action dated Nov. 14, 2012 for U.S. Appl. No. 12/526,015.
Office action dated Dec. 29, 2016 for U.S. Appl. No. 14/824,333.
Office action dates Jan. 15, 2014 for U.S. Appl. No. 12/321,594.
Office action dates Feb. 27, 2013 for U.S. Appl. No. 13/590,965.
Office action dates Sep. 19, 2012 for U.S. Appl. No. 12/321,594.
Office action dates Dec. 7, 2012 for U.S. Appl. No. 13/590,051.
Peoples, et al. Microfluidic Immunoaffinity Separations for Bioanalysis. J. Chromat. B. 2008;866:14-25 (available online Aug. 30, 2007).
Stevens, et al. Bacterial Separation and Concentration from Complex Sample Matrices: a Review. Crit. Rev. Microbiol. 2004;30(1):7-24.
Unger, et al. Monolithic microfabricated valves and pumps by multilayer soft lithography. Science. Apr. 7, 2000;288(5463):113-6.
U.S. Appl. No. 61/709,417, filed Oct. 4, 2012.
Notice of allowance dated Jun. 9, 2017 for U.S. Appl. No. 14/824,333.

| Step | Activity | Source 1 | Source 2 | Destination | Incubation |
|---|---|---|---|---|---|
| 1 | End-Repair | DNA Frags | ER Mix | Out1 | 20C/30m |
| 2 | Heat-Kill | | | | 75C/30m |
| 3 | Mix Vectorette | Out1 | Vectorette | Out2 | |
| 4 | Ligase | Out2 | Ligation Mix | Out1 | 20C/30m |
| 5 | Mix Beads | Out1 | Strep Beads | Out2 | |
| 6 | Capture Beads | Out2 | | BP,W | |
| 7 | Wash Beads | Wash | | BP,W | |
| 8 | Exo Digest | BP | Exo Mix | Out2 | 37C/30m |
| 9 | Heat-Kill | | | | 75C/30m |
| 10 | Output Circles | Out2 | | BP, E | |

LINEAR VALVE ARRAYS

CROSS-REFERENCE

This application is a Continuation of U.S. patent application Ser. No. 13/302,884, filed on Sept. 19, 2011, now U.S. Pat. No. 9,121,058, which is a National Stage Entry of International Patent Application No. PCT/US2011/048528, filed on Aug. 20, 2011, which claims priority to U.S. Provisional Patent Application No. 61/375,758 to Jovanovich et al., filed on Aug. 20, 2010, and to U.S. Provisional Patent Application No. 61/375,791 to Vangbo, filed on Aug. 20, 2010, which are entirely incorporated herein by reference.

STATEMENT AS TO FEDERALLY SPONSORED RESEARCH

This invention was made with Government support under Contract No. HDTRA1-10-C-0077 awarded by the Defense Threat Reduction Agency. The Government has certain rights in the invention.

BACKGROUND OF THE INVENTION

Many protocols in molecular biology involve several iterations of performing a biochemical reaction followed by capture and cleanup of the biochemical reactions. For example, DNA library preparation can involve polishing nucleic acid fragments, A-tailing the polished fragments, and ligating adapters to the A-tailed fragments. Currently, there are few inventions that can perform integrated analysis of any unpurified sample, such as obtaining sequence information from an environmental sample. As such, there is a need in the art for systems that can receive as input an unpurified sample and perform automated sample preparation and analysis to generate laboratory-quality data. Further, biochemical protocols can be improved to facilitate performing such integrated preparation and analyses.

While not necessary, in some cases the invention described herein can use microfluidic components to reduce the amount of samples or reagents required for bioanalytical methods. Such microfluidic components may incorporate different external dimensional form factors, external interfaces, and/or internal fluidic geometries to facilitate performing biochemical protocols. In contrast, many biological and environmental samples are first acquired in volumes far greater than, and incompatible with, the scale of existing microfluidic analytical devices. Thus, some embodiments of the invention provide modular microfluidic components that can be used as components of integrated fluidic systems, and that can interface with effective fluidic communication to preparative modules or methods that operate at a larger scale.

SUMMARY OF THE INVENTION

The invention provides for an automated "Integrated Sample-to-Sequence" (ISS) system comprising: a first module configured to receive a sample comprising a target polynucleotide and modify said target polynucleotide; a second module fluidically connected to the first module configured to receive said modified polynucleotide and perform a sequencing reaction on said modified polynucleotide; and computer logic for controlling the first module and the second module. The first module can comprise a microfluidic channel with pneumatically actuated valves leading to a chamber comprising beads. The first module can comprise a sample processing module configured to modify the target polynucleotide by purifying and fragmenting DNA. In some embodiments, a sample processing module comprises a chamber with magnetic beads and a shearing device.

In some embodiments, the sample is a cellular sample, a tissue sample, a cell fraction, or an environmental sample. The sample can contain as few as about ten or fewer cells, bacteria, or pathogens. The sample can contain larger amounts of nucleic acids or cells, bacteria, or pathogens. The nucleic acid can comprise DNA or RNA. The sample can be no more than 1 microgram of the nucleic acid.

In some embodiments, the first module comprises a plurality of reaction chambers, each fluidically connected to one or more reagent reservoirs and sample wells by microfluidic channels comprising pneumatically actuated valves. The first module can comprise a sample processing module comprising one or more chambers having a volume of greater than about 1 mL for receiving the sample. The first module can comprise a component for fragmenting nucleic acids in the sample. The component for fragmenting nucleic acids can be a sonicator, bead-beater, enzymatic, or other suitable devices for fragmenting nucleic acids.

In some embodiments, the first module comprises a library construction module configured to add adapters to the target polynucleotide. The library construction module can comprise a chamber with adapters. The first module can comprise a library construction module comprising one or more reaction chambers surrounded by one or more pneumatically actuated valves for creating a library of nucleic acid templates from nucleic acids in the sample. The one or more reaction chambers can be fluidically connected to one or more reagent reservoirs comprising adapters.

In some embodiments, the first module comprises an emRCA module configured to perform rolling circle amplification. The emRCA module can comprise a chamber with a strand-displacing polymerase. In some embodiments, the first module comprises an amplification module configured to perform bridge amplification.

In some embodiments, the first module comprises a distribution device capable of creating an emulsion. The distribution device can comprise a first reagent reservoir and a second reagent reservoir, wherein the first reagent reservoir comprises a first liquid that is immiscible with a second liquid in the second reagent reservoir.

In some embodiments, the first module comprises a distribution device capable of distributing the library of nucleic acid templates to a plurality of isolated reaction environments. The first module can comprise a distribution device capable delivering nucleic acids in the sample to a plurality of wells, channels, or chambers. The first module can comprise an automated liquid transfer device. The first module comprises a distribution device capable of delivering nucleic acids in the sample to a plurality of spatially or physically separated locations. The first module can comprise a droplet forming device.

In other embodiments, the first module and the second module occupy a volume of less than about 6 cubic feet. The system can be less than about 3 cubic feet. The system can provide sequence information on said target polynucleotide in less than about 22 hours. The second module can be capable of sequencing at least 250 million, 10 billion, or 100 billion bases in less than 2.5, 4, 5, 6.5, 12, or 22 hours. The system can be capable of providing sequencing information on said target polynucleotide in less than about 2.5, 4, 5, 6.5, or 12 hours.

In some embodiments, the first module performs one or more of the following steps: cell lysis, nucleic acid isolation, nucleic acid fragmentation, end repair, addition of nucleotides, amplification, normalization, and adapter ligation. In some embodiments, computer logic comprises a user interface for inputting control parameters.

In further embodiments, the system can comprise an external pressure source for driving fluid flow within the first module. In some embodiments, fluid flow within the first module is driven by a microfluidic pump. In some embodiments, fluid flow within the first module is driven by one or more pneumatic valves. The first module can be fluidically connected to the second module by a flexible connection.

In some embodiments, the second module comprises a 2MP CMOS image sensor capable of interrogating 500,000 wells. The second module can perform sequencing by synthesis, real-time sequencing, a pyrosequencing, sequencing by ligation, Sanger sequencing, nanopore sequencing, single molecule sequencing, or other nucleic acid sequencing methods that measure physical, chemical, optical, fluorescent, electrochemical, or dimensional aspects of the polynucleotide to determine the sequence.

In some embodiments, the device comprises a valve array comprising a series of valves connected through fluidic connections, the array comprising, in order, a first terminal valve, at least three intermediate valves and a second terminal valve; at least one first port, each fluidically connected through a separate control valve to the first terminal valve; and at least one second port, each fluidically connected through a separate control valve to the second terminal valve. In some embodiments, the at least one first port is a plurality of first ports. In some embodiments, the plurality of first ports are fluidically connected to the first terminal valve through a common rail. In some embodiments, the at least one second port is a plurality of second ports. In some embodiments, the plurality of second ports are fluidically connected to the second terminal valve through a common rail.

In some embodiments, the device comprises a ganged set of valve arrays, comprising: a plurality of valve arrays, each valve array comprising a series of valves connected through fluidic connections, the array comprising, in order, a first terminal valve, at least three intermediate valves and a second terminal valve; at least one first port, each connected through a separate control valve to a first rail that is fluidically connected to each of a plurality of the first terminal valves; and at least one second port, each connected through a separate control valve to a second rail that is fluidically connected to each of a plurality of the second terminal valves. In some embodiments, the device comprises at least one third port, each connected through a separate control valve to a third rail that is fluidically connected to each of a plurality of the first terminal valves, wherein the at least one third port is fluidically connected to at least one first terminal valve to which the at least one first port is not connected. In some embodiments, the device comprises at least one fourth port, each connected through a separate control valve to a fourth rail that is fluidically connected to each of a plurality of the second terminal valves, wherein the at least one fourth port is fluidically connected to at least one second terminal valve to which the at least one third port is not connected. In some embodiments, the device comprises an actuation system configured to actuate in parallel a plurality of the valves in different valve arrays.

In some embodiments, the device comprises N microfluidic chambers in series, wherein N is at least two; at least one channel fluidically connected to said series of N microfluidic chambers; and at least N+1 reservoirs fluidically connected to said channel. In some embodiments, the device comprises microfluidic apparatus comprising: at least one microfluidic channel, said channel comprising N chambers in series, where N is at least two; and at least N+1 reservoirs fluidically connected to said channel, wherein said reservoirs comprise at least two reagents; wherein said chambers and said reservoirs are arranged to allow sequential addition and mixing of reagents from each of said reservoirs. In some embodiments, the device further comprises an outlet reservoir, said outlet reservoir being arranged to allow removal of at least a portion of said reagents from said apparatus. In some embodiments, N is at least 5. In some embodiments, each chamber comprises a valve. In some embodiments, each valve is a pneumatic valve. In some embodiments, each chamber comprises the same volume. In some embodiments, each of said N+1 reservoirs comprises a different reagent. In some embodiments, the channel or series of N microfluidic chambers is unbranched. In some embodiments, the length of said channel or series of N microfluidic chambers is less than about 30 mm. In some embodiments, the channel or series of N microfluidic chambers comprises a first end and a second end, and further comprises at least a first and second channel, wherein said first channel is fluidically connected to said first end and said second channel is fluidically connected to said second end. In some embodiments, at least a first reservoir is connected to said first channel and at least a second reservoir is connected to said second channel. In some embodiments, said first reservoir comprises a nucleic acid sample, PCR mix, cell lysis buffer, reverse transcriptase, restriction enzyme, or ligase. In some embodiments, said second reservoir comprises magnetic beads.

In some embodiments, the valves of the array are diaphragm valves. In some embodiments, the capture particles are magnetically responsive. In some embodiments, the capture particles are immobilized with magnetic force. In some embodiments, the chambers of the array are flanked by a valve.

In some embodiments, the invention provides for a microfluidic apparatus configured for automated preparation of one or more DNA samples for sequencing comprising: a sample loading module, a reagent loading module, a mixing module, a bead-loading module, a bead-capturing module, a bead-washing module, a bead-elution module, a collection module, and a waste disposal module; wherein each of said modules comprises a microfluidic channel, wherein at least three of said modules share a common chamber or valve.

In some embodiments, the system can provide over 5 million base reads in less than 5 hrs. In some embodiments, the system detects 10 microorganisms in a solution of 1 ml of buffer. In some embodiments, the system is capable of detecting as low as 10 microorganisms in a 1 mL sample with a sensitivity greater than 98%, a specificity greater than 98%, or a confidence greater than 98%. In some embodiments, the system is capable of generating about 1.5 Gigabases of sequence data from raw sample in a 0.2 cubic meter breadboard system.

In some embodiments, the system further comprises a receiver configured to receive a sample of more than 0.5 mL, a fluorimeter, and a disposable cartridge fluidly connected to or pre-filled with a lysis buffer, nucleic acid eluting buffer, WGA reagent(s), library construction reagents, normalization reagents. The system can be fully automated.

In some embodiments, the system further comprises a microfluidic cartridge, optionally with one or more of the following: one or more elastomeric valves, one or more pneumatic valves, a magnetic field generator, a fluorescent detector, control electronics, and a pneumatics supply. In some embodiments, the system further comprises a sequencing module. In some embodiments, the system contains at least 10 or 12 sample receiving modules. The system can comprise a bead beater. In some embodiments, the system comprises 2 or more pre-filled cartridges. In some embodiments, the system is less than 5, 4, 3, 2, 1, 0.5, or 0.3 cu ft. In some embodiments, the system comprises a computer readable medium generating sequence data output based on sequence generated by sequencing module, performing quality-scored base calls to variant calling, and sequence alignment.

In some embodiments, the invention comprises a breadboard integrating: a sample processing module, a library construction module; a normalization module; a sequencing module; and a computer readable medium for controlling the modules, communicating between the module(s), remote databases, and/or the user, or processing data.

In some embodiments, the invention comprises pellet of lyophilized reagent(s) for performing WGA, cell lysis, nucleic acid elution, or library construction. In some embodiments, the invention comprises a cartridge comprising one or more microfluidic channels connected to one or more microfluidic chambers, wherein said chambers comprise one or more of the pellets of claim 31. The cartridge can comprise pneumatic valves.

Another aspect of the invention provides for a method for performing sequencing comprising: inputting sample comprising a target polynucleotide into a system that automatically isolates DNA or RNA from the sample and sequences the target polynucleotide. The sample can be an environmental sample, tissue sample, cell fraction, cellular sample, culture, fermentation sample, or any other sample containing nucleic acids. The system can perform the following steps: modifying the target polynucleotide; transferring the modified polynucleotide to a sequencing module; and sequencing the modified polynucleotide in the sequencing module.

The invention also provides for a method for performing sequencing comprising: (a) isolating a target polynucleotide from a sample; (b) modifying the target polynucleotide; (c) transferring the modified polynucleotide to a sequencing module; and (d) sequencing the modified polynucleotide in the sequencing module, wherein each step is automated by computer logic and occurs in a fluidically connected environment. The sample can be an environmental sample, tissue sample, cell fraction, cellular sample, culture, fermentation sample, or any other sample containing nucleic acids.

In some embodiments, greater than about 250 million, 10 billion, or 100 billion bases are sequenced in less than about 0.5, 1, 2.5, 4, 5.5, 6.5, 12, or 22 hours.

The target polynucleotide can be isolated in a first module that comprises a microfluidic device. The microfluidic device can comprise a valve. The valve can be selected from the group consisting of a diaphragm valve, a rotating valve and a pneumatically actuated valve. Some embodiments of valves usable with this invention are described in U.S. patent application Ser. No. 12/321,594 and described herein.

In some embodiments, an isolating step comprises binding the polynucleotide in the sample to particles, which can be magnetic beads. The modifying step can comprise fragmenting the polynucleotide in the sample. The modifying step can comprise circularizing the polynucleotide. The nucleic acids can be circularized using a biotinylated adapter. The modifying step can comprise amplifying the polynucleotide in an emulsion to produce amplified polynucleotides. The modifying step can comprise amplifying the polynucleotide by bridge amplification to produce amplified polynucleotides. The modifying step can comprise immobilizing the amplified polynucleotides to a bead. The modifying step can comprise immobilizing the amplified polynucleotides to the surface of a flow cell.

In some embodiments, the method further comprises transferring the bead to a substrate prior to sequencing the amplified polynucleotides. The sequencing step can comprise a sequencing method selected from the group consisting of sequencing by synthesis, real-time sequencing, pyrosequencing, sequencing by ligation, Sanger sequencing, nanopore sequencing, single molecule sequencing, reversible dye-terminating sequencing, or other nucleic acid sequencing methods that measure physical, chemical, optical, fluorescent, electrochemical, or dimensional aspects of the polynucleotide to determine the sequence.

The invention provides for a kit for performing sequencing comprising: a microfluidic device comprising a chamber fluidically connected via channels to a reservoir, wherein the chamber comprises a pneumatically actuated valve; and an adapter for sequencing nucleic acids.

Another aspect of the invention provides for a method executable by a processor for sequencing a sample comprising: providing a first instruction to a first module for preparing a polynucleotide in the sample for sequencing; providing a second instruction to the first module for transferring the polynucleotide from the first module to a second module; and providing a third instruction to the second module for sequencing the polynucleotide.

Another aspect of the invention provides for a method comprising: providing a linear array; introducing a first fluid from one of the first ports into the first terminal valve; moving the first fluid from the first terminal valve into an intermediate valve; introducing a second fluid from another of the first ports into the first terminal valve; and mixing the first fluid and the second fluid by moving the second fluid into an intermediate valve in which the first fluid was moved to produce a mixed fluid. In some embodiments, the method further comprises introducing capture particles from a first port or a second port into a terminal valve, wherein the capture particles are configured to bind an analyte in the mixed fluid; and binding the analyte to the capture particles by mixing the mixed fluid and the capture particles by moving the mixed fluid and the capture particles back and forth at least once through one of the intermediate valves. In some embodiments, the method further comprises immobilizing the capture particles with bound analyte in the linear valve array; and washing the capture particles by moving a wash solution from at least one of the ports over the capture particles and removing the wash solution from the linear valve array. In some embodiments, the method further comprises eluting the analyte from the capture particles. In some embodiments, the method further comprises moving the analyte to one of the ports. In some embodiments, the method further comprises mixing the eluted analyte with a reagent in the valve array.

Another aspect of the invention provides for a method, comprising: providing a microfluidic apparatus comprising N chambers in series, wherein N is at least two; at least one channel fluidically connected to said series of N chambers; and at least N+1 reservoirs fluidically connected to said channel, wherein at least one of said chambers or said channel is microfluidic; introducing a first reagent from a first reservoir into a first chamber; introducing a second reagent from a second reservoir into a second chamber; and mixing said first and second reagents within said microfluidic apparatus to form a mixed reaction. In some embodiments, said series comprises a first end and a second end, wherein said first reagent is introduced through said first end and said second reagent is introduced through said second end. In some embodiments, the second chamber is adjacent to said first chamber in said series; and mixing comprises moving both said first and second reagents from said first and second chambers to at least a third chamber. In some embodiments, the first and second chambers are the same, and mixing comprises moving both said first and second reagents to another chamber. In some embodiments, introducing said first reagent fills more than one chamber. In some embodiments, introducing said second reagent fills more than one chamber. In some embodiments, the method further comprises introducing a third reagent from a third reservoir into a third chamber, and mixing said third reagent with said mixed reaction to form a second mixed reaction. In some embodiments, the method further comprises repeating the steps of introducing a reagent from a reservoir and mixing said reagent with said mixed reaction, wherein said additional steps are repeated at least N times. In some embodiments, said first or second reagent comprises a target sample, and the method further comprises modifying said target sample in said mixed reaction to form a product solution. In some embodiments, mixing comprises flowing at least one of said reagents in a forward and in a reverse direction. In some embodiments, the method further comprises removing at least a portion of said mixed reaction from said series of chambers through said channel. In some embodiments, the apparatus further comprises valves, and said introducing or mixing of said first or second reagent is performed by opening or closing said valves.

In some embodiments, the method further comprises separating a component of said product solution from the rest of said product solution. In some embodiments, said separating comprises: providing a retention chamber in said series of chambers; providing a solid substrate in said retention chamber, wherein said solid substrate comprises a binding site for said component; mixing said product with said solid substrate such that the component binds to said solid substrate; and flowing said product solution from said retention chamber such that said solid substrate remains in said retention chamber, and wherein said component remains bound to said solid substrate. In some embodiments, said component comprises an affinity tag and said solid substrate comprises a binding partner for said affinity tag. In some embodiments, said component binds through charged interactions to said solid substrate. In some embodiments, said component binds through hydrophobic interactions to said solid substrate. In some embodiments, said component comprises a nucleic acid or an amino acid. In some embodiments, said solid substrate comprises a particle, a magnetic particle, or at least one surface of the retention chamber.

In some embodiments, the method further comprises removing said product solution from said series of chambers; introducing an elution solution into said retention chamber; optionally mixing said elution solution and said solid substrate such that said component is released from said solid substrate; flowing said elution solution out of said retention chamber; and optionally removing said solid substrate from said retention chamber. In some embodiments, the method further comprises providing a sequencing instrument fluidically connected to said microfluidic apparatus and performing sequencing on a component of said product solution.

Another aspect of the invention provides for a method, comprising providing a reaction mixture comprising at least one labeled nucleotide, a polymerizing enzyme, and a nucleic acid polymer, wherein said labeled nucleotide comprises an affinity tag; synthesizing a product nucleic acid from the reaction mixture, wherein said synthesis incorporates the labeled nucleotide comprising the affinity tag into said product nucleic acid; and isolating said product nucleic acid from the reaction mixture by binding to a binding moiety that binds said affinity tag. In some embodiments, the synthesizing step is selected from a DNA polymerizing step, a reverse transcription step and an A-tailing step. In some embodiments, the method further comprises removing unincorporated labeled nucleotide from the reaction mixture before isolating said product nucleic acid from the reaction mixture.

In some embodiments, the method further comprises a step selected from ligating an adapter sequence to said product nucleic acid and polishing said product nucleic acid. In some embodiments, the method further comprises at least one modifying step comprising: providing additional reagents to form a modified reaction mix and modifying said product nucleic acid in said modified reaction mix to form a modified product nucleic acid. In some embodiments, said modifying comprises incorporating dATP to a terminal end of said product nucleic acid; synthesizing a nucleic acid strand complementary to at least a portion of said product nucleic acid; fragmenting said product nucleic acid; ligating an oligonucleotide to said product nucleic acid; or any combination thereof. In some embodiments, the method further comprises isolating the modified nucleic acid from said modified reaction mix.

In some embodiments, said nucleic acid polymer is an RNA molecule, said polymerizing enzyme is a reverse transcriptase, and said synthesizing produces a first DNA strand complementary to said RNA molecule; said additional reagents comprise DNA polymerase; said modifying comprises synthesizing a second DNA strand complementary to the first DNA strand, wherein said first and second DNA strand form a double-stranded DNA molecule. In some embodiments, the method further comprises providing an adapter nucleic acid; ligating the adapter nucleic acid to the double-stranded DNA molecule to produce a ligated DNA molecule; providing a solid substrate comprising a binding moiety for the affinity tag; binding the ligated DNA molecule to the solid substrate; washing unligated adapter nucleic acid away from the ligated DNA molecule bound to the solid substrate; and eluting the ligated DNA molecule from the solid substrate. In some embodiments, the method further comprises adding a labeled enzyme, wherein said labeled enzyme comprises an affinity tag. In some embodiments, said labeled nucleotide and said labeled enzyme comprise different affinity tags.

In some embodiments, the binding moiety is attached to a solid substrate. In some embodiments, the solid substrate is a particle. In some embodiments, the particle is a magnetically responsive particle. In some embodiments, the solid substrate is a wall of a microfluidic channel or chamber. In some embodiments, the product nucleic acid is complementary to said nucleic acid polymer. In some embodiments, the product nucleic acid comprises said nucleic acid polymer. In some embodiments, the product nucleic acid comprises DNA or RNA. In some embodiments, the product nucleic acid is less than about 50 nucleotides in length. In some embodiments, affinity tags are selected from the group consisting of biotin, avidin, GST, His peptide, FLAG, MBP, GFP, epitope tag, and any derivatives thereof. In some embodiments, the nucleic acid substrate comprises a plurality of nucleic acid polymers. In some embodiments, the reaction mixture comprises microfluidic volumes and each step of said method is performed in a microfluidic apparatus.

Another aspect of the invention provides for a method that comprises providing a reaction mixture comprising a nucleic acid substrate and a labeled enzyme in free solution, wherein said labeled enzyme comprises an affinity tag; performing an enzymatic reaction in free solution using said labeled enzyme and said nucleic acid substrate to produce a product nucleic acid in said reaction mixture; providing a solid substrate comprising a binding moiety for said affinity tag; binding said labeled enzyme to said solid substrate; and separating said reaction mixture from said bound labeled enzyme to generate a product mixture substantially depleted of the labeled enzyme. In some embodiments, the labeled enzyme is selected from a group consisting of a polymerase, a restriction enzyme, a ligase, a phosphatase, an exonuclease, and a kinase. In some embodiments, the product nucleic acid is not separated from said product mixture.

In some embodiments, the method further comprises performing the following steps at least once: performing an additional reaction on said product nucleic acid without separating said product nucleic acid from said product mixture, wherein said additional reaction is optionally performed in free solution with an additional labeled enzyme; and optionally separating said product mixture from said additional labeled enzyme.

In some embodiments, said nucleic acid substrate is a nucleic acid polymer, said labeled enzyme is a first labeled polymerase, wherein said reaction mixture further comprises free nucleotides and other reagents necessary for nucleic acid polymerization, and wherein said enzymatic reaction is synthesizing a first DNA strand complementary to the nucleic acid polymer; further comprising performing one or more of the following steps: i) providing a second labeled polymerase to the product mixture, wherein said second labeled polymerizing enzyme comprises a second affinity tag, ii) synthesizing a second DNA strand complementary to said first DNA strand to form a product DNA molecule in said product mixture, iii) providing a second solid substrate comprising a binding moiety for said second affinity tag, iv) binding said second labeled polymerase to said second solid substrate, and v) separating the product mixture from the bound second labeled polymerase; vi) providing an additional enzyme and processing said product DNA molecule using said additional enzyme; further providing an adapter nucleic acid and a ligase; ligating the adapter nucleic acid to said product DNA molecule to produce a ligated DNA molecule; and purifying said ligated DNA molecule.

In some embodiments, the first and second affinity tags are different or the same. In some embodiments, the method further comprises providing a sequencing instrument fluidically connected to said microfluidic apparatus and sequencing said ligated DNA molecule.

In some embodiments, the invention provides for a method for detecting one or more genetic sequences from a cell in a sample comprising: applying a cellular sample to a system that performs the steps of cell lysis, nucleic acid elution, library preparation, whole genome amplification and sequencing. The sample can be an environment sample. The sample can be a blood sample. The cell can be a microorganism. The microorganism can be a virus. The microorganism can be an RNA virus. The sample can comprise less than 10 ng, 9 ng, 8 ng, 7 ng, 6 ng, 5 ng, 4 ng, 3 ng, 2 ng, or 1 ng of DNA.

In some embodiments of the invention, the method comprises detecting an organism from a sample containing as few as any of 100, 50, 25, 15, 10 or 7 cells of the organism. The organism can be detected by sequencing nucleic acid from the cells.

In some embodiments, the method further comprises monitoring said one or more steps using a display. The display can be a touch-screen display. In some embodiments, the method does not necessitate additional human actions. In some embodiments, each reaction is performed in up to 10, 9, 8, 7, 6, 5 or 4 minutes. In some embodiments, the time from sample to sequence can be less than 500 minutes wherein the sequence comprises at least 1.5 Gigabases of sequence. The total time from sample to sequence can be less than 10, 9, 8, 7, 6, 5, 4, 3, 2, or 1 hr and with at least 60, 70, 80, or 83% read accuracy. In some embodiments, the sequencing comprises sequencing by synthesis in a flow cell, single molecule sequencing, sequencing on a bead, sequencing by detecting pH or ion fluxes, sequencing using a nanopore, sequencing using fiber optics, or sequencing in a microdroplet. In some embodiments, the method is performed to provide a diagnostic, select treatment, provide a prophylaxis, vaccine development, provide a response or detect bioterrorism.

In some embodiments, amplification comprises: inclusion of nucleotide analogs, using Phi29 DNA polymerase, using a polymerase having strand-displacement, rolling circle amplification, using a polymerase having proofreading activity, and/or using random hexamer priming. Amplification can amplify the nucleic acids by at least 1 million fold.

In some embodiments, the invention provides for a method and a system for performing said method, comprising introducing into an integrated system an impure nucleic acid-containing sample and operating the system to automatically purify the nucleic acid and generate sequence information on said nucleic acid. In some embodiments, at least part of the process is performed in a microfluidic environment. The sample can be cells or biomolecular macromolecules. The sample can be a forensic sample, an environmental sample or a medical sample. In some embodiments, purifying comprises lysing cells in the sample or capturing the nucleic acid on particles. The sample can have a non-microfluidic volume and purifying can comprise moving the nucleic acid into a microfluidic channel. In some embodiments, sequencing comprises real-time sequencing, pyrosequencing, sequencing by ligation, Sanger sequencing reversible dye-terminating sequencing, sequencing by synthesis, super pyrosequencing, sequencing by proton detection, nanopore detection, semiconductor sequencing or exonuclease-based sequencing.

In some embodiments, the method further comprises operating the system to chemically modify the nucleic acid to produce modified nucleic acid. The chemically modifying can comprise amplification, fractionation sequencing library preparation, whole genome amplification, or converting RNA into DNA. Sequencing library construction can comprise fractionation, end repair, A-tailing, adaptor ligation, size selection or normalization.

In some embodiments, the system can comprise reagents for library preparation including one or more of the following: a ligase, adaptors, barcodes, polymerase, restriction endonuclease. The system can comprise at least 1 microfluidic chamber comprising nucleic acid capture particles.

In some embodiments, the system can comprise (a) a nucleic acid purification assembly configured to receive an impure nucleic acid-containing sample and to purify nucleic acid from the impure sample; (b) a library preparation assembly configured to accept purified nucleic acid and to generate a nucleic acid library; (c) a normalization assembly configured to normalize the nucleic acid library to a concentration suitable for sequencing; (d) a reagent storage assembly configured to deliver reagents to the purification assembly, the library preparation assembly and the normalization assembly, and (e) a nucleic acid sequencer configured to accept and generate sequence information on the normalized nucleic acid.

The nucleic acid purification assembly can comprise a sample inlet adapted to received a cotton swab in fluidic communication with a cell lyser configured to receive cells from the sample inlet, lyse the cells and capture nucleic acid from the cells on capture particles, an output configured to transmit capture particles with captured nucleic acid to the library preparation assembly, and reagent inputs configured to transmit reagents from the reagent storage assembly into the DNA purification assembly and optionally wherein fluids are transmitted in the nucleic acid purification assembly through at least one mesofluidic or microfluidic channel.

The library preparation assembly can comprise a plurality of reaction chambers, wherein each reaction chamber is in fluidic communication with one of a plurality of inlet ports, each inlet port being configured to transmit purified nucleic acid from the nucleic acid purification assembly, and each reaction chamber is in fluidic communication with a reagent port configured to transmit reagent from the reagent assembly and optionally wherein fluids are transmitted in the library preparation assembly through at least one mesofluidic or microfluidic channel.

The normalization assembly can perform normalization in fluidic communication with normalization inlets, which are configured to transmit fluid from the nucleic acid library assembly, a detection subassembly in fluid communication with the normalization chambers configured to detect analyte in a solution transported from the normalization chambers, and a library delivery subassembly, in fluidic communication with the normalization chambers and configured to deliver a normalized sample to a receiving port of the sequencer and optionally wherein fluids are transmitted in the normalization assembly through at least one mesofluidic or microfluidic channel.

In some embodiments, the invention provides for a method comprising: a) in a microfluidic flow path, performing a first chemical reaction on a biomolecular analyte to produce a first product, and purifying the first product with capture particles; and b) without removing the first product from the microfluidic flow path, performing a second chemical reaction on a the first product to produce a second product and purifying the second product with capture particles. In some embodiments, the method further comprises, without removing an Nth product from the microfluidic flow path, performing at least one step subsequent to step (b) wherein each subsequent step comprises performing an Nth chemical reaction on an (N−1)th product to produce an Nth product, and purifying the Nth product with capture beads. The chemical reactions can be enzymatic reactions. The chemical reactions can be at least one of nucleic acid end repair, A-tailing, adaptor ligation, reverse transcription or double stranded DNA synthesis. The microfluidic flow path can comprise valves or chambers.

In some embodiments, the invention comprises a microfluidic chip comprising a library construction module and at least one of an amplification or a sequencing module. The microfluidic chip can comprise a flow cell. The flow cell can comprise a plurality of wells. The flow cell can comprise a weir. In some embodiments, the invention further comprising a plurality of a first double-stranded oligonucleotide bound to a solid substrate and a plurality of a second double-stranded oligonucleotide bound to said solid substrate. The first double-stranded oligonucleotide can comprise a blunt end. The second double-stranded oligonucleotide can comprise a single-base overhang. The single-base overhang can be a T overhang. The solid substrate can be the surface of a chamber, channel, or flow cell. The solid substrate can be a particle.

In some embodiments, the invention comprises a method for simultaneously performing library construction and amplification comprising: providing a nucleic acid sample and a plurality of a first double-stranded oligonucleotide bound to a solid substrate and a plurality of a second double-stranded oligonucleotide bound to said solid substrate; performing a first ligation step that ligates said nucleic acid sample to one of the plurality of said first double-stranded oligonucleotide; performing a second ligation step that ligates said nucleic acid sample to one of the plurality of said second double-stranded oligonucleotide; and amplifying said nucleic acid sample using a strand of said plurality of first and second double-stranded oligonucleotides as primers. In some embodiments, the method further comprises treating the pluralities of first and second double-stranded oligonucleotides such that a portion of said pluralities of first and second double-stranded oligonucleotides not ligated to said nucleic acid sample are modified to form single-stranded oligonucleotides bound to said solid substrate; and wherein said amplifying uses said single-stranded oligonucleotides as primers. In some embodiments, the method further comprises performing an end-repair reaction on said nucleic acid sample to provide at least one blunt end on said nucleic acid sample, and where said first ligation step ligates the blunt end of said nucleic acid sample to the blunt end of said first double-stranded oligonucleotide. In some embodiments, the method further comprises performing a single nucleotide extension on said nucleic acid sample to provide at least one single-base overhang, and where said second ligation step ligates said single-base overhang of said nucleic acid sample to the single base overhang of the second double-stranded nucleotide. In some embodiments, said single nucleotide extension is an A-tailing step and said double-stranded nucleotide comprises a T overhang.

In some embodiments, the method comprises a) providing a substrate having attached thereto first double stranded oligonucleotides, each having a blunt end and optionally at least some of which also have blocked ends, and second double stranded oligonucleotides, each having an end comprising an overhang, wherein only one strand of each of the first oligonucleotides and the second oligonucleotides is attached to the substrate and only at the 5' end; b) contacting the attached oligonucleotides with target nucleic acids, each of the target nucleic acids having a first blunt end and a second end, and performing a ligation reaction that ligates a blunt end of one of the target nucleic acids with a blunt end of the first oligonucleotide; c) modifying the second end of the ligated target nucleic acids and performing a ligation reaction that ligates the second end of target nucleic acid to the end of the second oligonucleotide; d) optionally, unblocking the blocked first oligonucleotides; e) denaturing double stranded nucleic acid molecules attached to the substrate and removing unbound polynucleotides; f) performing bridge PCR on nucleic acids attached to the surface using attached unligated first oligonucleotides as extension primers for nucleic acids attached to second oligonucleotides, and using unligated attached second oligonucleotides as extension primers for nucleic acids attached to first oligonucleotides.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION OF THE INVENTION

Figure 1:
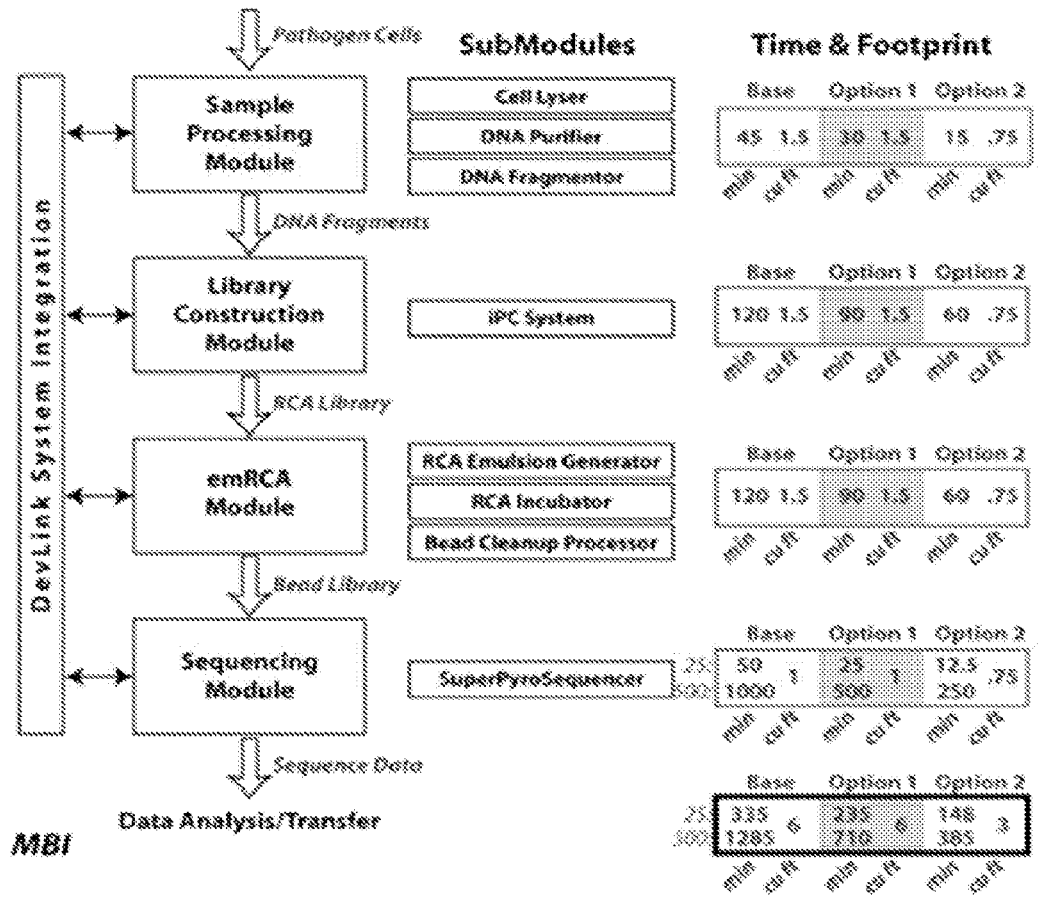
FIG. 1 shows a schematic of an exemplary system for performing sequencing on a sample.

The invention provides for systems, devices, methods, and kits for performing integrated sequences of biochemical reactions followed by product isolation. The invention may be used for producing nucleic acid sequencing data from a variety of samples, including whole-cell input samples, using high-throughput sequencing-by-synthesis. The nucleic acid to be sequenced can be DNA or RNA. The systems, devices, and methods can be fully automated by control software. The system is no more than about 3, no more than about 6, or no more than about 10 cubic feet and can generate sequence coverage from as low as about or less than 10 cells per sample with short sequence data (25 bases reads/6.25M bases) in no more than about 3 hours and long reads (500 bases/250 Mbases) in no more than about 7 hours. In some embodiments, the system can generate sequence coverage from less than 10 cells per 1 mL sample. The systems and methods can be scalable in throughput to at least about 10 Gigabases of sequence. The systems and methods can allow for rapid sequencing of samples and detection of genetically modified bioagents and emerging pathogens. The system can be a miniaturized deployable system that allows for mobile analysis. The system can be ruggedized to withstand travel or field use.

The system can comprise one or more integrated and fluidically connected modules, including a sample processing module, a library construction module, a normalization module, an amplification module, a sequencing module, and a computer module. The amplification module can be for any type of amplification, including emulsion PCR, rolling circle PCR, and bridge amplification. The modules can comprise microfluidic or mesofluidic components. In some embodiments, the modules do not contain microfluidic or mesofluidic components. The modules can comprise a linear, i.e., un-branched array of chambers, each optionally separated by a valve. The chambers may optionally comprise valves, such as diaphragm valves. When the chambers comprise valves, the valve chambers on the diaphragm valves can function as reaction chambers and/or capture chambers. The array typically comprises at least five chambers or diaphragm valves fluidically connected in a series. The first and last valves in series are connected to ports through which samples, solutions or reagents can be introduced into the array. The array may be connected to multiple ports for addition or removal of reagents and products from the array. In certain embodiments, the first and last valves in series are each connected to a bus or rail into which a plurality of ports feed. The array may be connected to reagent reservoirs, other modules or to other arrays. Multiple arrays may be arranged in parallel and connected to the same set of ports.

Systems and Devices for Integrated Analysis

In some embodiments, the invention provides for systems and devices for integrated analysis of samples. The systems and devices can perform the integrated analysis in an automated manner. In some cases, the systems and devices are fully automated and do not require user intervention after a sample is loaded and/or user input of sample conditions and analysis parameters. The system can receive a variety of sample types, as described herein. The analysis performed by the system can include sequencing nucleic acids in the sample. In some embodiments, the sequencing of nucleic acids can allow for the detection of genetic modifications. In some embodiments the analysis system can perform a separation.

The system can include one or more integrated modules. In some embodiments of the invention, the system includes a sample processing module, a library construction module, an amplification module, a sequencing module, and a computer module. The modules can be electronically integrated into a system by a computer module that can control and automate each of the integrated modules. The computer module can be a single computer module. The modules can be physically integrated into a system by the connections of each module to each other, including fluidic and electronic connections. In one embodiment of the invention, the integrated system includes a sample processing module, a library construction module, a normalization module, an amplification module, and a sequencing module that are each fluidically connected to one another and are each electrically connected to a computer module. The sample processing module, the library construction module, the normalization module the amplification module, and the sequencing module can be mounted on a platform. In some embodiments, the sample processing module, the library construction module, and, the normalization module can be contained on a cartridge, such as a disposable cartridge. In some embodiments, multiple copies of a module can be provided. As one example, 12 single sample processing modules can be connected to a library construction module configured to simultaneously prepare 12 libraries from samples. Any module can be a microfluidic module, or can contain no microfluidic components.

A schematic of an exemplary system is shown in FIG. 1. The system can include a sample processing module, a library construction or preparation module, an emulsion rolling circle amplification (emRCA) module, and a sequencing module that are each controlled and/or automated by a computer (shown as DevLink System Integration). Each module can have submodules, as shown in FIG. 1, that are configured to perform one or more steps. The sample processing module can be configured to receive a sample. As shown in FIG. 1, the sample processing module can prepare DNA fragments from a sample comprising pathogen cells. The library construction module can prepare a library of circularized nucleic acid fragments. The sequencing module can produce sequence data from the bead library. The emRCA module is used generically to represent an amplification module which can be emRCA, an emulsion PCR module, a polony module, a branched DNA module, a bridge amplification module, a rolling circle PCR module, a real-time PCR module, an amplification by ligation module, a digital amplification module or any other module that is suitable to amplify the nucleic acid as needed.

Figure 24:
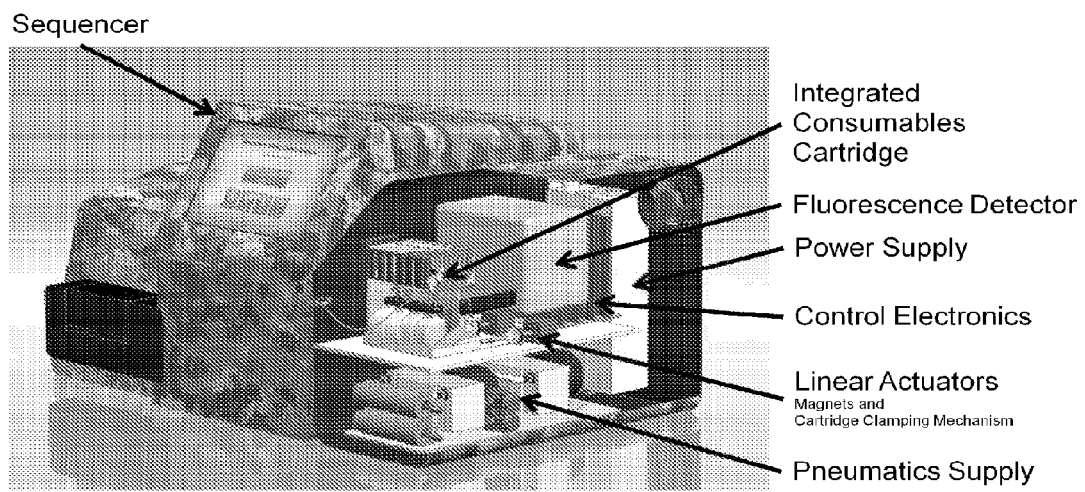
FIG. 24 shows an exemplary embodiment of the integrated sample to sequence system.

Another exemplary system is shown in FIG. 24. The integrated sample to sequence system contains an integrated cartridge for sample processing, a sequencer, various detectors, and devices for controlling the various components of the system. The integrated consumables cartridge can include reagents necessary for preparation of nucleic acids for sequencing from a raw sample. Detectors within the device can be used for sequencing; to measure sample quality, such as sequencing library concentration; or can be used to monitor the automated processes, such as detecting the time of transfer from one module to another. For example, in the depicted system, moving the target nucleic acids from the integrated consumables cartridge to the sequencer is carried out through capillary or other tubing. In some embodiments, the relatively long distance can make it difficult to determine the exact time when the target nucleic acids are input into the sequencer. A sensor can be placed at the end of the capillary tubing in the sequencer, which will allow the integrated system to determine when the prepared sample has reached the sequencer and can be sequenced. In another embodiment, the prepared sample can be moved to a reservoir in the sequencing without the necessity of a sensor or precision in control of the rate of movement of the sample. Once the raw sample is placed into the system, no additional input from the user is required to generate sequence information.

Figure 2:
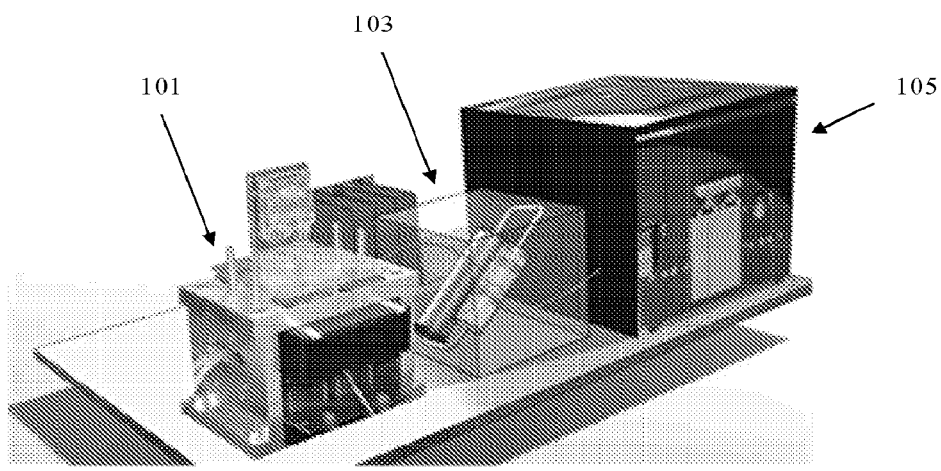
FIG. 2 shows a diagram of an integrated system for forming sequencing on a sample.
Figure 3:
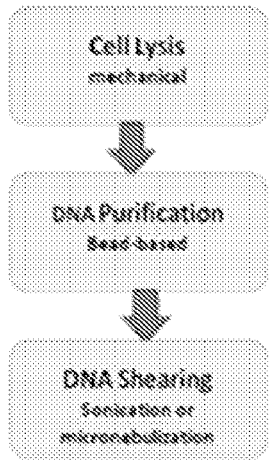
FIG. 3 shows a schematic of steps that can be performed within a sample processing module.

One or more of the sample processing module, library construction module, emRCA module, normalization module and sequencing module can be integrated into a system, where each module is fluidically connected to each other and each module is controlled and/or automated by a computer or computer logic. In some embodiments, the modules can be connected nonfluidically, such as by a device that transfers aliquots of sample or product from one module to another, such as by pipetting. One or more of the sample processing module, library construction module, cmRCA module, normalization module and sequencing module can be integrated into a single system, where each module is fluidically connected to each other and each module is controlled and/or automated by a single computer or a single computer logic. A computer can be integrated with the system as a computer module. The integrated modules may be mounted on a platform, a single platform, or one or more platforms. An example of integrated modules is shown in FIG. 2. FIG. 2 shows a combined sample processing module and library construction module (101), an emRCA module (103), and a sequencing module (105).

The one or more modules of the system configured to receive a sample and produce sequencing results can have a volume of about or no more than any of 1, 2, 2.5, 3, 4, 4.5, 5, 6, 6.5, 7, 8, 9, 10, or 100 cubic feet. The one or more modules can be selected from the group consisting of a sample processing module, a library construction module, an amplification module, a sequencing module, and a computer module. The modules of the system can be (a) a first module, which comprises a sample processing module, a library construction module, and an emRCA module, and (b) a second module, which comprises a sequencing module. In some embodiments, a computer is not integrated with the system and/or is not included in the volume of the modules.

The one or more modules can be configured to receive a sample and produce sequencing results, and the integrated ISS system can return sequencing results in about or no more than any of 0.1, 0.3, 0.5, 1, 2, 2.5, 3, 4, 5, 6, 6.5, 7, 8, 9, 10, 11, 12, 13, 14, 15, 16, 17, 18, 19, 20, 21, 22, 23, 24, 36, or 48 hours. In some embodiments, a module can simultaneously process at least 1, at least 2, at least 3, at least 4, at least 5, at least 6, at least 7, at least 8, at least 9, at least 10, at least 12, at least 24, at least 48, at least 96, at least 384, or at least 1000 samples. The sequencing results can include sequencing information on the sample for about or greater than about 1 million, 100 million, 125 million 250 million, 1 billion, 1.5 billion, 3 billion, 10 billion, or 100 billion bases. In some embodiments, the system can process reads of about or more than any of 5, 25, 50, 100, 150, 200, 250, 300, 350, 500, 1000, 2000, 5000, 10 thousand, 100 thousand, 1 million, 10 million, or 100 million bases. In some embodiments, the system can process about or more than any of 1, 1 thousand, 10 thousand, 500 thousand, 750 thousand, 1 million, 2 million, 3 million, 4 million, 5 million, 6 million, or 10 million reads in a single run. In some embodiments, the system can generate sequence coverage using a sample containing less than any of 5, 10, 25, 50, 100, 250, 500, or 1000 femtograms of DNA. In some embodiments, the system can generate sequence coverage from about, less than, or more than 1, 5, 10, 15, 20, 25, 30, 35, 40, 50, 100, 200, 500, 1000, or 2000 target cells, viral particles, or molecules per input sample. In some embodiments, the input samples can contain mixed populations of cells, viral particles, and/or molecules, and can also contain contaminants, such as organic and inorganic molecules or other substances that may be found in forensic or environmental samples. In some embodiments, the system or modules of the system can simultaneously process or sequence multiple samples in parallel. In some embodiments, the system or modules can simultaneously process at least about 2, 3, 4, 5, 6, 7, 8, 9, 10, 11, 12, 24, 48, 96, 192, or 384 samples.

A system comprising one or more modules configured to receive a sample and produce sequencing results can produce the sequencing results without manual assistance and/or in an automated fashion. In some embodiments, the system performs each step in an automated fashion based on pre-set instructions. The system can move the sample, or portions of the sample, reagents, and products in an automated fashion based on pre-set instructions. The pre-set instructions can be programmed, selected, or inputted by a user and/or by a manufacturer, or any combination thereof.

The system can be configured to detect pathogens, genetic modifications, gene sequences, and/or obtain sequencing results on samples containing as few as 1000, as few as 100, as few as 10 bacteria, or as few as 1 bacteria in a sample. In some embodiments, the system can detect at least 1, 10, 100, 1,000, 10,000, or 100,000 different microorganisms in a sample. The detection limit can be as low as 1, 10, 100, or 1000 cells in a sample. The sample volume can be 10, 100, 1000, or 10000 microliters. The low detection limit can be achieved using the devices and methods described herein that allow for efficient and/or high yield cell lysis, DNA recovery, DNA shearing, library construction, amplification, and sequencing steps.

Other systems and methods for integrated analysis are described in Farias-Hesson, Semi-Automated Library Preparation for High-Throughput DNA Sequencing Platforms, Journal of Biomedicine and Biotechnology Volume, 2010 and U.S. Pat. Nos. 7,749,737 and 7,704,735, which are each incorporated by reference in their entirety.

Figure 23:
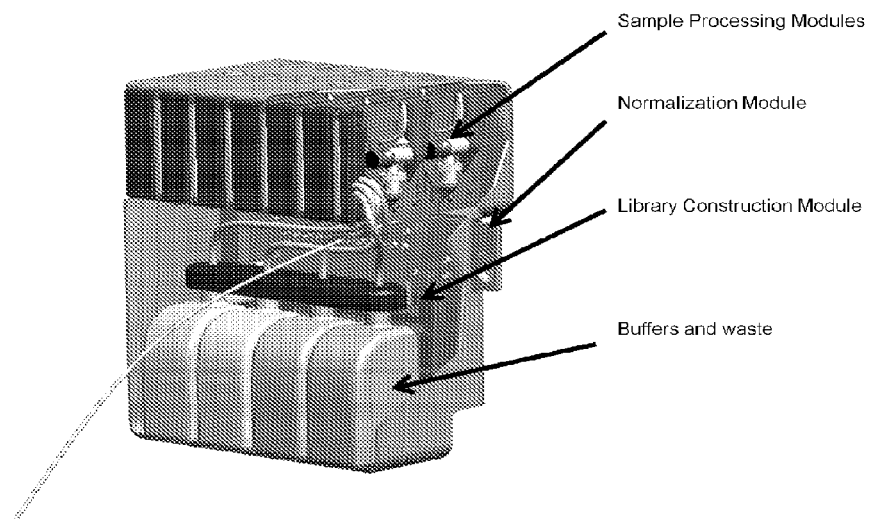
FIG. 23 shows an integrated cartridge comprising a sample processing module, a library construction module, a normalization module, and reagent and waste reservoirs.

In an exemplary embodiment, the ISS system of the invention can generate 1.5 Gigabases per run, enabling deep sequencing from a variety of sample types, and facilitating complete metagenomic analyses, including the sequencing of multiple entire microbial genomes in depth. In some embodiments, the system can process and sequence samples comprising gram positive or gram negative bacteria. Consumable requirements can be kept at a minimum. In some embodiments, a single-use disposable Integrated Consumable Cartridge can comprise multiple modules of the system as depicted in FIG. 23. For example, the Integrated Consumable Cartridge can integrate the Sample Processing module and the Library Construction module into a single cartridge operated by the ISS System. The cartridge can input raw samples and output a pooled normalized library. The cartridge can also include shared reagents or other resources for use by the integrated modules. In some embodiments, the reagents used in the invention or located in an Integrated Consumable Cartridge may be stabilized, such as by lyophilization; freeze drying; adding stabilizing molecules such as osmoprotectants, glycine betaine, potassium glutamate, trehalose, lactose, maltose, polymeric sugars such as dextrans or Ficoll, or organic molecules such as polyethylene glycol or polyvinylpyrrolidine; or any combinations thereof.

In some embodiments, the invention can incorporate a reverse transcription reaction. In embodiments where the sample contains target RNA molecules, RNA degradation can be minimized in the lysate by using proprietary or non-proprietary stabilization reagents or chaotropic salts. Processing times to perform the reactions can be minimized by enhancing the full volume chemistry with optimal enzyme concentrations, minimizing reaction volumes (consistent with system performance), and maximizing the size of pumps in the modules to decrease times for mixing and pumping. Modifications facilitating full system integration can be designed and integrated into the module.

Modules can be fluidically connected via microfluidic or macrofluidic connections. In some embodiments, modules are connected through a flexible connection, such as via tubing or capillary tubes. In some embodiments, microfluidic modules are fabricated into one or more microfluidic chips and fluidically connected using microfluidic channels, chamber, or other microfabricated structures. In some embodiments, modules can be linked by movable microfluidic structures such as a sliding linear valve as described in U.S. Pat. Nos. 6,870,185 and 7,244,961, or sliding rotary valves as described in U.S. Pat. No. 6,190,616. In short, such microfluidic devices can incorporate a sliding or rotating component that can move a linking microfluidic structure into or out of fluidic communication with one or more modules.

In some embodiments, modules are removable. In some embodiments, modules are disposable. One or more modules can be in a disposable cartridge. One or more modules can be in a reusable cartridge. In some embodiments, a system of the invention comprises multiple copies of one or more modules. In the cartridge shown in FIG. 23, twelve sample processing modules are fluidically integrated with a library construction module, a normalization module, and buffer and waste reservoirs. Samples can be input into the sample processing modules and processed in parallel, such as by cell lysis, nucleic acid purification, and nucleic acid fragmentation. The integrated cartridge can move the fragmented nucleic acids from the sample processing modules to the library construction module, which is configured to process at least twelve samples simultaneously. In one embodiment, the fragmented nucleic acids are passed from the sample processing module to the library module through the fluidic channels on the normalization module. The library construction module can then modify the fragmented nucleic acids to generate a sequencing library, which can be passed to the normalization module. The normalization module can determine the concentration of the sequencing library, and optionally adjust the sequencing library concentration or pool multiple sequencing libraries into one sample. The integrated cartridge can then transfer the normalized sequencing library to the sample inlet of a sequencing module, for example through a capillary tube. Movement within the cartridge, or from the cartridge to the sequencing module, can be controlled by pumps or valves, including microfluidic pumps. In some embodiments, a sensor may be placed next to or near the end of the capillary tube to detect when the sequencing library reaches the sequencing module.

Module Components and Assembly

Figure 12:
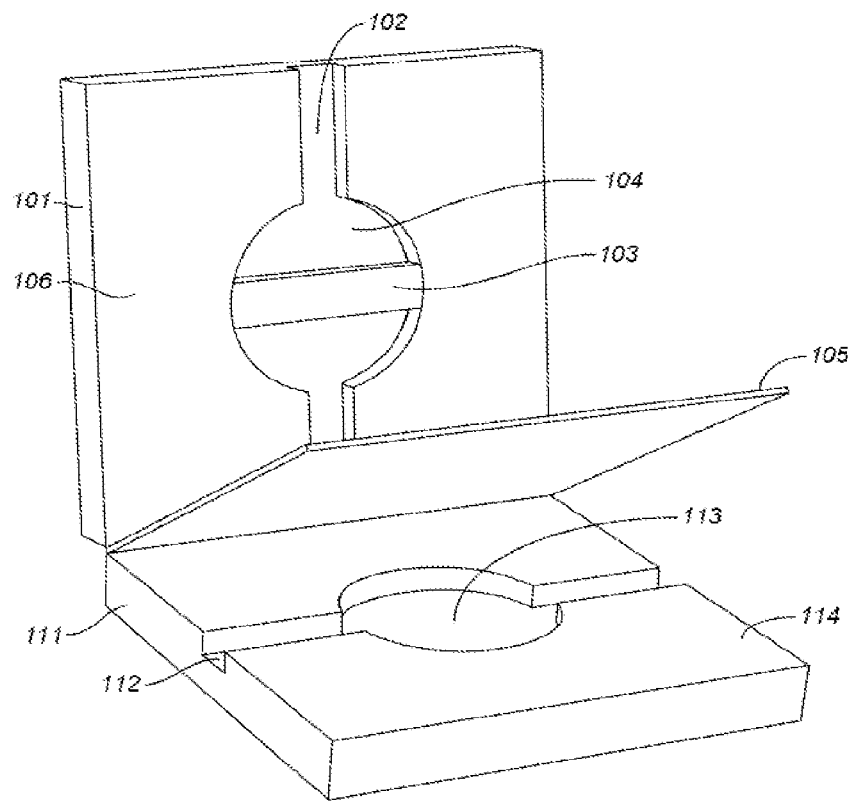
FIG. 12 shows a clamshell view of one embodiment of a diaphragm valve of this invention.
Figure 14:
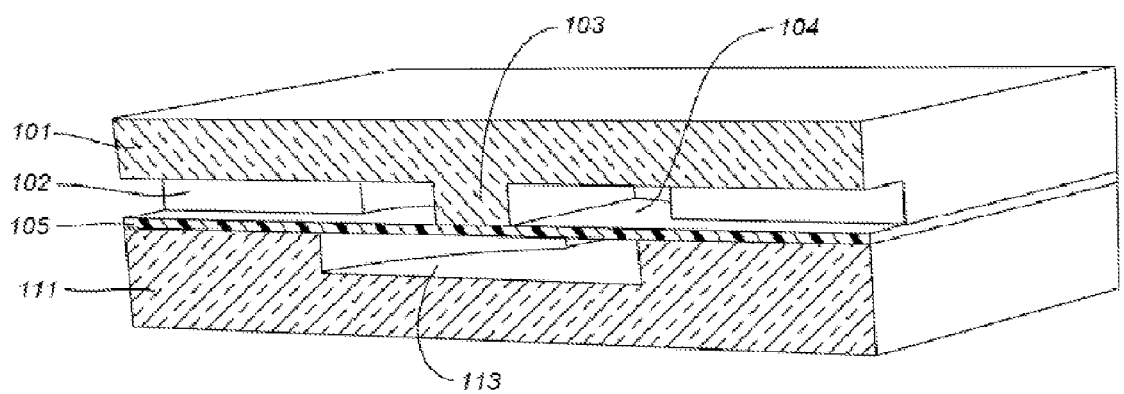
FIG. 14 shows a cross-section of a "three layer" diaphragm valve in a closed configuration.
Figure 15:
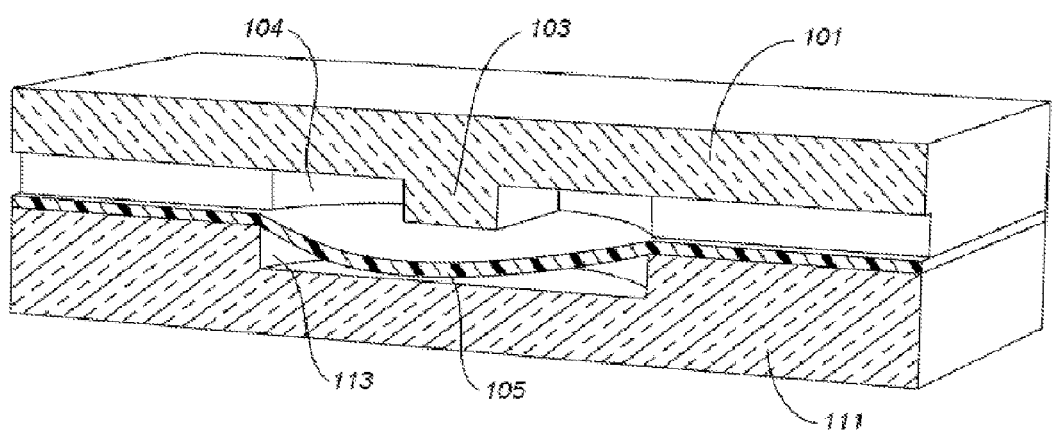
FIG. 15 shows a cross-section of a "three layer" diaphragm valve in an open configuration

Modules of the invention can comprise microfluidic chambers, channels, or valves. A microfluidic chamber of the invention can hold a volume of about, no more than any of about, or more than any of about 0.005, 0.01, 0.05, 0.1, 0.2, 0.3, 0.4, 0.5, 0.6, 0.7, 0.8, 0.9, 1, 1.25, 1.5, 2, 2.5, 3, 5, 7, or 10 µL. The chamber can be enclosed or open to the environment. The chamber can be fluidically connected to downstream modules and submodules by one or more channels, tubes, or flexible connections. The channels can be microfluidic channels. The channels, or any other channel described herein, can comprise one or more valves, such as pneumatically actuated valves. An example of a pneumatically actuated valve, e.g., a diaphragm valve, is shown in FIG. 12, FIG. 14, and FIG. 15. In some embodiments, the pneumatically actuated valve can be constructed using three layers of material, a top glass wafer, a bottom glass wafer, and an elastomeric film sandwiched between the top and bottom glass wafers. The elastomeric film can be PDMS. The top and bottom glass wafers can have features designed to create channels for passage of fluid, seats for contacting the elastomeric film when the valve is in a closed state, and ports for application of a pneumatic fluid that can control the position of the elastomeric film. Other materials, such as plastics, can be used in place of glass, and the elastomeric film can be replaced with other materials, as are described in U.S. patent application Ser. No. 12/949,623. Other forms of valves and diaphragm valves, including two-layer valves, are also envisioned, such as are described in U.S. Patent Publication 2010/0303687, U.S. Pat. No. 7,258,744, and in Unger et al. (2000) Science 288:113-116.

Diaphragm Valves

A diaphragm valve uses a diaphragm to open or close a fluidic path between fluidic conduits. A diaphragm valve typically comprises a valve body having a valve inlet and a valve outlet that communicate with the fluidic conduits entering and exiting the valve. The body also has a diaphragm disposed within the body and configured to move on or off a valve seat to close or open the valve. In some embodiments, the diaphragm does not fully contact the valve seat when fully actuated. The valve body also defines a valve chamber, which is a space created between the diaphragm and the valve seat when the valve is open, and a valve relief, which is a space into which the diaphragm can deflect away from the valve seat. When the valve is open, a continuous fluid path is formed through which the valve inlet is in fluid communication with the valve outlet.

Microfluidic devices with diaphragm valves that control fluid flow have been described in U.S. Pat. No. 7,445,926 (Mathies et al.), U.S. Pat. No. 7,745,207 (Jovanovich et al.), U.S. Pat. No. 7,766,033 (Mathies et al.), and U.S. Pat. No. 7,799,553 (Mathies et al.); U.S. Patent Publication Nos. 2007/0248958 (Jovanovich et al.), 2009-0253181 (Vangbo et al.), 2010/0165784 (Jovanovich et al.), 2010/0285975 (Mathies et al.) and 2010-0303687 (Blaga et al.); PCT Publication Nos. WO 2008/115626 (Jovanovich et al.) and WO 2010/141921 (Vangbo et al.); PCT application PCT/US2010/40490 (Stern et al., filed Jun. 29, 2010); U.S. application Ser. No. 12/949,623 (Kobrin et al, filed Nov. 18, 2010); and U.S. provisional applications 61/330,154 (Eberhart et al., filed Apr. 30, 2010), 61/349,680 (Majlof et al., filed May 28, 2010) 61/375,758 (Jovanovich et al., filed Aug. 20, 2010) and 61/375,791 (Vangbo, filed Aug. 20, 2010).

In one embodiment, the diaphragm valves of this invention comprise three layers: A fluidics layer, an actuation layer and an elastic layer sandwiched between them. However, two-layer valves are also contemplated herein. The elastic layer is configured to cover at least a portion of the mating surfaces of the fluidics layer and the actuation layer that comprise valves. The fluidics layer and actuation layer typically are comprised of a material more rigid than the elastic layer, e.g. plastics, silicon, ceramics, or glass. Diaphragm valves of this invention are formed by functional elements in the three layers. A valve inlet and a valve outlet communicate with fluidic conduits in the fluidics layer to form a fluidic path. A valve inlet and a valve outlet comprise openings on the surface of the fluidics layer facing the elastic layer. The portion of the surface of the fluidics layer between the valve inlet in the valve outlet can function as a valve seat. The elastic layer provides one or more diaphragms. A diaphragm in a valve is actuatable to be positioned against or away from a valve seat, closing or opening the valve. An actuator to actuate the diaphragms is comprised, at least in part, in the actuation layer.

In one embodiment, the diaphragm valves of this invention comprise two layers: a fluidics layer and an actuation layer. The fluidics layer, the actuation layer, or both layers may comprise an elastic material, which further serves as the diaphragm of the valve.

The face of a fluidics layer or an actuation layer that faces the elastic layer in a sandwich format is referred to as a mating face. A mating face typically will have functional elements such as conduits, valves and chambers that are exposed to and are covered by the elastic layer. The surfaces of such functional elements are referred to as functional surfaces. When mated together and assembled into a sandwich, the portions of the mating faces that touch the elastic layer are referred to as sealing surfaces. Sealing surfaces may be bonded to or pressed against the elastic layer to seal the device against leaks.

Mating faces of the fluidics layer and the actuation layer can be substantially planar, flat or smooth. Fluidic conduits and actuation conduits may be formed in the surface of the fluidics or actuation layers as furrows, dimples, cups, open channels, grooves, trenches, indentations, impressions and the like. Conduits or passages can take any shape appropriate to their function. This includes, for example, channels having semi-circular, circular, rectangular, oblong or polygonal cross sections. Valves, reservoirs and chambers can be made having dimensions that are larger than channels to which they are connected. Chambers can have walls assuming circular or other shapes. Areas in which a conduit becomes deeper or less deep than a connecting passage can be included to change the speed of fluid flow. Channels have a width of at least any of 0.01, 0.1, 1, 20, 50, 100, 150, 200 or 300 microns or no more than any of 200, 100, 50, or 20 microns. Channels can have a depth of at least any of 0.01, 0.1, 1, 10, 50, 100, or 150 microns, or no more than any of 200, 100, 50 or 20 microns. A channel can have side walls that are parallel to each other or a top and bottom that are parallel to each other. A channel can comprise regions with different cross sectional areas or shapes. In some embodiments the microchannels have the same width and depth. In other embodiments the microchannels have different widths and depths. In another embodiment a microchannel has a width equal to or larger than the largest analyte (such as the largest cell) separated from the sample. In another embodiment the channels are smaller than the largest analyte (such as a cell or bead). This is a way of collecting materials, e.g., collecting particles on a constriction, a dam or a weir.

A diaphragm valve closes when the diaphragm sits against a valve seat, thereby preventing fluid flow between the valve inlet and the valve outlet. When the diaphragm is off the valve seat, it creates a fluidic chamber or passage through which fluid may flow. A fluidic conduit is then in fluid communication with the valve chamber through the valve ports. The valve may be configured so that under ambient conditions (i.e., no external application of positive or negative pressure) the diaphragm naturally sits on the valve seat, thus closing the valve, and is deformed away from the seat to open the valve by application of positive or negative pressure relative to ambient (a so-called "normally closed" valve). The valve also may be configured so that under ambient conditions (i.e., no external application of positive or negative pressure) the diaphragm naturally does not sit on the seat and is deformed toward the seat to close the valve by application of positive or negative pressure relative to ambient (a so-called "normally open" valve). In this case, application of positive pressure to the elastic layer from the actuation conduit will push the elastic layer onto or near the valve seat, closing the valve. Thus, the diaphragm is in operative proximity to the valve seat and configured to be actuatable to contact the valve seat or to be out of contact with the valve seat.

Positive and/or negative pressure exerted against the diaphragm from the actuation layer serves to close or open diaphragm valves. Negative pressure or vacuum exerted by the actuation conduit deflects the diaphragm into the valve relief, resulting in an open valve. A sufficiently high positive pressure exerted by the actuation conduit deflects the diaphragm toward the valve seat, causing of the valve to close. And intermediate pressure exerted by the actuation conduit can prevent liquids or gases in a fluidic conduit from leaking across the diaphragm into the actuation conduit.

A clamshell view of a three layer diaphragm valve is shown in FIG. 12. A cross-sectional view of a closed diaphragm valve is shown in FIG. 14 and a cross-sectional view of an open diaphragm valve is shown in FIG. 15. A fluidics layer 101 comprises a fluid conduit comprising a fluidic channel 102 interrupted by a valve seat 103 which, in this case, is flush with the surface of the fluidic layer. In this embodiment, fluidic channel opens into a fluidics valve body 104. One face of the fluidics layer contacts the elastic layer 105 in the assembled device. This face comprises sealing surfaces 106, to which the elastic layer can be sealed, and exposed surfaces of the functional components—fluidic conduit including the valve seat. An actuation layer 111, comprises an actuation conduit comprising an actuation channel 112 and an actuation valve body 113 disposed opposite the valve seat. The actuation layer also comprises a face that contacts the elastic layer in the assembled device that has sealing surfaces 114 and exposed surfaces (surfaces of 112 and 113) of functional elements. In some embodiments, the top or bottom glass wafers may be replaced with other materials, such as silicon, metals, plastics, or elastomers.

This invention contemplates several configurations for a valve seat. In one embodiment, the valve seat is configured as an interruption in a fluidic channel disposed along the mating face of a fluidics layer. In this case, the channels are covered over by the elastic layer. The termini of the channels that are coincident with the valve recess function as valve inlet and valve outlet.

In some embodiments of the invention, a diaphragm valve does not have a valve seat, and fluid flow through the fluidic channel is not completely obstructed under application of positive or negative pressure. This type of valve is useful as a fluid reservoir and as a pumping chamber and can be referred to as a pumping valve. In some embodiments, valves may be used as a chamber. The vacuum that can be applied include extremely high vacuum, medium vacuum, low vacuum, house vacuum, and pressures such as 5 psi, 10 psi, 15 psi, 25 psi, 30 psi, 40 psi, 45 psi, and 50 psi. In some embodiments, valves may be driven by pressure, including vapor or hydraulic pressure. Valves may be naturally open or naturally closed.

Figure 13:
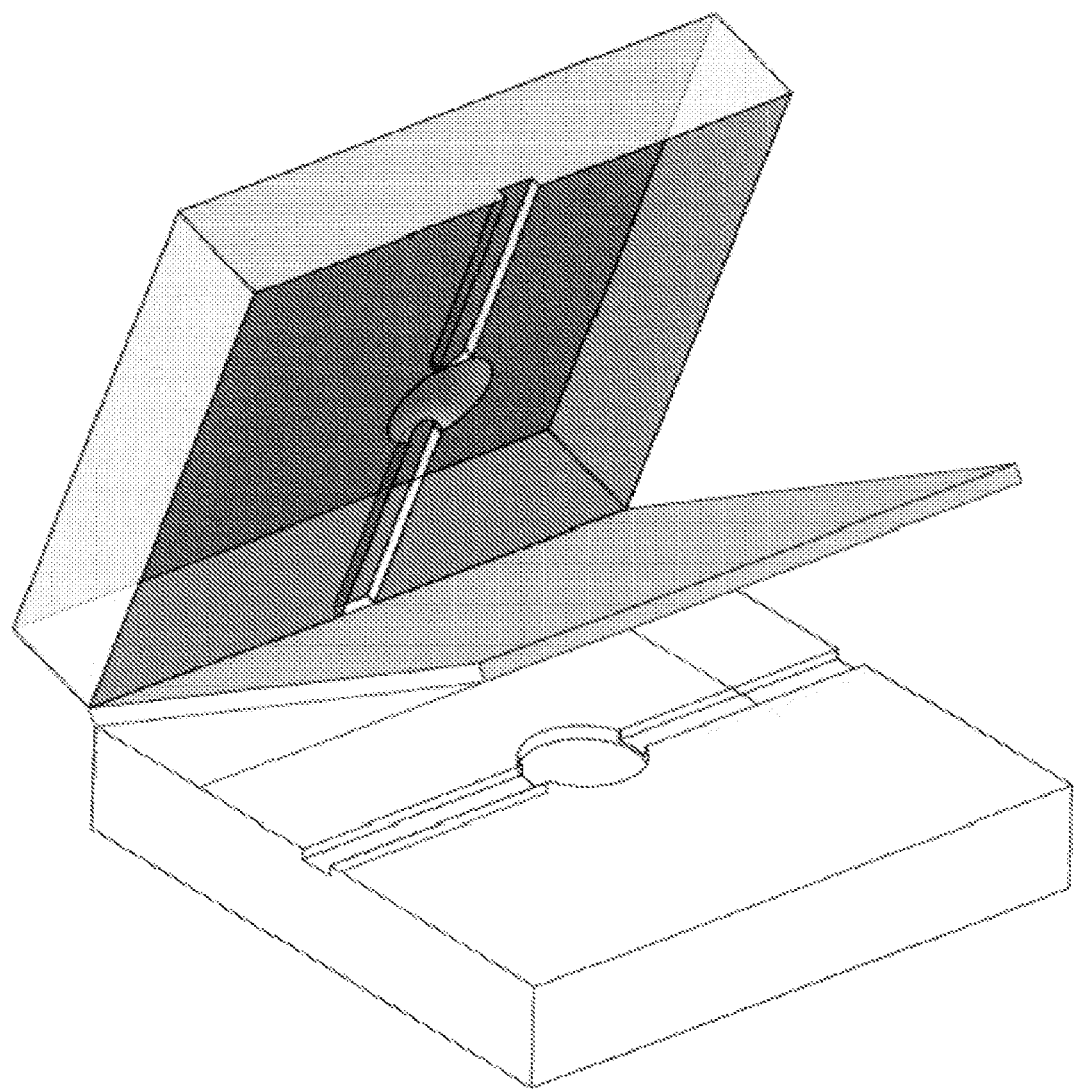
FIG. 13 shows a clamshell view of one embodiment of a domed diaphragm valve of this invention.

FIG. 13 depicts an embodiment of a normally open valve in which a surface of an interruption that would otherwise form a valve seat for a normally closed valve is recessed with respect to the surface of the fluidic layer bonded to the elastic layer. In this case, the valve seat will be raised with respect to the elastic layer. Positive pressure on the elastic layer pushes the elastic layer against the valve seat, closing the valve. Valve seats can be recessed with respect to the rest of the surface by about 25 microns to about 75 microns, e.g., about 50 microns, using, for example, ablation techniques.

In another embodiment of a normally open valve, the valve seat is not configured as an interruption in a fluidic conduit. Rather, it takes the form of a recess with respect to a surface of the fluidics layer that normally contacts the elastic layer, so that the elastic layer does not sit against the recessed surface without application of pressure on the elastic layer, e.g., through the actuation chamber. In this case, the valve may not have a discrete valve chamber in the fluidics layer that is separate from the valve seat. The valve seat can take a curved shape that is concave with respect to the surface of the fluidics layer, against which the elastic layer can conform.

In certain embodiments of a normally open valve, the concavity is recessed less than the channels to which it is connected. For example, the deepest part of the concavity can be about one-third to one-half the depth of the channel (e.g., 30 microns to 50 microns for the concavity versus 100 microns for the channel). For example, the elastic layer may be about 250 microns thick, the channels about 100 microns deep and the valve seat about 30 microns deep. The thinner the elastic layer, the deeper the concavity can be, because the elastic layer can conform to the concavity without excessive deformation. In certain embodiments the channels can enter partially into the concavity, for example forming a vault. In certain embodiments, the channels and concavity are formed by micromachining. The actuation layer can comprise a valve relief into which the diaphragm deflects for opening the valve.

Flow-through and in-line valves can include valves that are situated at intersections of greater than two, three, four, or more channels, which can be used as control valves to regulate reagent input in a module, such as to a linear array. Valve seats or other structures can be designed such that closure of the valve can prevent or reduce flow in one or more of the channels while allowing fluid to flow in one or more of the other channels. For example flow can be blocked along three of five channels, while flow can continue through two of the five channels. A flow-through valve can also be referred to as a T-valve, as described in WO 2008/115626 (Jovanovich et al.). See FIGS. 7 and 8. A plurality of flow-through valves can be arranged along a single channel to create a bus in which fluid flowing in the common channel can be diverted to one or more of the channels intersecting at each of the valves.

Diaphragm Pumps

In another embodiment pumps are provided. A pump typically comprises a closable inlet, a closable outlet and a pump head. The closeable inlet and outlet can, themselves, be diaphragm valves. The pump head can provide motive force for liquids in the pump. It can comprise a body divided by a diaphragm that defines a valve chamber and a valve relief. The pump head can be configured as a valve that has a valve seat and that close the fluidic channel. Alternatively, the pump head can have a valve chamber (or pump chamber) configured so that the diaphragm does not, in operation, close the fluidic passage completely or at all. For example, the pump chamber can be configured as a shape, such as a circular bore, to which the elastic layer, when pressurized, cannot completely conform to close the valve. In this embodiment, deforming the diaphragm into the valve relief increases a volume to accept fluid, and deforming the diaphragm into the valve/pump chamber pumps liquid out of the chamber. In this configuration, the position of the diaphragm alters the effective cross-section of the fluidic conduit and, thus, can regulate the speed of flow through the valve. A pump head that does not, in operation, completely seal is sometimes referred to as a "pumping valve."

Three diaphragm valves placed in a series can function as a diaphragm pump, e.g., a positive displacement pump. (See FIG. 7.) The middle valve can be a pumping valve. Positive displacement diaphragm pumps are self-priming and can be made by coordinating the operation of the three or more valves, and can create flow in either direction. A variety of flow rates can be achieved by the timing of the actuation sequence, diaphragm size, altering channel widths, and other on-device dimensions.

To operate a three-part diaphragm pump, a first valve is opened and a third valve is closed. Then, the second, or middle, valve is opened, drawing liquid through the first valve and into the chamber of the second valve. Then, the first valve is closed, the third valve is opened. Then, the second valve is closed, pumping liquid in the valve through the third valve. For example, moving the diaphragm into the valve relief creates an intake stroke that pulls fluid into the valve chamber when the valve inlet is open and the valve outlet is closed. Then, moving the diaphragm toward the valve seat creates a pump stroke that pushes the fluid out of the valve chamber when the valve inlet is closed and the valve outlet is open. Diaphragm pumps comprising more than three valves are also envisioned. For example, to operate a four-part diaphragm pump, a second valve is opened and a fourth valve is closed. Then, the second and third valves are opened, drawing liquid through the first valve and into the second and third valves. The first valve is then closed, and the fourth valve opened. Then the second valve is closed, pumping liquid in the valve through the third and into the fourth valve. The third valve can then optionally be closed to push the liquid in the third valve through the fourth valve. In another embodiment, a four-part diaphragm pump may be operated by sequentially operating the first three valves of the pump as a three-part valve, followed by operating the second, third, and fourth valves of the pump as a second three-part valve. Similar methods for operating diaphragm pumps comprising five or more parts are envisioned, and can be derived from the methods described herein by one of skill in the art.

Routers can similarly be formed from these valves and pumps. The routers can be formed using three or more valves each on a separate channel connecting to central diaphragm valve. A router also can be made by configuring three channels, each comprising a diaphragm pump, to meet in a common chamber, e.g., a pumping chamber. Bus structures can also be created that employ a series of at least two flow-through valves in which intersecting channels intersect the same flow-through channel.

Fluidics Layer

In one embodiment, one of the sublayers is configured as a fluidics manifold. The fluidics manifold can comprise one or more apertures that define a non-microfluidic volume and that traverses the manifold and connects with a channel on either side of the via layer. The fluidics manifold can be comprised of a rigid plastic. The via layer can be of a thin, substantially flat sheet of for example, plastic or glass.

The fluidics layer can comprise functional elements such as valve seats and chambers. The fluidics layer can comprise impediments to movement of objects in fluidic channels, such as weirs. Chambers can be used to store fluids or as locations at which chemical or biochemical reactions are carried out, e.g., reaction chambers. Chambers can also form a component of valves. The fluidics layer can be in thermal communication with a heat transfer element. The fluidics layer can be in communication with a source of magnetic force, which can be used to regulate movement of magnetically responsive particles in the device.

Elastic Layer

The elastic layer can be a smooth or flat, e.g., unsculpted, layer. Typically, a single monolithic piece of elastic material covers a surface of a fluidics layer and an actuation layer into which a plurality of functional elements, such as conduits, valves and chambers, are introduced. In a sandwich format, surfaces of the fluidics layer and actuation layer contact the elastic layer and are covered by it. A single elastic layer can provide diaphragms for a plurality of valves. In other embodiments, the elastic layer can be sculpted to create thinner or thicker regions. Such regions can provide useful volumes or have altered flexibility (thinner layers being more flexible). In some embodiments, the elastic layer can be incorporated into the actuation layer or fluidics layer.

Actuation Layer

The actuation layer can comprise a mating surface configured to mate with the fluidics layer across the elastic layer. The mating surface can be substantially flat or can comprise raised sealing rings which are raised above the mating surface. The actuation layer can comprise at least one or a plurality of actuation conduits, which can be fluidically connected with the valve relief and which can open elsewhere on the actuation layer. Positive or negative pressure can be transmitted from these openings or ports to the valve relief Actuation conduits can be configured along the mating face of the actuation layer or as internal channels in the actuation layer. For example, the actuation layer can be comprised of a plurality of sublayers into which the channels are introduced. Alternatively, they can traverse the actuation layer, for example as bores or apertures connecting one face of the actuation layer with the mating face. Channels can have a cross-section that is less than that of the valve relief, or can be configured as a strip having similar width as the valve relief to which it is connected. Actuation conduits can be configured to operate one or a plurality of valves. For example, a fluidics layer can comprise a plurality of fluidic circuits, each of which contains a valve, and a single actuation conduit can be in fluidic communication with the valves. In this configuration, action in the actuation conduit will be translated to all of the valves to which the conduit is connected, resulting in parallel operation.

Diaphragm valves in the devices of this invention can be actuated by a hydraulic actuator. In some embodiments, the actuator comprises a hydraulic conduit comprised at least in part or completely within the actuation layer; a translator; and an incompressible fluid contained the hydraulic conduit and in fluid communication with the translator and with the diaphragm. Translation of the translator transmits pressure (positive or negative) through the incompressible fluid to the diaphragm, actuating the diaphragm. More specifically, positive or negative pressure exerted on an incompressible fluid in an actuation conduit and in contact with the diaphragm moves the fluid against or away from the diaphragm, translating the pressure and actuating the diaphragm toward or away from the valve seat.

The actuator comprises elements involved in actuating the valve. These can include, for example, an incompressible fluid, the container which contains the incompressible liquid, and the translator, which translates or moves the incompressible fluid. The translator can comprise a translation surface that is in contact with the incompressible fluid. Movement of the translation surface exerts pressure on the incompressible fluid, moving it toward or away from the diaphragm of the valve. The translator further can comprise various elements for moving translation surface. This invention contemplates a variety of actuator formats.

The incompressible fluid that transmits pressure through the actuation conduits can be referred to as an actuant. The fluid can be any hydraulic fluid, including aqueous liquid or organic liquid, e.g., water, a perfluorinated liquid (e.g., Fluorinert), an oil (e.g., dioctyl sebacate (DOS) oil, monoplex DOS oil, silicon oil or hydraulic fluid oil) or automobile transmission fluid. Various compressible substances, including gases such as air, may also be used as an actuant. The pressure used to actuate the valves can be, for example, less than about +/−10 psig, less than about +/−15 psig, less than about +/−20 psig, less than about +/−25 psig, or greater than 25 psig (e.g., to close and open valves).

Monolithic Devices

In certain embodiments, the microfluidic devices of this invention are monolithic devices. In monolithic devices, a plurality of fluidic circuits are provided on a single substrate. In the case of devices comprising diaphragm valves, a monolithic device can comprise a single elastic layer functioning as a diaphragm for a plurality of valves. In certain embodiments, one actuation channel can operate a plurality of valves on a monolithic device. This allows parallel activation of many fluidic circuits. Monolithic devices can have dense arrays of microfluidic circuits. These circuits function with high reliability, in part because the channels in each circuit are fabricated simultaneously on a single substrate, rather than being made independently and assembled together. In other embodiments, an actuation conduit can control actuation of a single valve. For example, the actuation conduit can traverse the actuation layer from the actuation surface to the other side.

The fluidic circuits and actuation circuits of these devices can be densely packed. A circuit comprises an open or closed conduit. In certain embodiments, the device can comprise at least 1 fluidic circuit per 1000 mm$^2$, at least 10 fluidic circuits per 1000 mm$^2$ or at least 50 fluidic circuits per 1000 mm$^2$. Alternatively, the device can comprise at least 1 mm of channel length per 10 mm$^2$ area, at least 10 mm of channel length per 10 mm$^2$ or at least 20 mm channel length per 10 mm$^2$. Alternatively, the device can comprise valves at a density of at least 1 valve per cm$^2$, at least 4 valves per cm$^2$, or at least 10 valves per cm$^2$. Alternatively, the device can comprise features, such as channels, that are no more than 5 mm apart edge-to-edge, no more than 1 mm apart, no more than 500 microns apart or no more than 250 microns apart.

In other embodiments, the device can comprise at most 1 fluidic circuit per 1000 mm$^2$, at most 10 fluidic circuits per 1000 mm$^2$, at most 50 fluidic circuits per 1000 mm$^2$. Alternatively, the device can comprise at most 1 mm of conduit length per 10 mm$^2$ area, at most 10 mm of conduit length per 10 mm2 or at most 20 mm conduit length per 10 mm$^2$. Alternatively, the device can comprise valves at a density of at most 1 valves per cm$^2$, at most 4 valves per cm$^2$, or at most 10 valves per cm$^2$. Alternatively, the device can comprise features, such as channels, that are no less than 5 mm apart edge-to-edge, no less than 1 mm apart, no less than 500 microns apart or no less than 100 microns apart.

Materials

The elastic layer typically is formed of a substance that can deform when vacuum or pressure is exerted on it, and can return to its un-deformed state upon removal of the vacuum or pressure, e.g., an elastomeric material. The deformation dimension can be less than ten mm, less than one mm, less than 500 um, or less than 100 um. As the distance the membrane must deform to close the valve is decreased, the deformation required is lessened. Thus, a wide variety of materials can be employed. Generally, the deformable material has a Young's modulus having a range between about 0.001 GPa and 2000 GPa, preferably between about 0.01 GPa and 5 GPa. Examples of deformable materials include, for example, thermoplastic or cross-linked polymers such as silicones (e.g., polydimethylsiloxane), polyimides (e.g., Kapton™, Ultem), cyclic olefin co-polymers (e.g., Topas™, Zeonor), rubbers (e.g., natural rubber, buna, nitrile, EPDM), styrenic block co-polymers (e.g., SEBS), urethanes, perfluoro elastomers (e.g., Teflon, PFPE, Kynar), Mylar, Viton, polycarbonate, polymethylmethacrylate, santoprene, polyethylene, or polypropylene. Other classes of material that can function as the elastic layer include, for example, metal films, ceramic films, glass films or single or polycrystalline films. Furthermore, an elastic layer can comprise multiple layers of different materials such as combination of a metal film and a PDMS layer.

In certain embodiments, the elastic layer is sealed against the fluidics layer, actuation layer and/or pneumatics layer by chemical bonding. When the elastic layer comprises a silicone polymer (polysiloxane), such as poly(dimethylsiloxane) (PDMS), silanol groups can be introduced on to the surface, which are reactive with hydroxyl groups. Silicones typically are water repellant due, in part, to an abundance of methyl groups on their surfaces. In order to increase the strength of bonding between polysiloxanes and substrates comprising reactive groups, such as hydroxyls (e.g., glass), the siloxanes can be made more hydrophilic by UV ozone, corona discharge, plasma oxidation, or other methods that places silanol groups (Si—OH) on the surface. When activated PDMS is contacted with glass or other materials comprising active hydroxyl groups and, preferably, subjected to heat and pressure, a condensation reaction will produce water and covalently bond the two layers through, e.g., siloxane bonds. This produces a strong bond between the surfaces. The binding between the elastic layer and functional elements, such as valve seats, can be avoided, for example, when these areas are recessed and unable to contact the elastic layer during bonding. Also, the surface of a valve or any functional elements channel in the surface of the fluidic or actuation layer that faces the elastic layer can be provided with a low energy coating to inhibit binding.

The fluidics and actuation layers of the device may be made out of various materials, in particular, polymers, e.g., plastics. These include, for example, an olefin co-polymer (e.g., Zeonor), a cycloolefin polymer ("COP"), a cycloolefin co-polymer ("COC"), an acrylic, a liquid crystal polymer, polymethylmethoxyacrylate (PMMA), a polystyrene, a polypropylene, a polyester, a poly-ABS and a polythiol. The polymeric material that forms the fluidics or actuation layers can be a flowable polymer that can be molded. For example, the fluidics manifold can comprise a polyester (e.g., PET-G) and the actuation layer can comprise ABS plastic. Glass (e.g., borosilicate glasses (e.g., borofloat glass, Corning Eagle 2000, pyrex)), silicon and quartz also can be used.

Provision of Mating Surfaces with Reactive Groups

Layers can be held together by chemical bonding if they have or are provided with reactive groups on their surfaces. In certain embodiments, the elastic layer comprises a siloxane, such as PDMS. Siloxanes have or can be made to have siloxane groups an their surface. These groups are highly reactive with hydroxyl groups. Glass substrates have hydroxyl groups on their surfaces, or these groups can be introduced by exposure to UV ozone or oxygen plasma.

Plastics that are not based on siloxanes (e.g., carbon-based polymers) do not bond easily to other materials, in part because such plastics do not have surface reactive groups available to engage in chemical bonding. However, hydroxyl groups can be introduced onto the surface of plastics by coating the plastics with materials that can generate hydroxyl groups or silanol groups. This material can be applied to the plastic as a coating or a layer. Hydroxyl groups are introduced onto the surface of the coated plastic, for example, by exposing to UV ozone or oxygen plasma. A condensation reaction can take place under ambient temperature and pressure. It also can be accelerated by increasing temperature, e.g., to at least 50° C., and/or by applying pressure to the contacted surfaces.

It can be useful to have selected locations or areas on the surface of the plastic substrate that do not bond or stick to the other substrate. This can be accomplished by eliminating, covering, preventing the formation of, otherwise or neutralizing the material/surface hydroxyl groups at predetermined locations on one of the substrates, e.g., the plastic substrate. For example, the material at a selected location can be ablated, lifted-off or covered with another material. Also, hydroxyl groups can be neutralized after formation. It also can be accomplished by recessing the surface of the substrate so that it does not come into contact with the other surface, or does not do so for long enough for bonding to occur. It also can be accomplished by applying the coating to selected locations at which the article will bond to a second article. Such unbonded areas are useful locations for the placement of functional elements, such as valves, at which sticking between the plastic layer and the second layer is undesired.

In addition, metals like steel, bronze, nickel and nickel-cobalt alloys may also be used to fabricate the master of the device of the invention, e.g., by traditional metal machining Three-dimensional fabrication techniques (e.g., stereolithography) may be employed to fabricate a device in one piece. Other methods for fabrication are known in the art.

The plastic can be coated with a siloxane, e.g., a polysiloxane. Such materials are commercially available. Silane coatings are described, for example, in U.S. Pat. No. 4,113,665 (Law et al.); U.S. Pat. No. 4,847,120 (Gent); U.S. Pat. No. 5,275,645 (Ternoir et al.) and U.S. Pat. No. 6,432,191 (Schutt). Scratch-resistant coatings used in optical applications are useful. Commercially available materials include, for example, 3M 906 Abrasion Resistant Coating (3M®), Duravue (TSP, Inc., Batavia Ohio), PSX (Coatings West, Brea, Calif.) and GR-653LP (Techneglas, Perrysberg, Ohio). Silicones from Momentive Performance Materials are useful coatings. SHC 5020 is particularly useful for acrylics and PHC 587 is particularly useful for polycarbonates and COC. These coatings can be applied to plastic by well known methods such as dipping, spraying, etc. Plastics coated with such materials are commercially available. They include, for example, Acrylite AR® (Evonik Industries) which uses 3M 906, and TEC-2000 (ACP Noxtat, Santa Ana, Calif.). Another silane-based coating useful in this invention is described in US 2009/0269504 (Liao, Oct. 29, 2009) and WO 2010/042784 (Lee et al., Apr. 15, 2010).

The metal oxide can be applied to a surface already coated with another material, such as a refractory metal that facilitates adhesion of the metal oxide to the surface. Refractory metals include, for example, chromium, titanium, tungsten, molybdenum, niobium, tantalum and rhenium. The chromium layer need only be thick enough to allow the metal to adhere, for example, between 25 Angstroms and 100 Angstroms, e.g., around 30 Angstroms. The metal oxide layer also can be thin enough to just cover the surface and provide sufficient hydroxyls for bonding. Thus, the metal oxide layer can be between 25 Angstroms and 100 Angstroms. The metal can be applied by sputtering, evaporation, or atomic layer deposition using a shadow mask that exposes the surfaces to be coated, or by other techniques. Sputtering can use, for example, Rf or DC energy. So, for example, a 30 Angstrom layer of chromium can be applied to selective surfaces, followed by a 30 Angstrom layer of titanium oxide.

The oxide can comprise a layer of a semiconductor oxide, for example, silicon oxide or germanium oxide deposited on a substrate. Alternatively, the substrate can be a silicon or germanium material (e.g., a silicon wafer or a germanium wafer), the surface of which comprises the semiconductor oxide.

Oxide can be deposited on the plastic substrate by a number of different methods known in the art. Certain of these methods are particularly compatible with producing a patterned substrate in which selected locations are not coated with the oxide. The surface of the plastic can be prepared for example by cleaning with oxygen plasma or any method of cleaning a plastic surface known in the art. These include, for example, chemical vapor deposition (CVD), plasma enhanced chemical vapor deposition (PECVD), physical vapor deposition (PVD) (e.g., sputtering or evaporation), application of liquid, e.g., by flowing or dipping or atomic layer deposition (ALD).

Low Energy Surfaces

Devices of this invention also can be provided that have functional surfaces treated to decrease their surface energy. Low surface energies decrease sticking of the elastic layer to the fluidics or actuation layer to which it is attached. When the elastic layer is a silicone, such as poly(dimethylsiloxane) (PDMS), the water contact angle of the treated surface should be at least 90°, at least 100° degrees, at least 115°, at least 120° degrees or at least 140° degrees. (See, e.g., U.S. Patent Publication 2010/0303687, Blaga et al., Dec. 2, 2010.)

Many materials are useful to create low surface energies on exposed surfaces. In one embodiment, the material is a low energy polymer such as a perfluorinated polymer or a poly(p-xylene) (e.g., parylene). Teflon is a known low surface energy material, which is also inert and biocompatible. The material can be a self-assembled monolayer. Self-assembled monolayers can be made from silanes, including for example, chlorosilanes or from thiol alkanes. They typically have a thickness between about 5 Angstroms and about 200 Angstroms. The low energy material can be a metal (e.g., a noble metal such as gold, silver or platinum). Other materials that can be used to provide low surface energy surfaces include hard diamond, diamond-like carbon (DLC) or a metal oxide (e.g., titania, alumina or a ceramic).

Perfluorinated polymers include, for example, Teflon-like materials deposited from fluorinated gases, PTFE (polytetrafluoroethylene, Teflon®), PFA (perfluoroalkoxy polymer resin), FEP (fluorinated ethylene-propylene), ETFE (polyethylenetetrafluoroethylene), PVF (polyvinylfluoride), ECTFE (polyethylenechlorotrifluoroethylene), PVDF (polyvinylidene fluoride) and PCTFE (polychlorotrifluoroethylene). The material can have a thickness of about 100 Angstroms to about 2000 Angstroms.

In one embodiment, the material comprises a noble metal, such as gold. The noble metal can be applied directly to the surface to be coated. Also, the noble metal can be applied to a surface already coated with another material, such as a refractory metal that facilitates adhesion of the noble metal to the surface, as described above. Refractory metals include, for example, chromium, titanium, tungsten, molybdenum, niobium, tantalum and rhenium. For example, a 1000 Angstrom layer of chromium can be applied to selective surfaces, followed by a 2000 Angstrom layer of gold. The chromium layer need only be thick enough to allow the gold to adhere, for example, at least 30 Angstroms, at least 50 Angstroms, at least 100 Angstroms, at least 500 Angstroms or at least 1000 Angstroms. The noble metal, also, need only be thick enough to inhibit binding of the elastic layer. For example the noble metal can have a thickness of at least 50 Angstroms, at least 100 Angstroms, at least 500 Angstroms, at least 1000 Angstroms or at least 2000 Angstroms. The metal can be applied by sputtering, evaporation, or atomic layer deposition using a shadow mask that exposes the surfaces to be coated, or by other techniques. Sputtering can use, for example, Rf or DC energy.

Assembly

For assembly, the fluidics layer, elastic layer and the actuation layer are mated and held together in such a way that fluid in the conduits does not leak out between the layers. The layers can be held together by physical pressure or by chemical bonding. For two-layer valves, the fluidics and actuation layers may be mated and held together using similar methods known in the art.

In one embodiment, as described in U.S. sealing rings in the actuation layer exert localized pressure on the elastic layer against the fluidics layer to form a pressure seal. Non-uniformities in the facing surfaces may result in pressures that are not uniform across the entire surface of the sealing ring. However, it is believed that localizing the pressure in the sealing rings results in sufficient pressure across the ring surface to seal the valves. This allows the use of parts made of materials in which tight tolerances are more difficult to achieve.

In some embodiments, layers are mechanically scaled (or pressed) against one another. In some cases, such mechanical sealing generates pressure (or squeezing) that holds the layers together. Pressure or squeezing of the layers together can be achieved using mechanical fasteners. Mechanical fasteners can be selected from, for example, a screw, a clip, a snap fastener, a staple, a rivet a band (e.g., an elastic band) and a pin. For example, bores through the three layers can function as guides for pins or screws. The fluidic or actuation layer can comprise a snap that tightly snaps into a groove or recess in the other layer. Accordingly, the actuation layer may not be completely planar, but may include bend that is flattened when the layers are fastened.

In an example, layers are mechanically sealed against one another with the aid of gluing (e.g., glue screw). In such a case, glue may be provided between the layers to hold the layers together when compressed. In another example, layers are mechanically sealed against one another with the aid of a clamp or vacuum. In another example, layers are mechanically sealed against one another with the aid of heat sealing. In another example, layers are mechanically sealed against one another with the aid of ultrasonic welding.

To improve the seal between the elastic layer, such as PDMS, and the fluidics and actuation layers, the elastic layer can be subjected to treatments to activate reactive groups on the surface that will bond with reactive groups on the surface of the fluidics or actuation layers, e.g., hydroxyl groups. Similarly, in two-layer valves where the diaphragm is a component of the fluidic or actuation layer, the fluidic or actuation layer can be similarly treated.

In one method, the layers are sealed by being bonded together with covalent or non-covalent bonds (e.g., hydrogen bonds). This can be achieved by mating the layers, e.g., fluidics, elastic and actuation layers, together as a sandwich and applying pressure and heat. For example, when the elastic layer comprises a silicone, such as PDMS treated as above to render the surface more hydrophilic, and the fluidics and actuation layers are coated with a material comprising surface hydroxyl groups, the pieces can be pressed together at a pressure of 100 kg to 500 kg, e.g., about 300 kg. They can be baked between 25° C. and 100° C., e.g., about 90° C. or at about 150° C. for about 5 minutes to about 30 minutes, e.g., about 10 minutes, depending on the combination of temperature and pressure used. This will cure the bonding between the elastic layer and the sealing surfaces. After bonding the layers together, conduits can be flushed with, for example, PEG (e.g., PEG-200) or 1-2 propane diol (Sigma #398039).

Sample Processing Module

The invention provides for a sample processing module that can be integrated with an analysis system. The sample processing module can be configured to prepare a sample for an analysis procedure. For example, the sample processing module can be configured to perform one or more steps, including lysing cells, purifying and/or isolating nucleic acids from a sample and fragmenting the purified and/or isolated nucleic acids. An object species is substantially pure or substantially purified if it is the predominant species present (i.e., on a molar basis, more abundant than any other individual macromolecular species in the composition), and a substantially purified fraction is a composition wherein the object species comprises at least about 50% (on a molar basis) of all macromolecular species present. Generally, a substantially pure composition means that about 80% to 90% or more of the macromolecular species present in the composition is the purified species of interest. The object species is purified to essential homogeneity (contaminant species cannot be detected in the composition by conventional detection methods) if the composition consists essentially of a single macromolecular species. Solvent species, small molecules (<500 Daltons), stabilizers (e.g., BSA), and elemental ion species are not considered macromolecular species for purposes of this definition. To purify refers to performing a process of increasing the concentration of an object species in a composition compared with at least one other individual macromolecular species in a composition and substantially purify refers to purifying an object species to the point of being the predominant species present, i.e., to be substantially pure.

In some embodiments, the sample processing module can perform whole genome amplification. As shown in FIG. 1, the sample processing module can have one or more submodules. The submodules can include a cell lyser (which can also lyse cells in tissue), a DNA purifier, and a DNA fragmenter. The dimensions of the sample processing module can be about or no more than any of about 0.25, 0.5, 0.75, 1, 1.25, 1.5, 1.75, 2, 3, 4, 5, or 6 cubic feet. The sample processing module can prepare the sample for an analysis procedure in about or no more than any of about 1, 2, 3, 4, 5, 6, 7, 8, 9, 10, 13, 15, 20, 25, 30, 30, 40, 45, 50, 55, or 60 minutes. The sample processing module and/or the steps for preparing a sample for analysis can be automated by a computer or by computer logic. In some embodiments, the sample processing module can prepare at least 1, 2, 3, 4, 5, 6, 7, 8, 9, 10, 11, 12, 13, 14, 15, or more than 15 different samples simultaneously. In an exemplary embodiment, six sample processing modules can be integrated into a sample-to-sequence system, each sample processing module capable of processing two samples simultaneously.

The sample processing module can 1) lyse cells and viruses, 2) purify total DNA or RNA using paramagnetic bead-based nucleic acid purification, and 3) fragment the DNA or RNA into size selectable ranges of base fragments, such as 600-800 bases or 200-300 bases. The lysis, nucleic acid purification, and fragmentation can be integrated on a miniaturized, fully automated device and can recover sufficient DNA or RNA from crude samples at, more than, or less than about 300 cells or viral particles per sample. When used herein, "cells" can refer to eukaryotic cells, prokaryotic cells, archaea cells, spores, viral particles, or fragments thereof. In some embodiments, a fully automated device can recover sufficient nucleic acid from samples comprising less than 10 cells per mL of sample. In some embodiments, a fully automated device can process samples containing only one type of cell or samples containing mixtures of cells at an input sample concentration ranges, for example, from ten to ten million organisms per milliliter. In some embodiments, the sample processing module can perform its functions, e.g. produce fragmented nucleic acid molecules from an input sample, in less than or about 15, 30, 45, 60, 75, 90, 105, 120, 150, 180, 210, or 240 minutes.

The sample processing module can have one or more chambers. A chamber can be configured to have a port for receiving a sample. The chamber can hold a volume of about, no more than any of about, or more than any of about 0.01, 0.05, 0.1, 0.2, 0.3, 0.4, 0.5, 0.6, 0.7, 0.8, 0.9, 1, 1.25, 1.5, 2, 2.5, 3, 5, 7, or 10 mL. The sample processing module can also have one or more waste chambers for collecting waste products. The sample processing module can contain microfluidic elements, such as microfluidic chamber, channels, or valves.

The sample processing module can receive any type of sample. The sample can be a cellular sample, a cell fraction, an environmental sample, an unpurified sample, a tissue sample, or a biopsy sample, a blood sample, a urine sample, or any other bodily fluid. The tissue sample can be a piece of hair, skin, nail, flesh, or any other part of a body. The sample can include cells, spores, viruses in environmental, food samples, air samples, processed food samples, and clinical samples. The sample can be collected from an object, a human, an animal, a needle, or a crime scene. The sample may be collected on a swab, an adsorbent pad, a knife, a scalpel, a syringe, a biopsy needle, or any other device for collecting samples. The sample processing module can have a receiving port configured to receive the sample from any object used to collect the sample.

A sample processing module can include a cartridge. A cartridge can reversibly engage one or more submodules of the sample processing module. In other embodiments of the invention, the cartridge is integrated with one or more submodules. The cartridge comprises one or more chambers that can be fluidically connected to submodules of the sample processing module or any other module described herein. The chambers can include one or more reagents. The reagents can be reagents for sample processing, including a lysis buffer, beads, and a clean-up buffer. One or more chambers of the cartridge can have a volume that is about, no more than any of about, or more than any of about 0.01, 0.05, 0.1, 0.2, 0.3, 0.4, 0.5, 0.6, 0.7, 0.8, 0.9, 1, 1.25, 1.5, 2, 2.5, 3, 5, 7, or 10 mL. The cartridge can include one or more chambers for performing a reaction.

The sample processing module can also include a cell lysis submodule. The cell lysis submodule can perform lysis or homogenization using chemical, enzymatic and/or mechanical techniques. Lysis can be accomplished using commercially available technology integrated into the sample processing module. A cell lysis submodule using chemical techniques can include one or more chambers for mixing a sample with a lysis buffer. The lysis buffer can include a low pH buffer (pH of about or no more than any of about 1, 2, 3, 4, 5, 6, or 7) or high pH buffer (pH of about or greater than about 7, 8, 9, 10, 11, 12, 13, or 14), a low or high salt concentration buffer, or any combination thereof. A cell lysis submodule using mechanical techniques can include a heating device, a sonication device, bead-beating device, blender, a shear inducing device, or other mechanical devices known to lyse cells. The shear inducing device can include one or more nozzles or valves for inducing shear to the sample. The cell lysis submodule can also include one or more beads for performing bead beating. The beads can be zirconia or silica beads or other materials. The cell lysis submodule can be purchased from commercial sources, such as an OmniLyse from Claremont BioSolutions (Upland, Calif.). In some embodiments, the cell lysis module can recover nucleic acids from a sample at approximately linear efficiency over at least 4, 5, 6, 7, 8, 9, or 10 orders of magnitude.

The sample processing module can include a nucleic acid purification submodule. The nucleic acid purification submodule can comprise one or more chambers for collecting or recovering nucleic acids. The chamber can include one or more surfaces for binding or complexing with nucleic acids. The surfaces can be a surface on a wall chamber, or a surface on a solid material, particle, or gel material. Examples of solid materials or particles include beads, paramagnetic beads, nanoparticles, and magnetic beads. The surface can bind to nucleic acids using specific interactions (e.g., using antibodies, nucleic acid probes, aptamers, or other specific binders) or non-specific interactions (e.g., using electrostatic interactions, charge interactions or other non-specific binders).

The nucleic acid purification submodule can include reagents for performing magnetic bead-based purification. In some embodiments, the magnetic beads can be carboxylated magnetic beads, e.g., carboxylated Double Speed magnetic beads from Scradyne. The sample processing module can have one or more magnets configured to attract or collect the magnetic beads.

Figure 4:
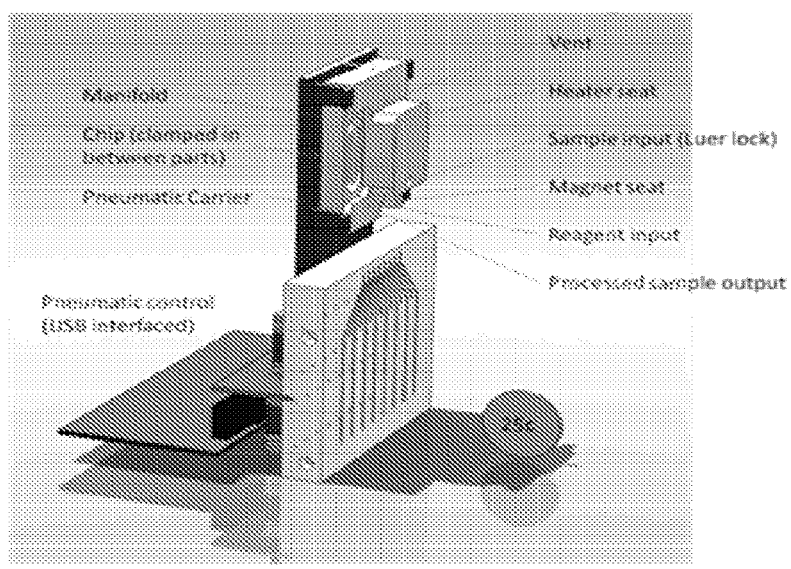
FIG. 4 shows a diagram of a sample processing module for lysis and DNA purification.
Figure 5:
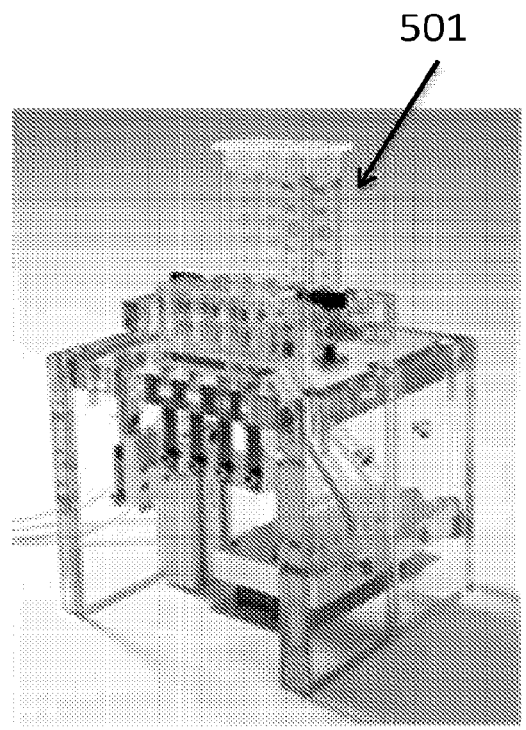
FIG. 5 shows an exemplary sample processing module that can receive large volume samples in syringe barrels. The samples can be processed within a polymer cartridge. Fluid routing can be controlled by a microchip with pneumatically actuated valves integrated within the sample processing module.

An example of a sample processing module having modules for lysis and nucleic acid purification is shown in FIG. 4. The module has a manifold, a chip (clamped in between parts), a pneumatic carrier, a pneumatic control, a vent, a heater seat, a sample input (Luer lock), a magnet seat, a reagent input, and a processed sample output. Another example of a sample processing module is shown in FIG. 5. The sample processing module shown in FIG. 5 utilizes a syringe barrel (501) to receive a sample.

Figure 20:
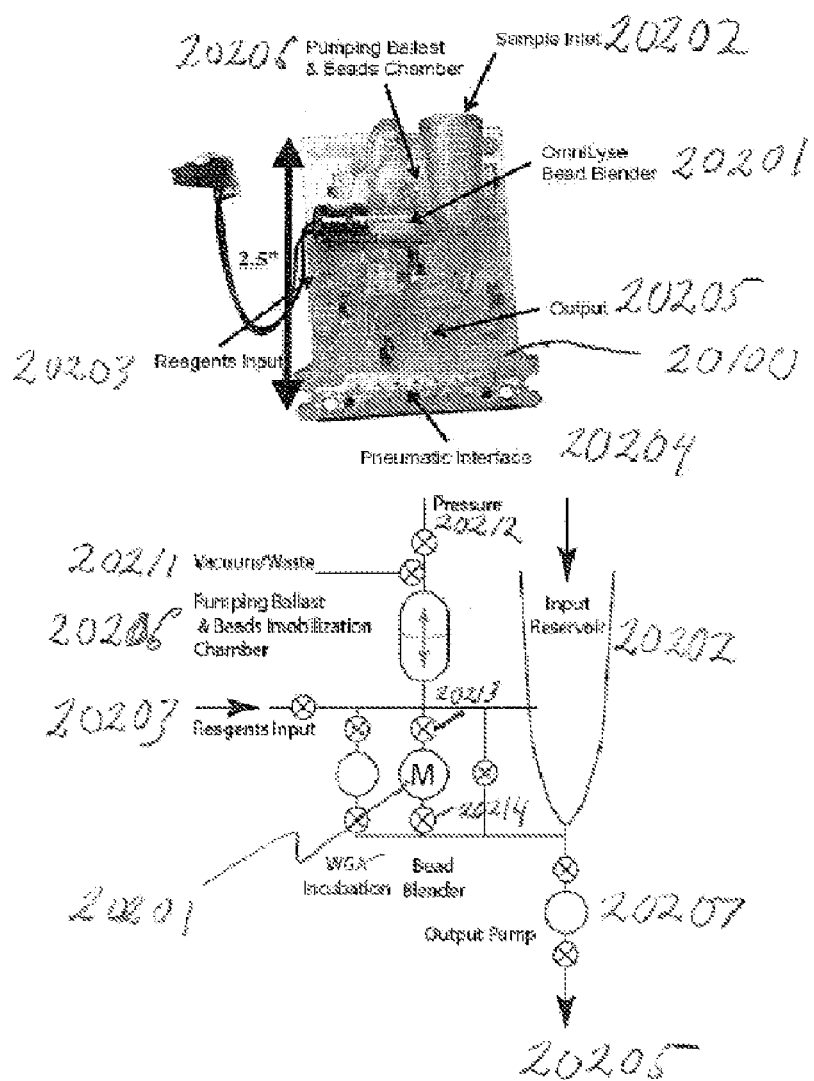
FIG. 20 shows an exemplary embodiment of a sample processing module.

Another example of a cartridge-based sample processing module is shown in FIG. 20. The module has a funnel-shaped sample inlet leading to a chamber that accepts 0.3-1.5 mL samples, a mechanical lysis submodule, a chamber to capture nucleic acids onto paramagnetic beads, a pneumatic interface, an outlet port, and a fluidics microchip. The outlet port can be fluidically connected to, e.g. a library preparation module. The sample processing module can comprise a mechanically sealed microfluidic chip, and can be about 2.5 inches in height.

This functional prototype sample processing module cartridge was made using rapid prototyping techniques having a design compatible with injection molding. A microfluidic foil and an elastomeric valve/pumping membrane are sandwiched between a pair of liquid and a pneumatic manifolds. The liquid manifold also provides the interface and structural support for the on-board lysis device (e.g. mechanical bead blender).

The sample processing module in FIG. 20 works as follows. A sample is loaded into the sample inlet and then pumped using the microfluidic pumps to the lysis chamber at the desired time. The lysis chamber, e.g. OmniLyse, can use beads and a rapid blending motion to disrupt cells, tissue, spores, viruses, or other samples. A prototype Sample Processing Module shown in FIG. 20 incorporates an off-the-shelf lysis device. The OmniLyse from Claremont Bio-Sciences provides the benefits of bead beating in a miniature format by employing a rotating bed of zirconium beads. This device has been shown to effectively lyse spores and other types of cells. The microfluidic pumps can then move the lysed sample to the bead chamber where paramagnetic beads are used to capture and purify the released nucleic acids. Different beads including SPRI, SpeedBeads, MagnaSil, nanoparticles, and other beads can be used. The nucleic acid is first typically bound to the beads and then washed to remove contaminants. Reagents for the subsequent bead based clean-up (e.g., SPRI beads with a PEG mix and 70% EtOH for washing) are metered by a (similar) reagents distributor cartridge (not shown) and pushed in via the Reagents Input and mixed with the sample. After having been captured in a smaller compartment and washed, the beads now carrying the DNA are re-suspended in a solution such as 60 μL EtOH and pumped out via the Output port shown.

Figure 26:
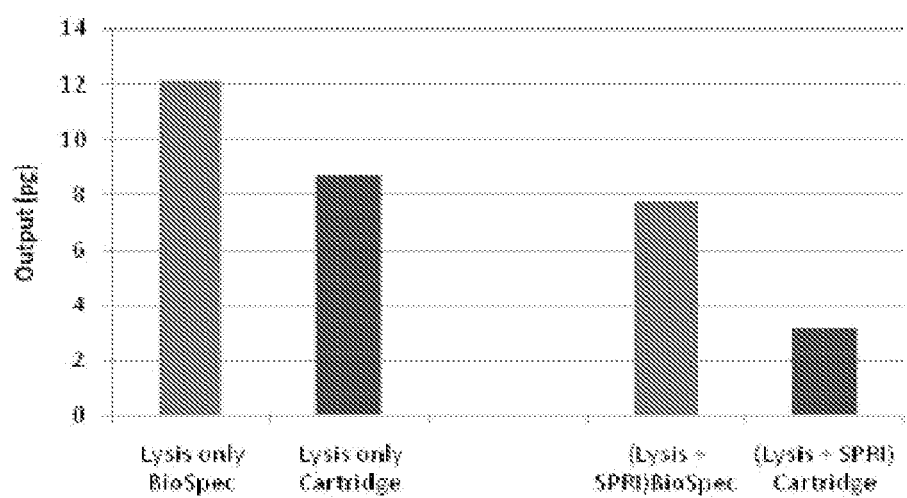
FIG. 26 shows a bar graph for lysis efficiency using an embodiment of a sample processing module.

The prototype sample processing module cartridge shown in FIG. 20 has been shown to be able to lyse bacteria cells and spores. In FIG. 26, *Bacillus atrophaeus* spores in 600 μL samples at a concentration of 105 cfu/mL were processed through the Sample Processing Module using an OmniLyse bead beating devise and paramagnetic bead nucleic acid purification and the results compared to bead beating using a Biospec bead beating device and manual SPRI (Beckman) nucleic acid purification. The output was measured using qPCR in both cases. The prototype Sample Processing Module was shown to lyse *Bacillus atrophaeus* spores (labeled lysis only cartridge) and to lyse and purify nucleic acids in an integrated, automated operation [(lysis+SPRI) cartridge]. The sample processing module can include an amplification submodule which can be whole genome amplification (WGA) or directed amplification. The amplification submodule can perform isothermal amplification or amplification with thermal cycling. In some embodiments, WGA is performed using random hexamer priming. In some embodiments, WGA is performed using Phi29 DNA polymerase. In some embodiments, WGA is performed using rolling circle amplification circularized nucleic acid samples. In some embodiments, directed amplification can use specific primers to amplify only regions of interest using PCR or other amplification methods well known to one skilled in the art and described herein.

The sample processing module can include a nucleic acid fragmenting submodule. The fragmenting submodule can fragment nucleic acid using mechanical or chemical techniques, such as chemical or enzymatic fragmentation, e.g., digestion by restriction enzymes, Fragmentase (New England Biolabs, Ipswich, Mass.), or mechanical fragmentation. The fragmenting submodule can reduce the size of a nucleic acid sample to fragments of less than 200 bases, about 200-300 bases, about 300-500, about 500-800, about 600-700, or about 650 base pairs, about 1000-2000, about 2000 to 5000, about 2000-20,000, about 20000 to 100,000, about 100,000 to 1,000,000 or larger sizes as desired by the requirements of the sequencer. The fragmenting submodule can reduce the size of a nucleic acid sample to size distribution of within 10, 50, 100, 150, 200, 300, 400, 500, 1,000, 10,000, 100,000, 1,000,000, or 10,000,000 base pairs. The fragmenting submodule can produce nucleic acids fragments of any predetermined size, which may be selected based on the efficiency, yield of circularization, application, and/or read length of the analysis method. In some embodiments, the nucleic acid fragmenting module includes a sonicator. For example, the sonicator can be a Covaris sonicator.

Figure 6:
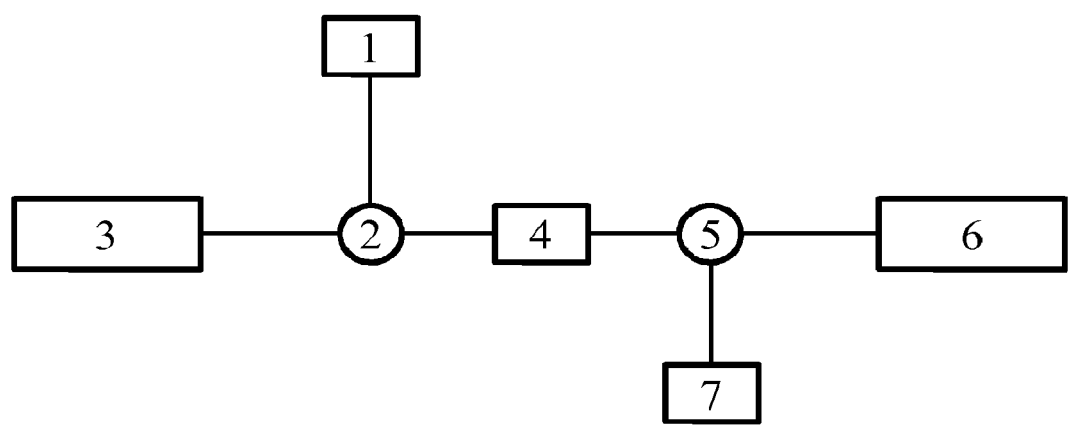
FIG. 6 shows a schematic of an exemplary shearing device.

The nucleic acid fragmenting module can be a nucleic acid shearing module. An example of a nucleic acid shearing module is shown in FIG. 6. As shown in FIG. 6, the shearing module can include pressure sources (3, 6) that are fluidically connected by one or more channels. The pressure sources can be syringes that are automated by a robot or other mechanical or electrical force. Sample can be inputted at an inlet (1) to a chamber (2). The channel can have a shearing region (4) that has a width and a depth such that nucleic acids that are passed from one syringe to the other syringe, or from a first chamber (2) to a second chamber (5) experience sufficient shear to fragment the nucleic acids. The shearing region can have sections with high and low cross-sectional area. The change in cross-sectional area can be increases and decreases in size of about or greater than about 0.1, 0.5, 1.5, 2.5, 5, 7.5, 10, 15, or 20 times. The channel can have regions that are 50 microns deep and 100 microns wide. Other regions of the channel can have cross-sections that are about or greater than about 1.5, 2.5, 5, 7.5, 10, 15, or 20 times larger. A sheared sample can be output from the nucleic acid fragmenting module at an outlet (7).

The submodules of the sample processing module can be fluidically connected by one or more tubes and/or channels. The submodules of the sample processing module can be fluidically connected by a chip comprising one or more channels. The chip can also comprise one or more valves, e.g., pneumatically actuated valves, for controlling and/or driving liquid flow. The chip can be a microfluidic chip. The valves can be used for pumping liquids from one submodule to another, or from the sample processing module to a downstream module. The valves can be microfluidic valves that form a microfluidic pump. The valves of the chip can be controlled by a computer. The liquids within the sample processing module can be driven by internal pressure sources, external pressure sources, gravity, electroosmosis, vacuum, or any combination thereof. An example of an external pressure source can include pressurized air or a syringe pump.

The sample processing module and submodules thereof, or any other modules and submodules described herein, can be made from glass, polymer, metal, ceramics, or any other material. In some embodiments, the polymer is a plastic material. A plastic material may include any plastic known to those skilled in the art, such as cyclic olefin copolymer, polypropylene, polystyrene, polyethylene, polyethylene terephthalate, polyester, polyamide, poly(vinylchloride), polycarbonate, polyurethane, polyvinyldiene chloride, cyclic olefin copolymer, or any combination thereof. The sample processing module, or any other module or submodule described herein, can be formed using any technique known to those skilled in the art, such as soft-lithography, hard-lithography, milling, embossing, ablating, drilling, etching, injection molding, or any combination thereof.

A sample processing module configured to perform cell lysis, nucleotide isolation, and polynucleotide fragmentation can include a cell lysis submodule, a nucleotide isolation submodule, and a polynucleotide fragmentation module. In some embodiments, the submodules can be incorporated into a cartridge. A cell lysis submodule can include a chamber for receiving a sample. The receiving chamber can be a syringe barrel, a chamber formed in plastic, or a chamber formed in glass or other suitable materials. The receiving chamber can have a volume of about 1 mL. The chamber can have a desired volume to receive any volume of sample described herein or be connected to an upstream fluidic system that can receive as input larger volumes such as 10 mL or more, for example by sequentially accepting 1 mL aliquots into the 1 ml chamber. The receiving chamber can be in thermal contact with a heating device, e.g., a Peltier thermoelectric heater/cooler. The receiving chamber can be fluidically connected to a downstream polynucleotide isolation submodule by one or more channels or tubes. The channels can be microfluidic channels, or they can be macrofluidic channels. The channels can comprise one or more valves, e.g., pneumatically actuated valves. The receiving chamber can be fluidically connected to a downstream polynucleotide isolation submodule by an integrated processing chip, described herein.

In one embodiment, the sample processing module can be made using rapid prototyping techniques having a design compatible with injection molding. A microfluidic foil and an elastomeric valve/pumping membrane can be sandwiched between a pair of liquid and a pneumatic manifolds. The liquid manifold can also provide the interface and structural support for the on-board lysis device (mechanical bead blender). The cartridge can have a funnel-shaped inlet that accepts a 0.3-1.5 mL sample that is then being circulated through the bead blender for any desired time. Reagents for the subsequent SPRI clean-up (a PEG/magnetic beads mix and 70% EtOH for washing) can be metered by a (similar) reagents distributor cartridge (not shown) and pushed in via a reagent input port and mixed with the sample. After having been captured in a smaller compartment and washed, the beads now carrying the DNA can be re-suspended in 60 μL EtOH and pumped out via an output port.

An integrated processing chip can be formed by etching one or more channels and/or chambers in a two layers of glass that sandwich an elastomeric layer. One glass layer can be used to form fluidically connected channels and chambers for transferring materials and performing reactions. Another glass layer can be used to form fluidically connected channels and chambers for actuating the elastomeric layer. Other materials can be used in place of glass, including but not limited to rigid and elastomeric polymers. Actuating the elastomeric layer can cause valves within the integrated processing chip to open and close. Actuation of the elastomeric layer can also cause chambers to increase and decrease in volume. Coordinated actuation of the chambers and valves can allow for pumping of liquids within the integrated processing chip.

An integrated processing chip with a polynucleotide isolation submodule can have a purification chamber for performing isolation of polynucleotides. The purification chamber can have a volume of between about 5-1000 nanoliters, 1 to 50 microliters, 50-100 microliters, 10-1000 microliters, 50-500 microliters, or about 100 microliters. The chamber can have a solid surface for immobilizing or complexing with polynucleotides. The solid surface can have affinity binding moieties or otherwise complex with the polynucleotides through specific or non-specific interactions. The chamber can have a solid surface for immobilizing or complexing with enzymes or other proteins. The solid surface can be a wall of the integrated processing chip or can be beads or nanoparticles. The beads may be paramagnetic beads that respond to a magnetic field. In some embodiments, the beads can be supplied to the purification chamber through a bead reagent chamber. The bead reagent chamber can be a chamber in the integrated processing chip, or can be a chamber outside the integrated processing chip. In some embodiments, the bead reagent chamber is within a cartridge that can be reversibly engaged with the integrated processing chip. Beads in the bead reagent chamber can mix with lysed sample, and then be collected in the purification chamber by application of a magnetic field to the purification chamber. Wash buffer and elution buffer chambers can also be fluidically connected to the purification chamber. The wash buffer and elution buffer chambers, like the bead reagent chamber, can be within the integrated processing chip or outside the integrated processing chip. The wash buffer and elution buffer can be used to prepare eluted and isolated polynucleotides.

The sample processing module can include a fragmentation submodule that is fluidically connected to the polynucleotide isolation submodule. Eluted nucleotides can then be directed to the polynucleotide fragmentation submodule through fluidic connections within the integrated processing chip. The polynucleotide fragmentation submodule can be within the integrated processing chip, or can be outside the integrated processing chip. In one embodiment, the cell lysis submodule can be used to shear the unpurified nucleic acid e.g. the OmniLyse or bead beating methods shear nucleic acids as cells or tissue are lysed. In a preferred embodiment, the fragmentation submodule can be downstream of the polynucleotide isolation submodule. In one embodiment, the polynucleotide fragmentation submodule can have a first chamber for receiving the purified nucleotides fluidically connected by a shearing channel (which can be a channel of about 100 microns in width and 50 microns in depth that increases and decreases in cross sectional area, as described herein) to a second chamber. The first chamber and second chamber can have a volume of about 10-1000 microliters, e.g., about 100 microliters. Modules for performing sample preparation are described in U.S. Provisional Application No. 61/320,624, filed Apr. 2, 2010, and U.S. Provisional Application No. 61/330,154, filed on Apr. 30, 2010, which are each incorporated by reference for all purposes. The nucleotide fragmentation submodule can have a fluidic driving force for moving the purified nucleotides between the first and second chamber such that shear is induced and the nucleotides are fragmented. The driving force can be an external driving force, or be a driving force supplied by the pneumatically actuated valves in the integrated processing chip. The second chamber can be fluidically connected to an input of a library construction module, described herein.

The Sample Processing Module can include an amplification submodule. The amplification submodule can be inserted between the nucleic acid purification submodule and the nucleic acid fractionation submodules in a preferred embodiment for WGA and other amplification or be inserted after the nucleic acid fractionation submodule if shorter fragments are desired such as directed amplification PCR, SPIA (NuGEN), branched DNA, or other nucleic acid methods.

Library Construction Module

Figure 19:
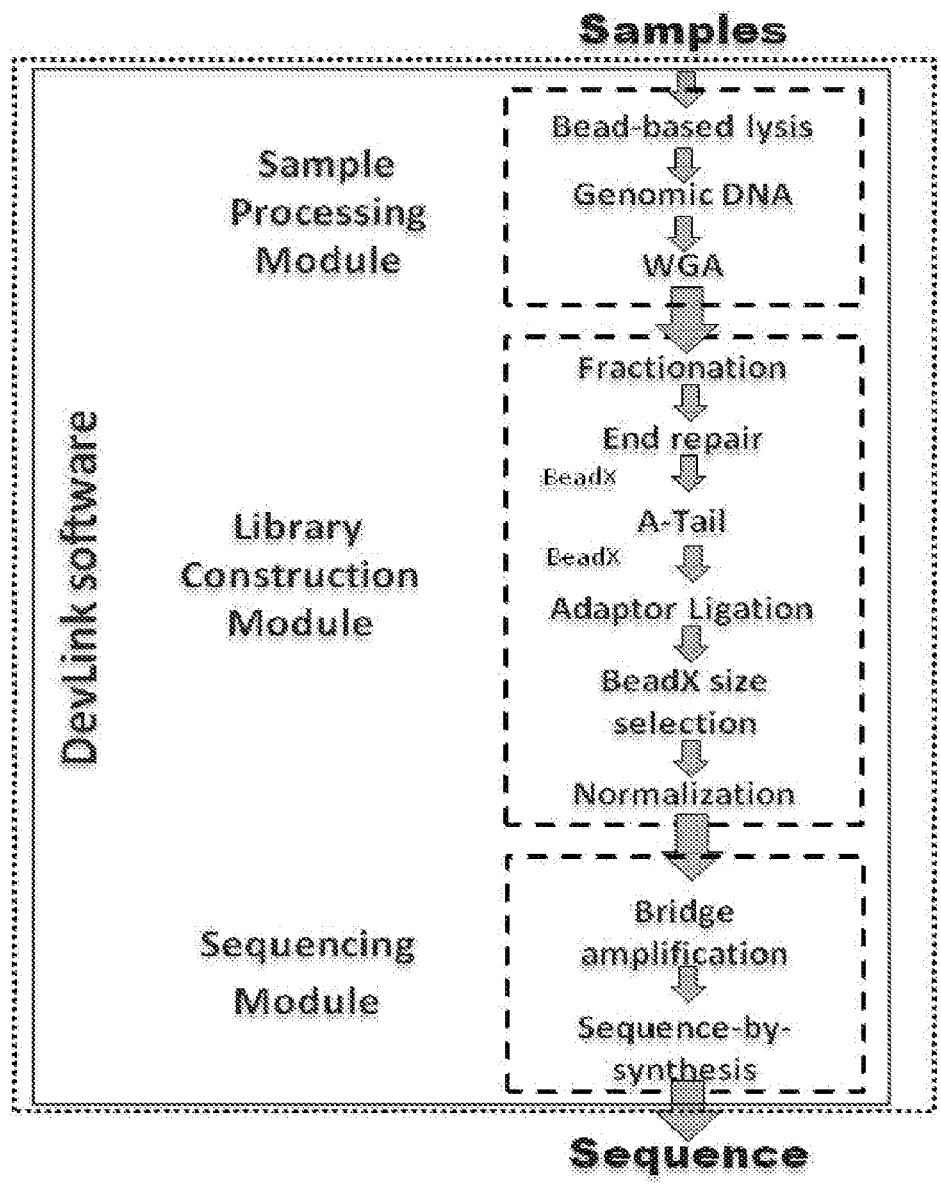
FIG. 19 shows a schematic of steps that can be performed by an integrated sequence to sample system.

The invention provides for a library construction module that can be integrated with either or both of an upstream Sample Processing Module and a downstream analysis system as shown in FIG. 1. The library construction module can perform multi-step molecular biology reactions, such as to convert RNA fragments into DNA and the DNA fragments into either single stranded circularized nucleic acids or double stranded linear nucleic acids that are ready for amplification. The library construction module can be configured to perform different workflows as improved chemistries are developed. In one embodiment, the library construction module can polish frayed DNA ends, ligate a 'vectorette' on the ends to produce circularized nucleic acids, purify the circularized nucleic acids, and produce a representative library of single-stranded circularized nucleic acids. In a preferred embodiment, as shown in FIG. 19, the library construction module can polish a frayed DNA end (end-repair), clean the reaction using paramagnetic beads, add an A tail, clean the reaction using paramagnetic beads, ligate an adapter, and perform two bead cleanups with different size selections to select a given and adjustable length size range of the library. In another embodiment, transposons can be used in the library construction module to prepare libraries; this method can generate libraries with reduced GC bias when starting with less than 50 ng of nucleic acid sample and can require fewer fluidic steps than the process shown in FIG. 19. These steps can be fully integrated onto a miniaturized module. In some embodiments, library preparation can be performed without the use of a subsequent PCR step to amplify the library before emPCR or bridge amplification. In some embodiments, the library construction module can perform its functions, e.g. produce sequencing libraries from fragment nucleic acid samples, in less than or about 5, 10, 15, 30, 45, 60, 75, 90, 105, 120, 150, 180, 210, 240, 270, or 300 minutes.

The library construction module includes one or more chambers for performing reactions. In some embodiments, the chambers perform multiple diverse molecular biological reactions in a programmed sequence. The library construction module, or any other module described herein, can have temperature controlled reservoirs and/or chambers with a non-miscible solvent or solvents. The non-miscible solvent can be used to control evaporation or to form emulsions, as described later herein. The solvent can be perfluorocarbon solvent, which can contract the proximal and distal ends of an aqueous reaction volume.

The library construction module can be configured to receive nucleic acid fragments from a sample processing module, to add adapter to the nucleic acid fragments, and circularize the nucleic acid fragments. The library construction module can also perform one or more purification or recovery steps, including recovering nucleic acids that have been modified with an adapter, recovering circularized nucleic acids, and/or removing non-circularized nucleic acids.

The chambers can be fluidically connected to other submodules and modules by one or more channels in a microfluidic device, by tubing, or by robotics. The channels can comprise one or more pneumatically actuated valves. The chambers can be configured for parallel processing of samples, such that multiple parallel reactions can be performed simultaneously. Examples of a microfluidic chip are shown in FIG. 8, FIG. 9, FIG. 17, and FIG. 21.

Figures 10, 11:
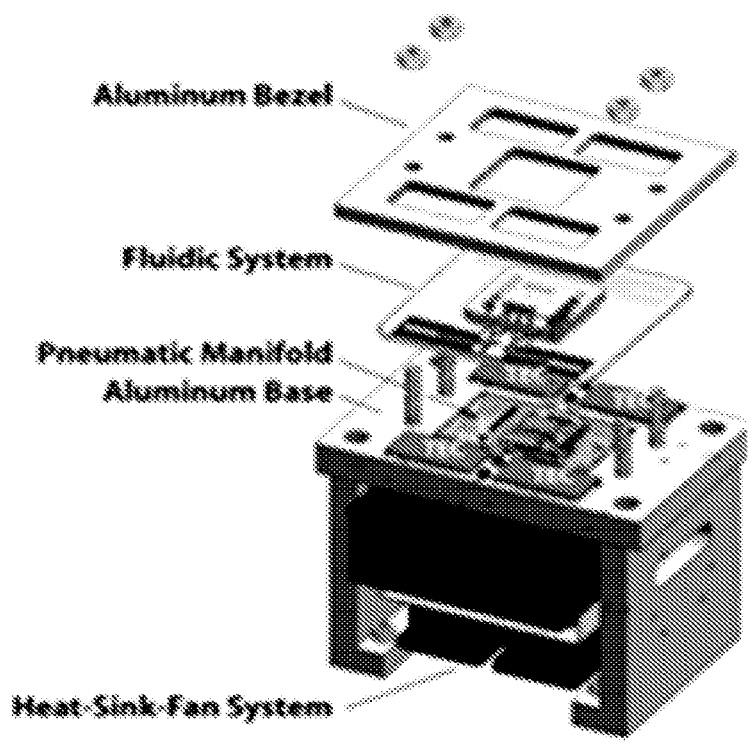
FIG. 10 shows a schematic of steps that can be executed by a library construction module.
FIG. 11 shows a diagram of an integrated processing chip incorporated into a fluidic system that includes the integrated processing chip, a pneumatic manifold, and thermo electric coolers.

FIG. 11 shows a diagram of an integrated processing chip incorporated into a fluidic system that includes the integrated processing chip, a pneumatic manifold, and thermo electric coolers. The integrated processing chip can mount onto an aluminum base with integrated Peltier thermo electric coolers. Pumps and valves in the integrated processing chip can be pneumatically actuated by a pneumatic manifold housed in the aluminum base. An aluminum bezel can evenly distribute force generated by bolts, which can simultaneously (a) compress o-rings on the top surface of the pneumatic manifold against the bottom surface of the integrated processing chip, and (b) press the thermo electric cooler top surfaces against the fluidic system reaction incubation channels.

Figure 8:
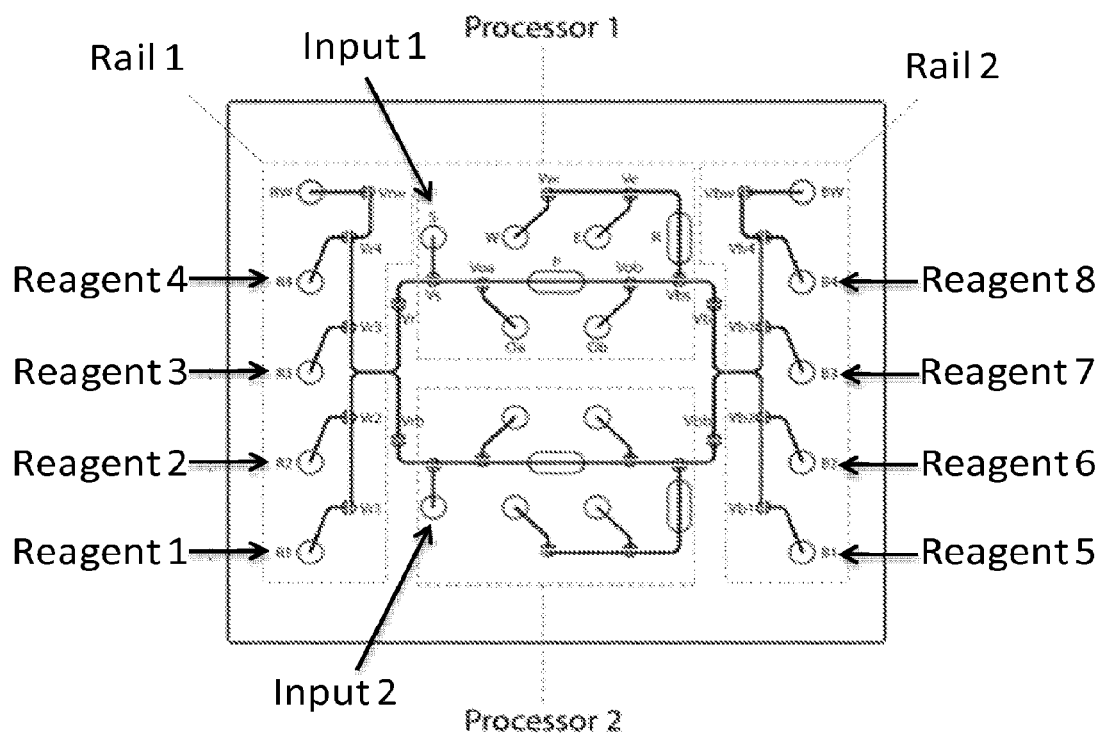
FIG. 8 shows a schematic of an exemplary integrated processing chip that can be a library construction module.
Figure 9:
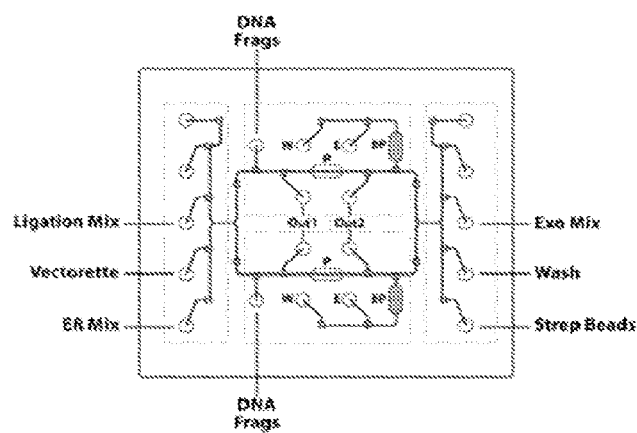
FIG. 9 shows a diagram of an exemplary integrated processing chip that can be a library construction module.

FIG. 8 shows an exemplary integrated processing chip for performing library construction with dual parallel processors and two reagent rails that each can supply four reagents, as described in U.S. patent application Ser. No. 12/321,594. Reaction cascades can be executed by alternate reaction assembly into Out1 (labeled as Oa) and Out2 (labeled as Ob) ports that are mated to temperature-controlled Reaction Incubation Channels in a separate Fluidic Manifold. Magnetic beads can be captured in the Pump structures in each processor (labeled as P).

In one example, the integrated processing chip of FIG. 8 can receive as input fragmented DNA and prepare libraries as follows. An end-repair reaction can be performed by pumping aliquots of a sample (using Input 1, Input 2, or both Input 1 and Input 2 if both processors are used in parallel) and an end-repair master mix into the processor. The reaction can be mixed by pumping through multiple chambers, and the mixed reaction can be loaded through Oa to a reaction incubation channel to incubate the reaction for the desired time. Beads for purifying the resulting end-repaired molecules can then be loaded into the processor and the reaction mixture added back into the processor through Oa. After another round of mixing, the beads comprising the bound end-repair molecules can be retained in the processor while the rest of the mixture can be pumped out of the processor through a waste reservoir W. The process can then be repeated to perform an A-tailing reaction by inputting the A-tailing enzyme mixture from a different reagent port, using the same procedure as described for the end-repair reaction to extend an A tail onto the polished DNA, and then purifying the products using bead-based purification. The process can then repeated again to perform a ligation by inputting the ligation enzyme mixture with a pair of adapters from a different reagent port, using the same procedure as described for the end-repair reaction to ligate the adapters onto the A-tailed and polished DNA fragments, and then purify the products using bead-based purification. Since each bead-based purification can be used to select a minimum or maximum nucleic acid size, a library that contains fragments above a desired size cut-off can be produced by using a 'high-pass' selection with the ligation step. Subsequently, a second 'low-pass' size selection step can be performed to select for fragments below a desired size cut-off. Thus, by using different reagent inputs with different reagents, a library with the desired fragment size range between the 'high-pass' and 'flow-pass' cut-offs can be produced with this microchip design. Figure shows an integrated processing chip configured for performing library construction with inputs for six reagents (ligation mix, vectorette, End Repair (ER) Mix, Exonuclease I (Exo) Mix, Wash, and streptavidin beads) and two DNA fragment inputs. The integrated processing chip has two DNA fragment inputs for performing parallel reactions. Out1 and Out2 are connected to reaction incubation channels for performing reactions. An alternate embodiment of an integrated library construction module is shown in FIG. 21.

A library construction module can be configured to perform one or more reactions. The reactions can be the reactions listed in FIG. 10. The reactions can be performed at any suitable temperature, which may vary with the specific enzyme or reagent used, as is known in the art. In some embodiments, enzymatic or chemical fragmentation, end repair, A-tailing, ligation, or exonuclease digestion can be performed at about 4° C., between about 4° C. and about 16° C., between about 16° C. and about 22° C., between about 22° C. and about 30° C., or above 30° C. Heat inactivation of enzymes can be performed at greater than or equal to about 37° C., greater than or equal to about 45° C., greater than or equal to about 65° C., greater than or equal to about 75° C., or greater than or equal to about 95° C. In some embodiments, heat inactivation can be used to eliminate the bead purification steps between reactions. A-tailing or polynucleotide synthesis can be performed at temperatures of about 16° C. to about 25° C., about 25° C. to about 65° C., or above about 65° C. The reactions can be performed in one or more chambers. The chambers can be surrounded or enclosed by one or more pneumatically actuated valves. The chambers can be pneumatically actuated valves. The chambers can be fluidically connected to one or more sources. The sources can be reagent reservoirs and sample wells. The fluidic connections can comprise one or more pneumatically actuated valves. Possible sources for each reaction are shown in FIG. 10. The reactions can also be the reactions shown in FIG. 19. The reactions can include end repair, addition of a vector, ligation, binding to beads, including streptavidin beads, washing, exonuclease digestion, and heat inactivation. The reactions can add an adapter to a nucleic acid fragment and circularize the nucleic acid fragment. The adapter can be an adapter used in a sequencing reaction. The library construction module can include one or more reagents for performing the reactions described herein. For example, the library construction module can include a chamber comprising adapters.

Figure 21:
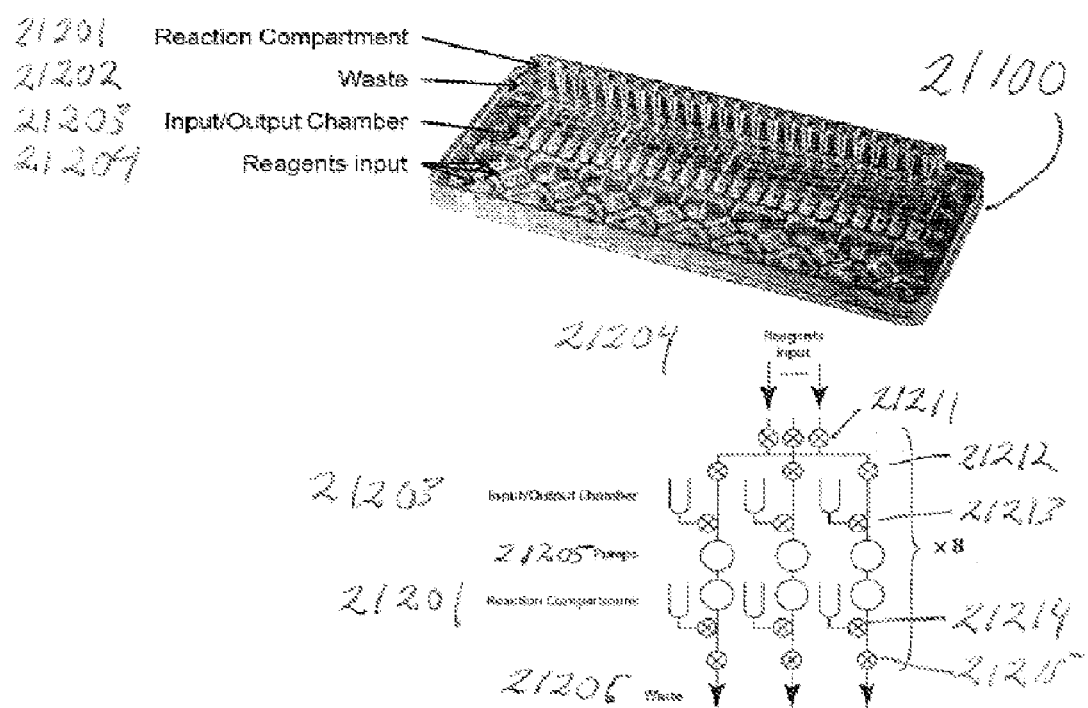
FIG. 21 shows an exemplary embodiment of a library construction module.

In one embodiment of a Library Construction Module, shown as 21100 in FIG. 21, the library construction module produces 12 sequencing libraries from an input of 12 purified and optionally amplified DNA samples. The module can perform any combination of fragmentation, end repair, A-tailing, and ligation using a series of controlled mixing, incubation, and bead-based clean-up operations.

For mixing, the pump 21205 can sequentially withdraw liquid from Input Chamber 21203 and Reagent Input 21204 and expel liquid into Reaction Compartment 21201. For purification, capture beads from reagent input 21204 can be mixed with sample in chamber 21203. The beads can be captured in the reaction compartment 21201 using a magnet (not shown) and the liquid is expelled through the waste port 21206. Wash solutions can be pumped from 21204 through the captured beads in 21201 to the waste 21206. An elution solution can be pumped from 21204 into 21201 causing the product to release from the beads. The product is then pumped to the input chamber 21203.

A typical library construction protocol can perform these mixing and purification operations multiple times using different reagents to perform each step of library construction. Fragmentation can be carried out by mixing a fragmentation master mix, which can for example comprise a restriction enzyme, introduced through 21204 with template in chamber 21203, incubating the mixture, and performing purification. End repair, A-tailing, and ligation can be similarly accomplished, using end-repair master mix, A-tailing master mix, and ligation master mix, respectively. Each master mix can be introduced through reagent input 21204. The final libraries can be positioned in chamber 21203.

In some embodiments, the library construction module can comprise components, such as a flow cell, channel, or chamber, that can be used by the sequencing module. In some embodiments, the library construction, amplification, and the sequencing module can be incorporated as a single combined module. Optionally, a normalization module can also be incorporated as a part of the combined module. The combined module can be incorporated into a microfluidic chip. The combined module can be non-microfluidic. The fluidics of the combined module can be used to prepare libraries as described herein or with alternative chemistries known in the art. In some embodiments, the combined module can perform bridge amplification, emulsion PCR, rolling circle PCR, bead-bound amplification, amplification by ligation, real-time PCR, or any other amplification method as described herein or known in the art. Bridge amplification can be performed in the combined module by, for example, immobilizing the appropriate primers in a flow cell on a shared microfluidic chip. The sequencing library can be pumped into the flow cell, and bridge amplification and sequencing is performed. Multiple samples prepared by the library construction module, can be pooled and pumped into a single channel of a flow cell on the microchip, or the multiple samples can be pumped separately into separate channels of the flow cell. A single sample can be pumped into multiple channels of the flow cell. For example, the microchip shown in FIG. 21 can simultaneously prepare up to 24 samples, which can be pumped into 1, 2, 3, 4, 5 6, 7 8, 9, 10, 11, 12, 13, 14, 15, 16, 17, 18, 19, 20, 21, 22, 23, 24, or more than 24 flow cell channels. In an alternate implementation, the combined module can perform amplification on beads, such as emRCA or emulsion PCR (emPCR). The flow cell can contain a weir such that the beads can be pumped into the flow cell and trapped by the weir. In another embodiment, the flow cell could contain individual structures to trap beads after amplification, such as etched or molded wells, grooves, or other structures. In this manner, the integrated processing chip can incorporate additional functions.

Figure 25:
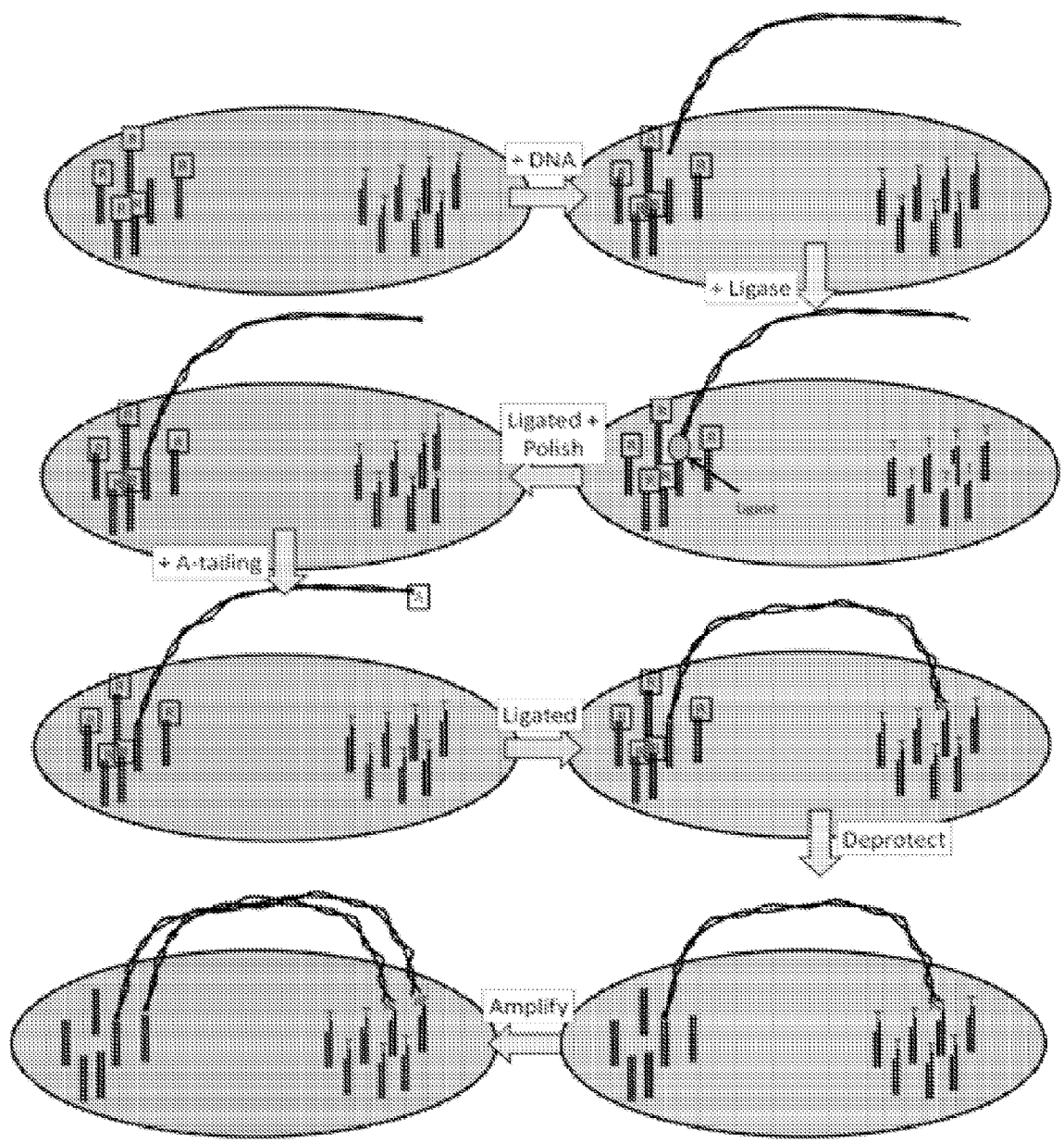
FIG. 25 shows a schematic for how to integrate library construction and amplification.

In some embodiments, library construction can be performed in an amplification module. In one embodiment, bridge amplification is performed on a solid substrate also used for library preparation, such as particles, paramagnetic beads or capillary channel surfaces. FIG. 25 shows one possible workflow that utilizes two sets of double-stranded oligonucleotides, each bound to a solid substrate. For clarity, the two sets are depicted as spatially separate left and right clusters. However, spatial separation is not necessary; for example, the two sets of oligonucleotides can be evenly mixed. In this example, the left set of oligonucleotides contain a blunt end. The right set of oligonucleotides can comprise a single base overhang, such as a T overhang. In some embodiments, a portion of the blunt ends of the left set of oligonucleotides are blocked with a removable blocking group. In some embodiments, a portion of the single base overhangs of the right set of oligonucleotides are blocked with a removable blocking group. The two sets of oligonucleotides may be blocked with the same or a different removable blocking group, and the blocking groups can be removed by the same or different means, such as by chemical cleavage, photocleavage, UV cleavage, heat-based cleavage or other methods. In some embodiments, the portion of blocked blunt ends is less than 5% or at least any of about 5%, 10%, 20%, 25%, 30%, 40%, 50%, 60%, 70%, 75%, 80%, 85%, 90%, 95%, 97%, 98%, 99, or 99.99%. In some embodiments, the portion of blocked single base overhangs is less than 5% or at least any of about 5%, 10%, 20%, 25%, 30%, 40%, 50%, 60%, 70%, 75%, 80%, 85%, 90%, 95%, 97%, 98%, or 99%, or about 100%.

To perform combined library preparation and sequencing, a DNA sample, which can optionally be fragmented or generated from reverse transcription, can be introduced. End-repair can be performed to generate blunt ends on the DNA sample, and the blunt ends ligated to any unprotected blunt ends of the left set of oligonucleotides. In another embodiment, end-repair is not performed, and only blunt ended DNA sample molecules will ligate to the blunt, unblocked oligonucleotides.

Preferably, a single DNA sample molecule is ligated per detectable region, which will allow detection of a single sequence. The detectable region can be, for example, a single well, bead, or site on a solid substrate that can be distinguished from other detectable regions. In the example depicted in FIG. 25, a detectable region can be the group of bound oligonucleotides. Preferably, only one end of a single DNA sample molecule is ligated during this ligation step, to avoid situations where the DNA sample molecule is ligated on either end to the two oligonucleotides of the same sequence, which can reduce sequencing accuracy by resulting in simultaneous elongation of both strands of the DNA sample molecule in subsequent steps. In some embodiments, a removable blocking group can be used to protect a portion of the left set of oligonucleotides from ligation. In some embodiments, the concentration of the DNA sample or of components of the ligation reaction can be controlled to reduce or otherwise adjust ligation rates.

The ligase can then be washed away. In some embodiments, a second polishing reaction can be performed to create a blunt end on free end of the ligated sample DNA. In some embodiments, the original end-repair step can be sufficient to generate blunt ends on both ends of the DNA sample molecule. An 'A-tailing' master mix can next be added and any unblocked blunt DNA fragments extended with an A. In some embodiments, removable blocking groups on the right set of oligonucleotides can prevent A-tailing of the single base overhang. After removing the A-tailing mix, ligase in master mix can again be added. Optionally, any blocking groups on the right set of oligonucleotides can be removed after removing the A-tailing mix. A-tailed overhangs of the ligated sample DNA can base pair with the T overhang of the right set of oligonucleotides to form a ligated sample DNA bridge between the left and right sets of oligonucleotides. The left set of oligonucleotides can then be unblocked. Optionally, the left set of oligonucleotides can be unblocked at the same time as the right set of oligonucleotides.

Next, PCR bridge amplification can be performed. FIG. 25 shows only the first round of amplification. In some embodiments, only one strand of the double-stranded oligonucleotides is linked to the solid substrate, and the left and right sets of oligonucleotides can be treated to remove the unbound strand, leaving single-stranded oligonucleotides suitable for acting as primers for subsequent amplification steps. In some embodiments, both strands of the oligonucleotides are bound to the solid substrate, and a denaturing step can be used to temporarily form single-stranded primers for amplification. In this method, the left and right sets of primers can include sequences for one or more of: an amplification primer, a sequencing primer, and any quality control sequences, such as barcode sequences, as taught in U.S. patent application Ser. No. 12/526,015.

Sequencing of the sample DNA can then be performed by any of the methods described herein. In some embodiments, one of the strands of the left or right set of oligonucleotides can be used as a sequencing primer. In other embodiments, a sequencing primer complementary to the primer strand can be added with the sequencing master mix. In some embodiments, one strand of the amplified sample DNA is removed from the solid substrate prior to sequencing. The method described herein has the advantages of combining library preparation, amplification, and sequencing on one device. In preferred embodiments, microfluidic pumps can be used to move liquids. In other embodiments, other mechanisms to move fluid are envisioned, such as other types of microfluidic pumps, hydraulic pumps, macrofluidic pumps, and so on. Similar workflows can be applied to library construction on particles, followed by emPCR or emRCA or other forms of amplification.

The size of the library construction module can be about or no more than any of about 0.1, 0.2, 0.5, 0.75, 1, 1.25, 1.5, 3, or 5 cubic feet. The library construction module can perform a library construction reaction in about or no more than any of about 5, 10, 15, 25, 50, 60, 90, 100, 120, 180, or 240 minutes.

The library construction module can include an integrated processing chip and/or one or more components exterior to the integrated processing chip. For example, the library construction module can include one or more reagent chambers that are not within the integrated processing chip. The one or more reagent chambers can be within a cartridge, or they can be one or more bottles or reagent cartridges. The integrated processing chip can be the same integrated processing chip used in the sample processing module, or a separated integrated processing chip.

An integrated processing chip can have one or more reaction chambers that are fluidically connected to reagent chambers and input chambers by fluidic channels within the integrated processing chip. The reaction chambers can be about 0.001-0.010 microliters, 0.010 to 0.025 microliters, 0.025 to 0.1 microliters, 0.1 to 0.5 microliters, 0.5-100 microliters, 1-50 microliters, e.g., 25 microliters in volume. The small volumes of the reaction chambers can allow preparation of sequencing libraries using small amounts of samples and reagents, which can improve the speed and cost-efficiency of the preparation steps. In some embodiments, incubation periods for a library preparation step can be reduced due to the small volumes of reactants used. In some embodiments, incubation periods for a library preparation step, such as end repair, A-tailing, ligation, or nucleotide synthesis can be less than about one hour, less than about 30 minutes, less than about 15 minutes, less than about 10 minutes, or less than about 5 minutes. The fluidic channels can have one or more pneumatically actuated valves and/or chambers for controlling the flow of liquids within the integrated chamber.

The integrated processing chip can be configured such that more than one library construction reaction can be performed in parallel. Parallel reaction chamber can share reagent chambers. The reagent chambers can be chambers for a ligation mix, adapters, vectors, exonucleases, a wash buffer, magnetic beads, streptavidin coated beads, and end repair enzymes. The reaction chambers can be in thermal contact with a heating/cooling device, e.g., a Peltier device.

The reaction chambers can also be fluidically connected to an outlet port that is fluidically connected to an amplification module.

Normalization Module

The function of the normalization module can be to provide an optimal library concentration to the sequencer. The concentration of each library can be measured, for example, using a fluorescently stained sample and an off-the-shelf fluorimeter. In other embodiments, the concentration can be measured by UV spectrophotometry, conductivity, or other methods known in the art. Each library can then be diluted accordingly and optionally pooled. The Normalization Module can also efficiently transfer fluids between the other cartridge modules.

Figure 22:
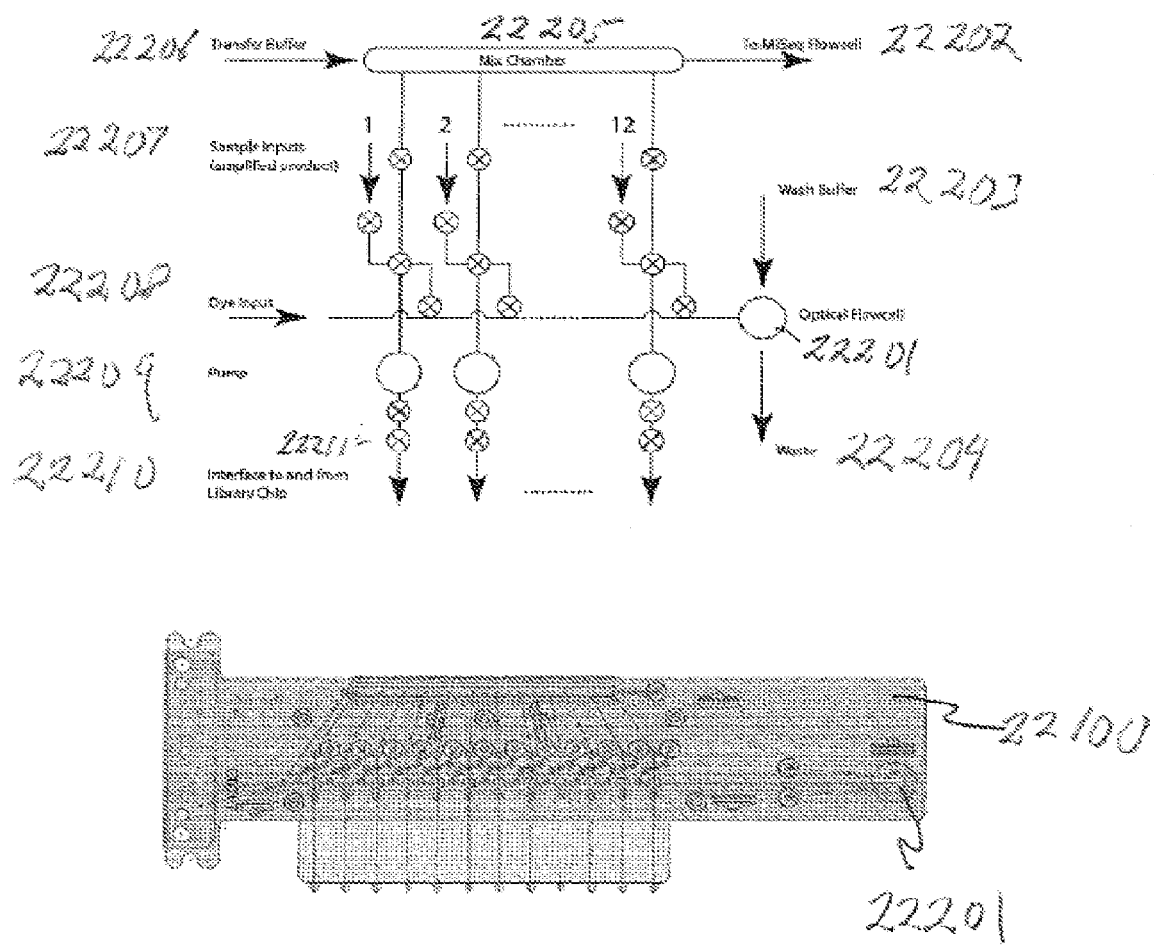
FIG. 22 shows an exemplary embodiment of a normalization module.

FIG. 22 shows a prototype design of the normalization cartridge 22100 that can process 12 sequencing library samples. The concentration of ds-DNA in each library is measured at the optical flowcell 22201 using the pump 22209 to withdraw aliquots of library samples that enter the Normalization module through interface 22210 and to withdraw dsDNA stain in buffer from Dye Input 22208, to mix and position the sample. The flowcell 22201 can be interrogated by a detector (not shown). The detector can be a fluorimeter, including a commercially available fluorimeter. After each measurement the optical flow cell is washed by a pressurized vial of wash buffer 22203 passed through the flow cell to waste 22204. This process can be carried out in series for each library. In some embodiments, multiple optical flow cells may be provided to simultaneously analyze more than one sequencing library.

Pooling of the libraries can be carried out by first pumping each library into mix chamber 22205. A controller can reference the measured dsDNA concentrations to modulate each of the pumping valves 22211 for each library appropriately, for example to produce a mixture comprising equal concentrations of each library. Transfer buffer 22206 can enter the mix chamber 22205 to dilute the libraries. Transfer buffer flow can also be used to push the pooled library to a sequencing module through port, channel or other fluidic connection 22202, such as a MiSeq flowcell.

The normalization module can provide an optimal library concentration to the amplification or sequencing module. The normalization module can quantify the concentration of the prepared sequencing library, dilute the library for optimal analysis, and combine multiple libraries together for simultaneous amplification or sequencing. In some embodiments, the normalization module can combine about or more than any of 2, 3, 4, 5, 6, 7, 8, 9, 10, 11, 12, 24, 48, 96, 192, or 384 libraries. In some embodiments, the normalization module can perform its function on the prepared sequencing libraries in less than about 5, 10, 15, 20, 25, or 30 minutes.

In some embodiments, the concentration of each library is measured using a fluorescently stained sample and a fluorimeter. Each can be diluted accordingly and then pooled. Preferably, the normalization module can also efficiently transfer fluids between the other modules. In some embodiments, the library quantification and/or dilution by the normalization module is accurate to within about 1% 2%, 3%, 5%, 6%, 7%, 8%, 9%, 10%, 15%, 20%, or 25%. In some embodiments, the normalization module is capable of automating dilution within a range of about or more than about 5-fold, 10-fold, 20-fold, 30-fold, 40-fold, 50-fold, 100-fold, 500-fold, 1000-fold, 2000-fold, 3000-fold, 4000-fold, 5000-fold, 6000-fold, 7000-fold, 8000-fold, 9000-fold, or 10000-fold.

In some embodiments, the module removes an aliquot from each sample, dilutes it with a dsDNA stain in buffer, and positions it in an aperture that is interrogated by an off-the-shelf fluorimeter. A schematic for one such normalization module is shown in FIG. 22. In one embodiment, these measurements are made serially, after which metered dilution and pooling is carried out in parallel.

Amplification Module

In some embodiments of the invention, the system can include an amplification module. The amplification module can amplify one or more nucleic acids from a sample. In some embodiments, the amplification module can include a device for creating a plurality of reaction chambers or sites. In some embodiments, the amplification module includes a plurality of reaction chambers, wells, or flow cells. The plurality of reaction chambers can be separated spatially using, for example, multiple reaction wells, an emulsion, or droplets. The module can be configured to perform a variety of amplification techniques, including emulsion amplification, emulsion rolling circle amplification, bridge PCR, and BEAMing. See, for example, Fan et al., "Highly parallel genomic assays." Nature Review Genetics 2006, 632-44. In some embodiments, the amplification module can perform its functions, e.g. amplifying the prepared sequencing libraries in less than or about 5, 10, 15, 20, 25, 30, 35, 40, 45, 60, 75, 90, 105, or 120 minutes. In some embodiments, the amplification module includes a device for creating an emulsion. The device can include ports for receiving an aqueous reaction mixture and an immiscible fluid. The device can mix the reaction mixture and the immiscible fluid to create an emulsion. The device can create an emulsion rolling circle amplification reaction. The device can place a template, e.g., circular templates, capture beads, random primers, and a DNA polymerase, e.g., phi29 DNA polymerase, in an emulsion of silicone oil. The emulsion can be created by vortexing or other methods to create an emulsion that packages these components into about $1\times10^3$, $1\times10^6$, $1\times10^9$, $1\times10^{12}$, or $1\times10^{15}$ isolated reaction environments. Each reaction environment can include about, no more than any of about, or more than any of about 0.1, 0.2, 0.3, 0.4, 0.5, 0.7, 1, 1.5, 2, 3, 4, or 5 nucleic acid template. Each reaction environment can include about, no more than any of about, or more than any of about 0.1, 0.2, 0.3, 0.4, 0.5, 0.7, 1, 1.5, 2, 3, 4, or 5 beads.

The amplification module can include one or more chambers for incubating the plurality of reaction environments at a pre-selected temperature. The one or more chambers can be in thermal contact with one or more heaters and/or coolers. The heaters and/or coolers can be thermoelectric coolers, Peltier devices, temperature controlled water, temperature controlled air as taught in U.S. Pat. No. 6,423,536, or other types of heat exchangers. In some embodiments, circulating water of different temperatures can process large volumes of emulsions.

After an amplification reaction, each reaction environment can include a bead that is coated with amplified nucleic acid. The amplification can include an amplification of $1\times10^3$, $1\times10^6$, $1\times10^9$, $1\times10^{12}$, or $1\times10^{15}$ times more nucleic acids. One strand of nucleic acid can be covalently linked to a bead.

In some embodiments, the amplification module is an emulsion rolling circle amplification module that can amplify single copy, single-stranded circularized nucleic acids into clonal populations using isothermal rolling circle amplification. In some embodiments, the amplification module is an emulsion PCR module that can amplify single copy, single-stranded circularized nucleic acids into clonal populations using PCR with temperature cycling.

In some embodiments, the amplification module is a bridge amplification module that can amplify single copy, single-stranded circularized nucleic acids into clonal populations on the surface of a flow cell. In other embodiments the amplification module is combined with the library construction module as shown in FIG. 25.

The size of the amplification module can be about or no more than any of about 0.1, 0.2, 0.5, 0.75, 1, 1.25, 1.5, 3, or 5 cubic feet. The amplification module can perform an amplification reaction in about or no more than any of about 5, 10, 15, 25, 50, 60, 90, 100, 120, 180, or 240 minutes.

The amplification module can have an inlet port for receiving a library of polynucleotides or DNA from the library construction module. The inlet port can be fluidically connected to a chamber or channel for creating an emulsion. The chamber or channel for creating an emulsion can be a macrofluidic mixer or injection mixer, described herein. The chamber or channel can be fluidically connected to a chamber that contains an immiscible liquid. The chamber or channel can also be fluidically connected to one or more reagent chambers. The reagent chambers can include reagent chambers for random primers, beads with specific primers, and DNA polymerases. Each reagent chamber can be integrated with the chamber or channel for creating an emulsion, or can be on a separate component. A separate chamber can be a component can be a cartridge, described herein. It can be the same cartridge used to store and supply reagents for the sample processing module, or any other module described herein. The chamber or channel for creating an emulsion can be fluidically connected to an amplification chamber. The amplification chamber can be thermally controlled. The thermal control can be by way of thermal contact to a thermoelectric cooler, or any other heating or cooling device. The amplification chamber can be about 0.010-1 microliters, 1-10 microliters, 10-1000 microliters, 1000-5000 microliter or e.g., about 100 microliters in volume.

The amplification chamber can be fluidically connected to an emulsion disruption chamber. The emulsion disruption chamber can have one or more inlets for a reagent to disrupt the emulsion. Emulsions can be disrupted using any technique known to one skilled in the art, for example, the emulsion can be disrupted by addition of a chemical that destabilizes the emulsion. See, for example, Kojima et al., "PCR amplification from single DNA molecules on magnetic beads in emulsion: application for high-throughput screening of transcription factor targets," Nucleic Acids Research 2005, e150.

Amplification modules can be built and used as described in U.S. Patent Publication 2003/0207267 and U.S. Pat. Nos. 5,854,033, 5,198,543, 5,576,204 and 5,001,050, which are incorporated herein by reference.

Sequencing Module

The invention provides for a sequencing module for sequencing nucleic acids. The sequencing module can be used to perform sequencing to a read length of more than any of about 500 bases from about or more than about 2 M clones. The sequencing module can be about 1 cubic feet in volume and have long read lengths. The sequencing module can perform any type of next generation sequencing, including an Illumina sequencer or next-next generation sequencing, such as a nanopore, zero mode optical waveguide, single molecule sequencing, electronic sequencing, or any other analytical sequencing modules. See, for example, Shendure et al., "Next-generation DNA sequencing," Nature Biotechnology, October 2008, 1135-1145; Metzker "Sequencing technologies—the next generation" Nature Reviews Genetics 11, 31-46 (January 2010); Fuller et al., and references therein, "The challenges of sequencing by synthesis." Nat Biotechnol. 2009 November; 27(11):1013-23; and Branton D. et al., and references therein, "The potential and challenges of nanopore sequencing." Nat Biotechnol. 2008 October; 26(10):1146-53.

The sequencing module can perform sequencing on unamplified samples. See, for example, Mamanova et al., "FRT-seq: amplification-free, strand-specific transcriptome sequencing," Nature Methods, January 2010, 130-132; Branton D. et al., and references therein. "The potential and challenges of nanopore sequencing." Nat Biotechnol. 2008 October; 26(10):1146-53; and Eid et. al. "Real Time DNA Sequencing from Single Polymerase Molecules", Science 323, 133-138.

In some embodiments, the sequencing module can sequence reads of up to any of about 25, 50, 100, 150, 200, 300, 400, 500, 600, 700, 800, 900, 1000, 10,000, 100,000, 1,000,000, 10,000,000, 100,000,000, or more bases in less than any of about 0.1, 0.5, 1, 2, 5, 10, 15, 30, 45, 60, 75, 90, 105, 120, 135, 150, 165, 180, 210, 240, 270, 300, 360, 420, 480, 540, 600, 660, 720, 780, 840, 900, 960, 1020, 1080, 1140, 1200, 1260, 1320, 1380, 1440, 1500, 1560, 1620, 1680, 1740, or 1800 minutes. In some embodiments, the sequencing module can sequence at least 120 Mb in 35 bp reads in less than or about 4 hours. In some embodiments, the sequencing module can sequence at least 10 Mb in reads of various lengths using zero mode waveguides in less than or about 15 min. In some embodiments, the sequencing module can sequence at least 680 Mb in 100 bp reads in less than or about 19 hours. In some embodiments, the sequencing module can sequence at least 1 Gb in 150 bp reads in less than or about 27 hours.

The sequencing module can be configured to perform any next generation sequencing reaction, sequencing by synthesis, zero mode waveguide, single molecule sequencing, nanopore sequencing or other type of sequencing. The sequencing module can be configured to perform real-time sequencing, sequencing by ligation, sequencing by hybridization, Sanger sequencing, reversible terminator-based sequencing, pyrosequencing, and/or super pyrosequencing. The sequencing module can have a plurality of reaction wells, sites, or flow cell channels for performing the sequencing reactions. The sequencing module can include one or more detectors for monitoring and/or measuring the sequencing reactions. The detectors can be CMOS sensors, CCD sensors, PMTs, pH measurement, quartz crystal microbalance, nanopore, and/or semiconductor sensors. The CMOS sensor can be a 2 megapixel CMOS image sensor. The CMOS sensor can be a 5 megapixel CMOS image sensor. The CMOS sensor can be a >10 megapixel CMOS image sensor. The CMOS image sensor can interrogate about, no more than any of about, or more than any of about 100×10$^3$, 500×10$^3$, 1000×10$^3$, 5000×10$^3$, 10000×10$^3$, 50000×10$^3$, 100000×10$^3$, or 1000000×10$^3$ wells or reaction environments. The detectors can be operably linked to the sequencing module by one or more fiber optic plates and/or cables. The sequencing module can be free of any lenses or lasers. In one embodiment, the CMOS image sensor is mated directly to a picoliter reaction plate.

The sequencing reaction can read about or at least about 25, 500, 1000, 1500, 2000, 2500, 3000, 5000, 10000, 100,000, 1,000,000, 10,000,000, or 100,000,000 base pairs. Improvements in read length can be made by improving the efficiency in nucleotide incorporation, removal of unincorporated or remaining nucleotides, and lowering the rate of dephasing of the polymerase for next generation sequencing.

The phasing rate can be greater than 0.997 and the prephasing rate can be lower than 0.003. This can produce a read length of greater than 500 base pairs at a better than 95, 97, 98, 99, or 99.9% accuracy.

The size of the sequencing module can be about or no more than any of about 0.01, 0.05, 0.1, 0.2, 0.5, 0.75, 1, 1.25, 1.5, 3, or 5 cubic feet. The sequencing module can perform the sequencing reaction in about or no more than any of about 0.1, 0.2, 0.5, 1, 2, 5, 10, 15, 25, 50, 100, 250, 500, 1000, 1500 or 2000 minutes.

The time for performing a sequencing reaction can be reduced by reducing cycle times for many methods. Reduction in cycle times can be achieved by delivering reagents in concentrated slugs. Concentrated slugs, or impulses, can be delivered using pneumatically actuated valves and pumps described herein.

The flow cell can be designed to trap beads with a weir. The beads can contain clonal amplification using emPCR or emRCA or other methods. To separate the signals, e.g., fluorescence, beads without amplicons can be added or the reaction diluted or optimized to have a lower percentage of beads having DNA and therefore giving sequencing signals to the detector. The weir allows fluids to be readily pumped or other moved over the beads that are captured at the weir. This has the advantage of greatly improved fluidic exchange compared to wells or zero mode waveguides, and can be used to position material over nanopores, channels, or other next-next generation detectors.

Sequencing modules are described generally in U.S. Patent Publication Nos. 2003/0198573, 2008/0262747, 2005/0181394, 2009/0087850, 2010/0093068, 2009/0325183, 2008/0131904, 2010/0137143, 2010/0035252, 2009/0026082 and in U.S. Pat. Nos. 7,170,050, 6,620,584, 7,486,865, 7,105,300, 7,244,567, 7,244,559, and 7,323,305.

Linear Arrays

In some embodiments of this invention, one or more of the modules comprise a linear array of chambers. The chambers can be separated by valves. The array of chambers also can comprise an array of valves, such as diaphragm valves, that comprise valve chambers. When the chambers comprise valves, the valve chambers or the diaphragm valves can function as reaction chambers and/or capture chambers. In a preferred embodiment, the array comprises at least five chambers or diaphragm valves fluidically connected in a series. The first and last valves in series are terminal valves, either or both of which can be connected to ports through which samples, solutions or reagents can be introduced into the array. Valves located between the terminal valves in the array can be intermediate valves. In linear arrays, the fluidic connections between chambers or valves of the array are typically unbranched. The array may be connected to multiple ports for addition or removal of reagents and products from the array. In certain embodiments, the terminal valves can each be connected to a bus or rail into which a plurality of ports feed. The terminal valves may also be connected to sample input or product output channels. The array may be connected to reagent reservoirs, other modules or to other arrays. Multiple arrays may be ganged, e.g. arranged in parallel and connected to the same set of bus, rail, or input/output channels or ports.

In some embodiments of this invention, one or more of the modules comprise a linear array of valve chambers, and said valve chambers may comprise diaphragm valves. Valve chambers can function as pumps, reaction chambers, and/or capture chambers. A linear array typically comprises at least five valve chambers fluidically connected in series, although fewer valve chambers may be used. Samples, solutions, or reagents can be introduced into the linear array via channel (s) situated at any point in the series. Fluidic connections between valve chambers are typically unbranched in linear arrays. In certain embodiments, terminal valve chambers are each connected to (a) buses or rails into which a plurality of channels feed, and (b) sample input/output channels.

Diaphragm valves used in linear arrays of this invention can be normally closed, pumping valves, normally open valves (e.g., having valve seats recessed with respect to a fluidic surface, such as a "domed" valve). Valves may or may not contain valve seats. The stroke volume is configured to be sufficient to hold enough liquid in which to perform a chemical reaction, or part of a chemical or biochemical reaction with later pooling of multiple reactions.

Chambers of a linear array of this invention can be of the same or different volumes. For example, a capture chamber of the array may be the same volume, larger, or smaller than a non-capture chamber of the array. If multiple linear arrays are ganged together, the chambers of one array may have the same or different volumes as the chambers of another array.

Figure 17:
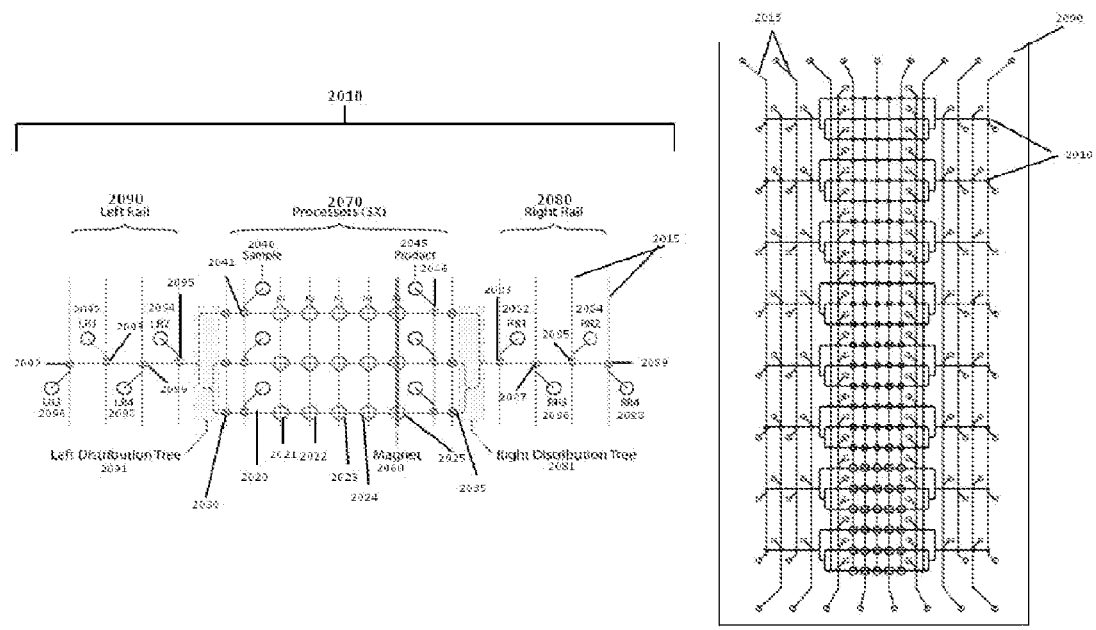
FIG. 17 shows a diagram of an exemplary linear module and an integrated processing chip that contains multiple linear modules.

FIG. 17 depicts a diagram for one exemplary embodiment of a linear array module. Chambers comprising valves P1, P2, P3, P4, and P5 (2021, 2022, 2023, 2024, and 2025, respectively) are arranged linearly along channel 2020. In this diagram, the linear array module 2010 comprises three linear arrays. However, linear modules may comprise 1, 2, 3, 4, 5, 6, 10 or less, 20 or less, 30 or less, 48 or less, 96 or less, or more than 96 linear arrays. Furthermore, the library preparation modules or other types of modules of this invention may comprise 1, 2, 5 or less, 10 or less, or more than 10 linear modules. In FIG. 17, device 2000 comprises eight modules, each containing three linear arrays. Within the depicted module, sets of multiple reagent reservoirs with individual control valves comprise reagent rails 2080 and 2090, which are fluidically connected to the right and left terminal ends of the linear arrays, respectively. The reagent rails are connected to each linear array through separate terminal isolation valves, e.g. 2030 and 2035. In the depicted embodiment, different linear modules contain chambers of different volumes. In other embodiments, different linear modules can contain chambers of the same volume. Additional sample and product reservoirs 2040 and 2045 can be also connected, via control valves, to the left and right ends of the linear arrays, respectively, or at many different positions. In embodiments wherein the apparatus comprises multiple sets of linear modules, one or more of the sample, product, waste, and reagent reservoirs may be shared across otherwise unconnected modules. In these embodiments, 2082, 2084, 2086, 2088, 2092, 2094, 2096, and 2098 are inlet ports fluidically connected to the shared reservoirs. In a different embodiment 2082, 2084, 2086, 2088, 2092, 2094, 2096, and 2098 are inlet ports fluidically connected to the channels, tubing or other fluidic paths that can deliver multiple boluses of liquids including reagents to the linear array. In some embodiments, not all of the reservoirs are shared across different modules. Additional isolation valves, e.g. 2030 and 2035, are located beyond the sample and product control valves to control fluid input and output from the linear modules. Control valves of the three linear arrays may be controlled independently or depend on the same control lines. In some embodiments, the valves of multiple linear modules can be simultaneously actuated by a single control line, such as with actuator lines 2015. A movable magnet 2060 can be arranged so that it can be positioned adjacent to the P5 or other chambers. In some embodiments, the magnet can be an electromagnet.

Linear arrays can be used to perform a wide variety of reactions, including but not limited to cell lysis, cDNA synthesis, end repair, addition of a vector, A-tailing, ligation, binding to beads, washing, exonuclease digestion, endonuclease digestion, chemical modification, chemical fragmentation, heat inactivation, PCR, RCA, real-time PCR, real-time RCA, and component separation. Examples of reactions are also found in FIGS. 10, 16, and 18. In some embodiments, a linear module can be used as multiple modules of the invention. For examples, a linear module can be shared across one or more of a sample loading module, a reagent loading module, a mixing module, a bead-loading module, a bead-capturing module, a bead-washing module, a bead-elution module, a collection module, and a waste disposal module. Reaction cascades can be performed without removing the reaction substrate from the linear array. Samples for reactions performed by linear array modules can comprise nucleic acids, proteins, amino acids, carbohydrates, lipids, or biologically active small molecules. Reagents can be added from ports fluidically connected to either end of the linear array. Reagents or products can also be removed from the linear array through the same or different ports. Reagent mixing can occur within a single chamber of the array, or between multiple chambers of the array. In some embodiments, mixing can be performed by pumping the contents of one or more chambers in a forward direction, in a reverse direction, or alternating between the two directions. Mixing can also be performed by adding a second reagent to a chamber partially filled with a first reagent. The chambers can be reused to perform multiple sequential reactions. The linear structure of the arrays also is advantageous by allowing simple assembly of multiple arrays on a chip or other structure for multiplexing of reactions.

In operation, different fluids to be mixed into a reaction fluid are introduced sequentially into different chambers in the array. The reactions are mixed by moving them through a common chamber or valve in the array. Optionally, the fluid is moved in both directions, e.g., back and forth, through a common chamber or valve in the array. The mixed reactions can then be incubated to allow a biochemical reaction to occur. Capture particles can be optionally introduced into a chamber in the array. The capture particles can be, for example, magnetically responsive particles carrying groups that bind a target analyte in the reaction solution or non-specific particles that bind a species, e.g., nucleic acids, proteins, basic proteins, neutral, and acid proteins, lipids, amino acids, carbohydrates, lipids, or biologically active small molecules; hydrophilic nucleic acids, proteins, lipids, amino acids, carbohydrates, lipids, or biologically active small molecules; hydrophobic nucleic acids, proteins, lipids, amino acids, carbohydrates, lipids, or biologically active small molecules. The particles and reaction product are mixed with another, again, by moving one or both of them at least once through a common valve in the array. The particles can be immobilized (e.g. with captured target analyte) in one or more chambers or valves, such as in a capture chamber. In one instance, if the particles are magnetically responsive particles, a magnetic force can be applied to the device to retain the particles in a capture chamber. A wash solution can be passed through the immobilized particles to remove unbound material. The bound reaction product can then be eluted from the particles, for example using an elution buffer. The eluted reaction product can be moved out of the array to one of the ports for collection, or can be retained in the array. This process can be reiterated with second, third, fourth or more reaction solutions to perform sequential biochemical reactions.

Other examples of methods to retain capture particles are well-known in the art. As one example, a weir or other structure can be used to retain beads by size in a capture chamber. Further, a target analyte can be retained by binding to other solid substrates. For example, a target analyte can be attached to an inner surface of a capture chamber coated with groups that bind the target analyte. Such groups may bind by charge, binding affinity, or hydrophobicity, among others. Such groups may also form a specific binding pair with a component of the target analyte. Examples of such binding pairs include biotin and streptavidin or avidin; an antibody and its epitope; complementary nucleic acid sequences, a peptide tag and a peptide binding domain, an aptamer and its binding partner, and a binding domain and its ligand. Specific examples of affinity tags usable in binding pairs used in this invention include GST, polyHis, FLAG, TAP, MBP, and GFP and its derivatives.

Because the reactions are performed in an unbranched array, reactions can easily be multiplexed. Linear arrays can be organized in a device in an array of arrays, e.g., in a grid. Such arrays can be ganged by connecting each of them to one or more common ports. For example, a rail to which a plurality of ports is connected can, itself, be connected to each of the linear arrays in the array of arrays. Thus, linear arrays of this invention can be used to reduce the footprint of devices designed to perform large numbers of reactions or reaction sequences in parallel. Multiplexed arrays may also be controlled in parallel using a shared actuation system, e.g. an actuation line that crosses valves across multiple linear arrays.

The linear array can be used to mix samples. In some embodiments, the linear array can be used to mix any number of samples, for example by sequentially adding reagents to be mixed through one or both terminals of the linear array. Different reagents can be added from different ports. In some embodiments, different reagents may be added from the same port. In some embodiments, the module can include N mixing chambers to perform at least N mixing reactions. Reagents for the N mixing reactions can be introduced via N+1 inlets or stored in N+1 reagent reservoirs. In some embodiments, some of the mixing reactions can use at least one shared reagent. In some embodiments, N is at least one of 2, 3, 4, 5, 6, 7, 8, 9, 10, 20, 48, 96 or more. In some embodiments, at least a portion or component of the mixed reaction can be removed from the linear array, such as through an outlet port or reservoir. In some embodiments, an inlet port or reservoir can also serve as an outlet port/reservoir. Preferably, the linear array combines five or more chambers. Such an arrangement is particularly advantageous because it allows two sequential mixing steps of equal volumes.

Reagents for mixing reactions as embodied by this invention can be of various volumes. For example, a reagent aliquot can be less than the volume of a chamber, equal to the volume of a chamber, or more than the volume of a chamber. In some embodiments, a first reagent can be loaded into two or more chambers of a linear array and mixed with a second reagent that fills one or more chambers.

In some embodiments, the linear module comprises a breadboard which can comprise a base to support or hold in place a chip containing the linear arrays. The breadboard can comprise pneumatic ports connected to the pneumatic control lines in an actuation layer of the microfluidic chip. The breadboard can also comprise a manifold, such as a macrofluidic manifold, that interfaces with the linear module and contains sample and/or reagent wells fluidically connected to inlets on the linear module. An upper frame can be positioned above the manifold and chip and affixed to the base to hold the manifold against the chip. The upper frame can comprise an opening to allow access to the reagent wells of the manifold. In some embodiments, the upper frame may comprise a removable cover layer to allow access to the manifold. In some embodiments, the linear array module may contain a robot that may supply reagents, samples, wash solutions or other liquids to the linear array. The linear can have spacing among inlets to interface with standard microtiter plate spacing, such as 9 mm spacing.

The linear array can be used to prepare sequencing libraries, for example for use with commercially available sequencers, such as those using sequencing by synthesis, nanopore detection, pyrosequencing, semiconductor sequencing, exonuclease-based sequencing, or other methods of sequencing as described herein. For example, in a first reaction, reagents for end repair, such as T4 PNK and T4 polymerase, can be loaded in P2 from a master mix reservoir MM1. The target nucleic acids can then be loaded from the sample reservoir into P1. A loading step can be preceded by a priming step, which can reduce bubbles or remove contaminants from the chambers, valves, or channels. The contents of P1 and P2 can then be mixed by the sequential steps of: simultaneously opening P3 and closing P1 to pump the reaction into P2 and P3; simultaneously opening P4 and closing P2 to pump the reaction into P3 and P4; simultaneously opening P2 and closing P4 to pump the reaction into P2 and P3; and simultaneously opening P1 and closing P3 to pump the reaction into P1 and P2. Pumping can also be achieved by sequentially opening and closing appropriate chambers. During the course of forward and reverse pumping, the contents of the two chambers are mixed. The mixed reaction is then incubated to perform the end repair reaction. The product nucleic acids can then be purified from the reaction by binding to beads or particles.

To purify nucleic acids from solution, a slurry containing magnetic beads can be loaded from a bead reservoir into P3 and P4. The bead slurry can then be mixed with the product solution by simultaneously opening P5 and closing P1 to pump the mixture into P2-P5, then simultaneously opening P1 and closing P5 to pump the mixture into P1-P4. Additional mixing can be performed by repeating these forward and reverse pumping steps. The magnet can then be brought adjacent to P5, and the mixed reaction containing nucleic acids bound to beads can be pumped out through the right end of the linear array. The magnetic beads can be retained in P5 by the magnet while the remaining, nucleic acid-free solution is removed from the linear arrays and output through a waste reservoir. The beads can then be washed by pumping a wash solution from a wash reservoir from the right end of the linear arrays, through the beads retained in P5, and out through the left end of the linear arrays to a waste reservoir. The washed nucleic acids can then be eluted from the beads. An elution buffer can be loaded into P5, and the magnet moved away from P5, Mixing can occur through reverse and forward pumping of the reaction from P5 to P4 and back. The magnet can then be moved back to be adjacent to P5. The elution solution can then be pumped from P5 to P3, P2, or P1 while retaining the bead-bound nucleic acids in P5. The beads can then be removed by pumping a solution into P5, mixing as described for the elution step, and then removing the bead slurry out through the right end of the linear arrays into a waste reservoir. Alternatively, purification can be performed to remove enzymes from the mixed reaction by using beads or particles that bind selectively to the target enzymes, such as through affinity tags. In this case, after mixing, the solution containing the nucleic acids can be retained in the linear arrays, and the enzymes bound to the beads removed from the linear arrays. Nucleic acids, enzymes, or other reaction components can bind to a solid substrate through affinity binding, charged interactions, or hydrophobic interactions.

After the purification step, the nucleic acid product is retained in a chamber within the linear array. Thus, as will be apparent to one skilled in the art, the linear array can be used to perform any number of sequential reactions without the need to remove the reaction from the linear array during a reaction step or between reaction steps. For example, the end repair step can be followed by an A-tailing step, followed by ligation to an adapter oligomer to generate libraries for sequencing. Optionally, the final purification step can comprise using two sequential bead-based purifications, such as using SPRI beads to select a specific range of polynucleotide lengths. In some embodiments, the linear arrays can be used to perform nucleic acid amplification steps on the prepared nucleic acid libraries, including emulsion PCR, bridge amplification, or rolling circle PCR. In other embodiments, amplification can be performed in a separate amplification module.

Figure 18:
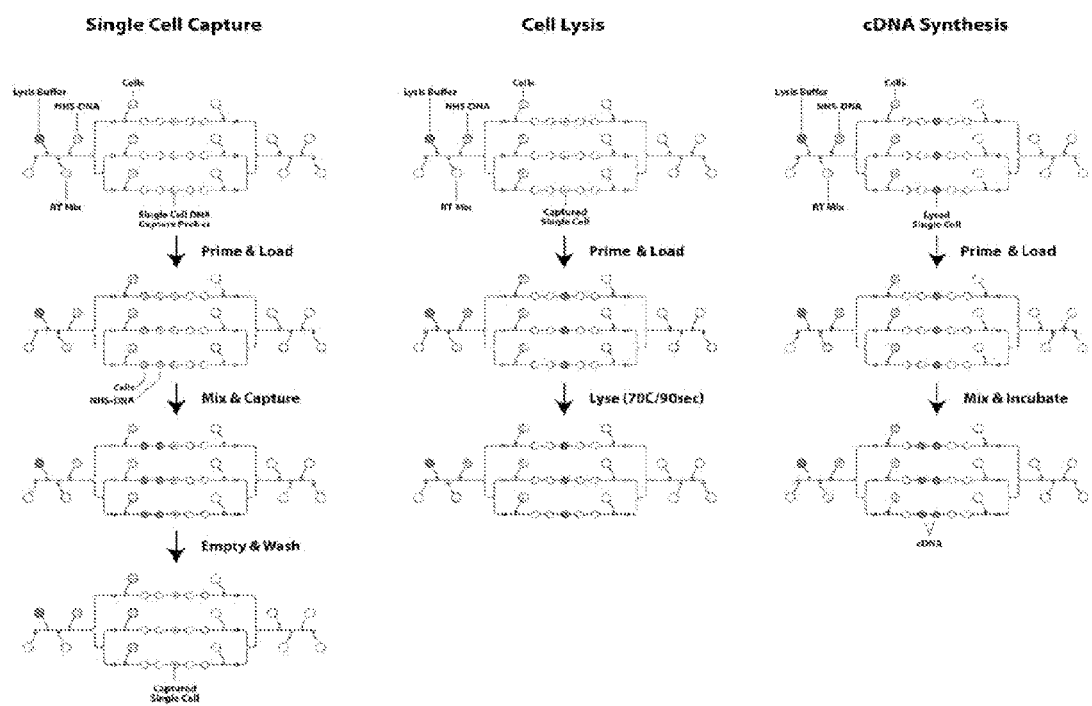
FIG. 18 shows schematics of steps for various functions that can be performed by a linear module.

In another embodiment, linear arrays can be used to produce cDNA from single cells, as depicted in FIG. 18. For example, single cells can be captured within a capture chamber of a linear array by using a capture chamber containing a single cell capture probe. Flowing a sample mixture comprising multiple cells can allow a single cell to bind and be retained in the capture chamber, after the rest of the sample mixture is removed from the linear array. Next, lysis buffer can be added to the capture chamber, and mixing by forward and reverse pumping performed to lyse the single cell. Nucleic acids from the single cell, such as the mRNA transcripts, can be purified by bead binding and elution as described herein. A reaction comprising a reverse transcriptase and other reagents can then be added to the purified nucleic acids and mixed to perform cDNA synthesis. After cDNA first strand synthesis, the nucleic acids can be re-purified and a reaction mixture suitable for second strand synthesis added to the sample mixture. In other embodiments, the reverse transcriptase or other enzymes or affinity probes can be affinity-tagged and the reverse transcriptase removed by binding to particles, such as magnetic particles. In some embodiments, first or second strand DNA synthesis may include affinity-labeled nucleotides in the reaction mixture, resulting in labeled cDNA that can be purified by affinity binding, such as to magnetic particles.

The fluidic devices of this invention can comprise microfluidic elements, such as microfluidic channels, microfluidic chambers and microvalves. The devices also can comprise macrofluidic channels, chambers and valves, alone or integrated with microfluidic components. The devices also can comprise mesofluidic channels, chambers and valves, alone or integrated with microfluidic components. A microfluidic channel has at least one cross sectional dimension no greater than 500 microns, no greater than 400 microns, no greater than 300 microns or no greater than 250 microns, e.g., between 1 micron and 500 microns. A microfluidic flow path is a flow path between two vents in communication with atmosphere and configured so that a sphere having a diameter greater than 500 microns could not fit in at least one point in the flow path. A mesofluidic channel has at least one cross-sectional dimension greater than 500 microns and less than 5 mm.

A linear array comprising microfluidic elements of this invention can be of any length, preferably less than about 30 mm in length, more preferably less than about 10 mm, and most preferably less than about 5 mm in length. A macrofluidic channel has at least one cross sectional dimension greater than 500 microns.

A non-microfluidic volume as used herein refers to a volume of at least 5 microliters, at least 10 microliters, at least 100 microliters and least 250 microliters, at least 500 microliters, at least 1 milliliter at least 10 milliliters, or at least 100 milliliters. The linear array can also process beads that have been used to extract large volumes such as 1 milliliter, 2 milliliter, 5 milliliter, 10 milliliter, 50 milliliters, 100 milliliters, 500 milliliters, 1 liter and larger volumes.

System

A fluidic system used in the invention can comprise a fluidic assembly and an actuation assembly. The fluidic assembly can comprise (1) elements to engage and hold the fluidic portion of a microfluidic device that comprises fluidic conduits, (2) a fluidic manifold configured to mate or align with ports on the microfluidic device and to deliver fluid into the fluidic conduits and (3) a fluid delivery assembly, such as a robot or a pump, configured to deliver fluids to the fluidics manifold or to the microfluidic conduits directly. The actuation assembly can comprise (1) elements to engage and hold the actuation portion of a microfluidic device that comprises actuation conduits, (2) an actuation manifold configured to mate or align with ports on the microfluidic device and to deliver actuant into the actuation conduits microfluidic device; and (3) an actuant delivery assembly, configured to deliver fluids to the actuation manifold or to the actuation conduits directly. The actuant delivery assembly can comprise a source of positive or negative pressure and can be connected to the actuation conduits through transmission lines. The instrument can also comprise accessory assemblies. One such assembly is a temperature controller configured to control temperature of a fluid in a fluidic conduit. Another is a source of magnetic force, such as a permanent or electromagnet, configured to apply magnetic force to containers on the instrument that can comprise, for example, particles responsive to magnetic force. Another is an analytic assembly, for example an assembly configured to receive a sample from the fluidic assembly and perform a procedure such as capillary electrophoresis that aids detection of separate species in a sample. Another is a detector, e.g., an optical assembly, to detect analytes in the instrument, for example fluorescent or luminescent species. The instrument also can comprise a control unit configured to automatically operate various assemblies. The control unit can comprise a computer comprising code or logic that operates assemblies by, for example, executing sequences of steps used in procedure for which the instrument is adapted.

An actuation system can control actuation of the valves. An actuation system can, for example, comprise one or more solenoid valves that, when appropriately positioned, put an actuation conduit in communication with a source of positive pressure compared with ambient and/or a source of negative pressure compared with ambient. In a solenoid valve electric current through a solenoid actuates movement of a magnet within the solenoid that comprises ports that can be switched between selected inlet and outlet ports, thereby directing a fluid (gas or liquid) along an open path, or preventing fluid flow at a stop. Typically the magnet is spring-biased to hold the valve in a selected position when not being actuated. The actuation system can be controlled by a control system, such as a computer programmed to operate the solenoid valves and the pressure sources.

A fluidics robot, such as a Tecan robot, can robotically add fluid to ports in the fluidics layer. The actuation layer can be engaged with a manifold, such as a pneumatic manifold, that mates ports in the pneumatic layer with a source of positive or negative pressure. In certain embodiments, a single pneumatic channel operates valves in a plurality of different fluidic conduits in parallel. Then, by pneumatically actuating the valves in various sequences, liquids can be pumped between chambers. The chambers can be provided with reagents to allow reactions.

The full integration from sample-to-sequence using next-next generation sequencer modules such as nanopores and single molecule sequencing, such as Helicos, can simplify the sample preparation requirements to lysis and nucleic acid purification with a possible sizing step or fragmentation depending on the sequencing module performance and will result in not having to perform the extended workflows required by next generation sequencing. The Sample Processing Module and the Sequencing module can be integrated to form a complete easy to use, fully automated sample-to-answer system.

Computer and Software

Figure 16:
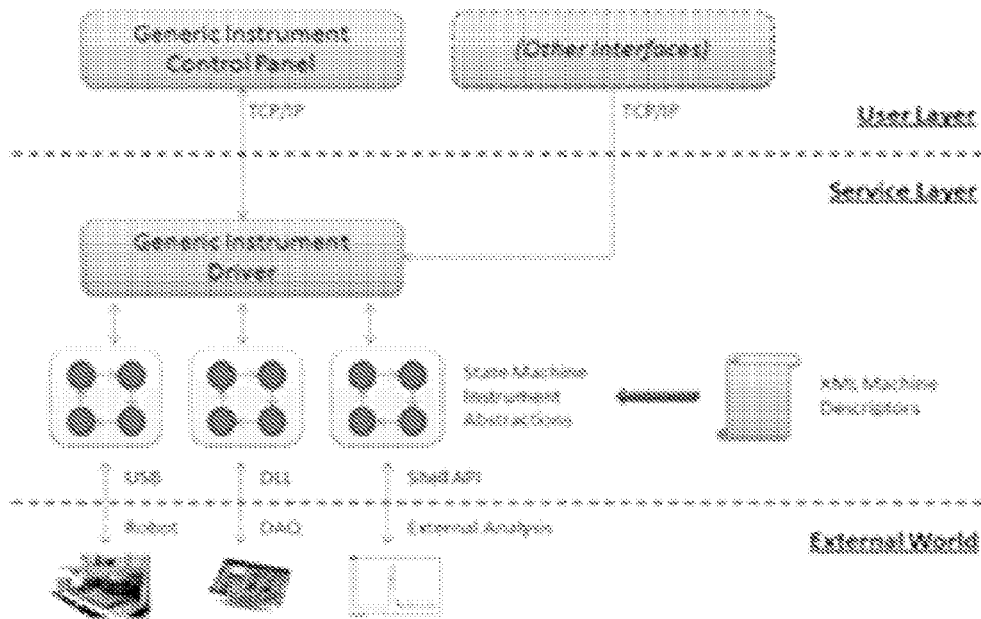
FIG. 16 shows a schematic of a computer logic.

The one or more modules of the system can be controlled and/or automated by an electronic processing and control device such as a computer and software. The computer module can display a user interface for receiving control parameters and for returning results from the sequencing analysis. The user interface can also be used to follow the steps performed by the modules of the system, including in real-time. In some embodiments, the user interface can interact with the control software to set, modify, or end a process on one or more modules of the system. The control software, also referred to as DevLink herein, can control and coordinate all modules and submodules for full process integration and automation. The software can be implemented in C# using Microsoft's .NET Framework. The software can use a dual layer architecture, as shown in FIG. 16. The critical instrumentation control can occur in an isolated, "persistent service layer" executable that protects the hardware resources (memory, threads, file handles, etc.) from volatile "user-layer" graphical environments.

In one embodiment, the instrument comprises a computer that can be programmed to introduce the samples and reagents into the isolated region and then move them into a recovery region after the reaction is complete to permit withdrawal of the sample for subsequent analysis. In another embodiment, the microfluidic device can be programmed to move the reacted sample into a reservoir or a fluid zone and add additional reaction reagents and reintroduce the sample into the isolated region for additional reactions. In other embodiments, the microfluidic device can be programmed to move the reacted sample into a reservoir or a fluid zone and add capture reagents and then move the sample into a capture region for the physical separation of analytes of interest; e.g., through the use of a magnetic field to capture magnetic beads coated with binding moieties. In other embodiments, the microfluidic device can be programmed to move the reacted sample into a reservoir or a fluid stream and add detection reagents or moieties and then move the sample into a recovery region to permit withdrawal of the sample for subsequent analysis. In some embodiments, the computer can control a pneumatic actuator to control pumps and valves of microfluidic modules within the system, including within linear modules. In some embodiments, the computer can control a magnetic actuator to move a magnetic field to desired positions to interact with fluids, devices, submodules, or modules of the system. In some embodiments, the computer can control the system to transport a nucleic acid sample from one module to another module, such as by controlling a pump to move a sample out of one module through an outlet port and into a second module through a fluidically connected input port. In some embodiments, the computer can bring two modules into fluidic communication, for example by moving one or both of the modules or by moving a connecting structure between the two modules into fluidic communication with one or both modules. A detection device, such as laser induced fluorescence Raman, Plasmon resonance, immunocapture, mass spectroscopy, and DNA analysis devices known in the art, can be used to interrogate the sample in a chamber or valve, within the channel of the shelf region or within another part of the microfluidic device. See, e.g., WO 2008/115626 (Jovanovich). A microfluidic device having a monolithic membrane is one example of a particularly suitable device for implementing a detection system on a chip. According to various embodiments, the detection system can also include immunocapture and DNA analysis mechanisms such as polymerase chain reaction (PCR), and capillary electrophoresis (CE) mechanisms.

The system can be programmed to perform a variety of enzymatic and non enzymatic reactions, such as reactions for DNA sequencing or cell lysis using high pH solutions. Such reactions can include polynucleotide fragmentation, end repair of nucleic acid fragments, exonuclease digestion, endonuclease digestion, A-tailing and adaptor ligation. In some embodiments, the system comprises a computer readable medium comprising instructions for a computer-implemented method of controlling various components of the system. In some embodiments, the system comprises a computer readable medium comprising instructions for a computer-implemented method of collecting or analyzing data gathered by various components of the system.

Running the software can include a three-stage process of factoring, wrapping and scripting. "Factoring" can break the system up into stand-alone components, "wrapping" can normalize the communications of each factored device. "Scripting" can implement high level work-flow on top of the instrument wrappers.

Software for the integrated system can be written with this approach using DevLink core libraries. The workflow script can contain all needed control parameters for each module and can display an interface to an end-user to manipulate the control parameters as necessary. Error handling and recovery can be implemented in a master script that can utilize information from all parts of the system to properly evaluate a decision tree.

In some embodiments, the computer and software can be used to collect and store data from various detection devices. Such data can include sequencing data as well as information regarding quality control measurements or intermediate products, such as for tracking progression or for troubleshooting.

In some embodiments, after sequence data has been collected, the data can be automatically converted to a standard FASTA sequence format. The master control script can delegate data archival and processing to a custom "Numerical Analysis" engine that performs pattern recognition against known target sequences of interest such as toxins, cloning vectors, antibiotic resistance, identity, genetic traits, etc. In some embodiments, the data can be analyzed to generate confidence values for the data. The computer and software can also be used to combine or analyze multiple data sets, such as from multiple samples or from different sample runs. Final result presentation can be delegated to a report generator that can runs under automated script control. In some embodiments, raw or partially processed data can be saved or transferred to another location for processing, analysis, reporting, or database storage or query. In some embodiments, data, including raw data, converted data, or reports generated from such data, can be imported or exported across government borders.

Methods for Integrated Analysis

The invention provides methods for performing integrated analysis on a sample. The integrated analysis can be automated such that no user intervention is required after initiating the analysis. In some embodiments, a user can select desired analysis parameters and input a sample, and the sample is sequenced without further user interaction. The sequence data can be returned in FASTA format. The sample can be an unpurified sample, a tissue sample, an environmental sample, a clinical sample, or any other sample described herein. The sequence results can be produced in about or no more than any of about 0.01, 0.02, 0.05, 0.1, 0.1, 0.2, 0.5, 1, 2, 3, 4, 5, 7, 8, 9, 10, 12, 14, 16, 18, 20, 22, 24, 36, or 48 hours.

The integrated analysis of the sample can include one or more processing steps. The processing steps can include lysing cells, isolating and/or purifying nucleic acids, modifying nucleic acids (including fragmenting nucleic acids, cDNA synthesis, creating a nucleotide library, and amplifying the nucleotide library), and sequencing. In some embodiments, the processing steps also include transferring materials from one module or submodule to another module or submodule. The transferring step can be from a sample processing module to a library construction module, from a library construction module to an amplification module, from an amplification module to a sequencing module, or from a submodule of one of the above mentioned modules to a downstream submodule. These processing steps can be controlled and/or automated by a computer or by computer logic.

In some embodiments, isolating and modifying nucleic acids can be performed by a first module. The first module can include a sample processing module, a library creation module, and an amplification module. Sequencing can be performed by a second module, which can include a sequencing module. As described herein, modules can be fluidically connected to each other and controlled such that various reactions can be performed and fluids moved within and amongst the modules in an automated manner.

Sample Processing

The invention provides for methods of sample processing and preparation. Sample preparation can be performed automatically using the devices described herein. For example, a sample can be input to a device by a user, and the device can use a computer-implemented method to interpret instructions to perform the sample preparation. Such instructions can be preset by a manufacturer, selected by a user, and/or given by a user. In some embodiments of the invention, a user can input sample volume, sample type, and estimated sample amount. The sample may be, for example, a tissue sample, fluid sample, environmental sample, forensic sample, cheek swab, or cell culture. The sample can be modified by a lysing procedure configured to lyse cells, spores, or any other material. The lysing process can release or expose nucleic acids. Nucleic acids in the sample, whether released by lysis or not, can be purified or isolated using a purification procedure. The purification procedure can include immobilization of nucleic acids to a solid substrate either specifically by hybridization or non-specifically Immobilized nucleic acids can be washed and then released using an elution buffer. Isolated and/or purified nucleic acids can be subjected to a fragmenting procedure. The fragmenting procedure can include any procedure described herein or generally known in the art to alter the size distribution of the nucleic acids in the sample. Fragmentation can be achieved by, for example, enzymatic cleavage, by sonication, or by mechanical shearing. The length of fragmented nucleic acids can be on average less than about 50 base pairs, less than about 100 base pairs, less than about 200 base pairs, less than about 400 base pairs, less than about 600 base pairs, less than about 1000 base pairs, less than about 2000 base pairs, or longer than about 2000 base pairs. Fragmented nucleic acids can then be transferred to a library construction module if desired.

Library Construction

A library of nucleic acids can be constructed using the methods of the invention. A library construction module can receive fragmented nucleic acids and perform one or more reactions for creating the library of nucleic acids. Steps for producing and sequencing a library of nucleic acid templates are shown in FIG. 19. Another set of steps for creating a library of nucleic acid templates is shown in FIG. 10.

In one embodiment, fragmented nucleic acids can be subjected to end repair. End-repaired genomic fragments can be ligated to a vector that has an affinity tag. In some embodiments, the vector can contain specific restriction enzyme recognition sites, sequences complementary to primers for amplification or sequencing, or other sequences of use in the invention. The ligated vector and fragmented nucleic acids can form a circularized nucleic acid template. Tagged nucleic acids can be immobilized to beads. Non-circularized nucleic acid templates can be digested by an exonuclease. Exonuclease can then be heat inactivated, leaving single-stranded circularized nucleic acid templates.

In another embodiment, fragmented nucleic acids can be subjected to end repair. End-repaired fragments can be A-tailed, and the resulting A-tailed fragments ligated to an adapter sequence. The adapter sequence can include an affinity tag. The adapter sequence can contain a sequence to allow specific binding to a substrate, or for complementary binding to a primer for amplification or sequencing or for indexing pooled samples. The resulting nucleic acids can be purified by affinity binding or SPRI. In one embodiment, multiple steps of SPRI purification can be performed to isolate a population of ligated, A-tailed fragments of an appropriate size for subsequent amplification as described herein.

In some embodiments, libraries are constructed from RNA samples. In these embodiments, library construction can include reverse transcription of RNA samples to form cDNA. The cDNA can be further used as a template for DNA polymerase and amplification to form double-stranded DNA. Subsequent steps of library construction can then be performed as described herein.

In some embodiments, library construction can incorporate affinity tags into the library. Affinity tags can be, for example, biotin, GST, MBP, or other labels as described herein. Affinity tags can be incorporated during ligation steps, such as to a labeled vector or adapter as described supra. Affinity tags can also be incorporated during A-tailing, such as by using biotinylated dATP, or during DNA synthesis, such as by using a biotinylated nucleotide during either polymerization step when preparing libraries from RNA samples.

Sequencing Library Preparation Using Labeled Nucleotides

In some embodiments, libraries are prepared from short RNA samples, such as sRNA, siRNA or miRNA. In such cases, the adapters used to generate libraries are approximately the same length as the samples. The resulting ligated molecules are difficult to separate from the adapters by size, which can interfere with subsequent amplification and sequencing. Thus, to generate sequencing libraries from short RNA samples, it can be advantageous to label the library precursors using biotinylated nucleotides. Labels other than biotin may also be used, as are well known in the art or described herein. Labeled nucleotides can be incorporated during reverse transcription, or during synthesis of the second DNA strand complementary to the initial cDNA. In another embodiment, labeled dATP can be incorporated during an A-tailing step or during end repair or polishing steps. Labeled nucleotides are easily separable from polynucleotides using methods known in the art, such as by using size-based separation. The labeled library precursors can then be ligated to the adapter molecules, for example using T4 ligase. After ligation, biotinylated library molecules can be separated from unlabeled adapters by binding to, for example, streptavidin-labeled beads as described herein. In some embodiments, size-based separations can then be performed. In some embodiments, subsequent size-based separation is not necessary before amplification. The methods described herein can also be used for generating libraries from longer RNA samples, or from DNA samples. The methods are particularly advantageous for generating libraries containing short sequences to be sequenced, regardless of the type of nucleic acid from which the libraries are derived. In some embodiments, the steps are performed in a microfluidic device, such as a linear array or linear module. Sequencing libraries produced in this manner can be amplified or sequenced by any of the methods described herein, such as by transferring the labeled library to an amplification or sequencing module.

Solid Phase Immobilization

In some embodiments, the different steps of library preparation can be performed without purifying the intermediate nucleic acid products from the reaction mixture. This allows for a more simplified workflow during sequencing library preparation, which can aid automation. Libraries prepared by these methods may be derived from samples containing RNA, DNA, or a combination thereof. In some embodiments, instead of purifying nucleic acid intermediates from the reaction mixtures, the enzymes used for the preparation steps are inactivated or removed from the mixture after use. Removing or inactivating the enzymes can allow the next step in library preparation to proceed without interference from enzymes used in prior steps. In one embodiment, an enzyme used for end-repair and A-tailing is labeled with an affinity tag. In another embodiment, an enzyme used for nucleic acid synthesis is labeled with an affinity tag. After the end-repair, A-tailing, or other enzymatic step, the enzyme can be bound to a solid substrate that contains a specific binding partner for the affinity tag. In some embodiments, the enzyme can also be bound to a solid substrate before or during the reaction. Solid substrates can include but are not limited to particles, magnetic particles, or surfaces of chambers, channels or other components of a library preparation module. The list of suitable affinity tag-binding partner pairs includes but is not limited to: biotin and avidin or a related molecule; an epitope and an antibody; a polyHis tag and a His-binding moiety such as Ni-NTA, MBP and amylose; a small peptide label and a corresponding peptide-binding domain, or other binding pairs as described herein.

Examples of enzymes that can be tagged for the methods of this invention include but are not limited to kinases such as PNK; polymerases including those from T4, Phi29, *E. coli, T. aquaticus,* or *P. furiosus* and their derivatives, such as Klenow fragment; T4 ligase and other ligases; restriction enzymes; phosphatases such as T4 phosphatase; and exonucleases.

In one embodiment, the labeled enzymes are bound to magnetic beads. The bead-bound enzymes can then be removed from the rest of the reaction mixture, such as by centrifugation, size separation (such as using a weir in a microfluidic device), or, in the case of magnetic or paramagnetic beads, by the use of a magnetic force. In embodiments where the enzyme is bound to a wall, channel, or other non-particle substrate, the reaction mixture can be removed from the chamber where the enzyme is bound. The resulting mixture is thus depleted of active enzyme and can be directly used in the next step of library preparation. In some embodiments, the volume of the depleted mixture can be reduced before the next step of library preparation. In some embodiments, all the enzymes used during library preparation can be labeled and added or depleted by the methods described herein. In some embodiments, all but the last step of library preparation uses labeled enzymes and the depletion methods described herein. Labeled enzymes may comprise the same affinity tag or different affinity tags. In some embodiments, some enzymes are depleted after their use in a library preparation step while other library preparation steps are followed by purifying the nucleic acid product from the reaction mixture, such as by using SPRI. In some embodiments, an enzyme used in a library preparation step is inactivated, such as by heat inactivation.

After library generation, the library can be further amplified prior to sequencing. In some embodiments, the library can be directly used for sequencing as described herein, without the need for an amplification step.

Amplification

The invention provides methods for performing amplification reactions. In some embodiments, the amplification reaction can be an amplification reaction on an isolated nucleic acid molecule. The amplification reaction can be performed in a reaction site. A reaction site can contain a single amplification reaction, or can contain multiple amplification reactions. The reaction site can be a droplet. The droplet can be a droplet in an emulsion, as described herein. In some embodiments, the amplification site is a reaction well, such as a nanowell or a picowell. In some embodiments, the amplification site is a microfluidic structure, such as a microfluidic chamber or channel, surface, or membrane. In some embodiments, the amplification site is a flow cell, or is located within a flow cell. The reaction site can contain about one nucleic acid template, a bead with primers, random primers, and polymerases. In some embodiments, amplification can be performed by polymerization or by sequential ligation. The amplification reaction can be performed at one temperature, or at a plurality of temperatures. The droplet or reaction well can be heated or cooled by one or more heat exchangers, heaters, and/or coolers. The amplified nucleic acids can be bound to a solid phase, e.g., a bead, particle, nanoparticle, channel, membrane, and/or elastomer. The amplified and/or bound nucleic acids can then be delivered to a sequencing reaction as isolated and amplified nucleic acids. In some embodiments, the amplified and/or bound nucleic acids from a plurality of reaction environments (e.g., reaction wells or droplets) are combined and then delivered to a sequencing device. In one embodiment, amplification is performed on a bead isolated within a droplet so that the population of amplified nucleic acids is also bound to the bead. After amplification, the droplets can be combined while the different populations of amplified nucleic acid remain bound to different beads. In one embodiment, amplification is performed by immobilizing individual molecules at different locations on the surface of a chamber or flow cell. Two primers can be bound to the surface of the chamber or flow cell, one complementary to one end of the target nucleic acid, and one that contains a sequence at the other end of the target nucleic acid. Amplification occurs when the free end of the template molecule binds to the complementary primer. The resulting product molecule is then denatured, and both product strands used in the next amplification cycle. After multiple amplification cycles, the resulting products are localized around the original binding site of the first target molecule. The amplification process using any of the methods described herein can be performed by an amplification module. The amplification process can be combined with the library construction process as shown in FIG. 25. The amplification step can be automated, similar to the other processes described herein.

Amplification can be performed on circular templates, such as with rolling circle or strand displacement amplification. Amplification can be performed in emulsions, such that each droplet of the emulsion contains, on average, one or fewer template molecules. Amplification can be performed in beads trapped by a weir with, on average, one or fewer template molecules per bead, preferably less than one in seven or less. Other methods of nucleic acid amplification that can be used include quantitative PCR, fluorescent PCR, multiplex PCR, real time PCR, single cell PCR, restriction fragment length polymorphism PCR, hot start PCR, nested PCR, in situ polony PCR, bridge PCR, picotiter PCR, ligase chain reaction, transcription amplification, self-sustained sequence replication, consensus-sequence primed PCR, arbitrarily primer PCR, degenerate oligonucleotide-primed PCR, and combinations thereof. Amplification may also include multiple steps of amplification, such as with pre-amplification steps.

Sequencing

The invention provides methods for performing sequencing on a target nucleic acid. The sequencing can be performed using real-time sequencing, sequencing by synthesis, sequencing by proton detection, pyrosequencing, superpyro sequencing, sequencing by ligation, Sanger sequencing, or any next generation sequencing technique, next generation sequencing technique, or future generations of sequencing. The sequencing can be performed by a sequencing module. The sequencing process can be automated similar to the other automated processes described herein.

Some methods of sequencing that are compatible with the invention as described herein can be found in, for example, U.S. Patent publications 2009/0092970, 2010/0129810, and 2010/0197507, and in U.S. Pat. Nos. 7,943,305; 7,575,865; 7,232,656; and 6,833,246. Typically, a sequencing reaction as used in this invention includes a target molecule, at least one primer, and a polymerase. Nucleotides used for sequencing, such as for sequencing by synthesis can vary. In some embodiments, nucleotides may be unmodified. In some embodiments, nucleotides may contain an optically detectable label, such as a fluorescent dye. The label can be, for example, attached to the gamma phosphate, the beta phosphate, to the base, to the 2' carbon of the ribose, or to the 3' end of the nucleotide. The label can also include a quenching molecule, which can be similarly attached to the nucleotide. The label or quencher can be attached to the nucleotide by a selectively cleavable bond, such as by a photocleavable or chemically cleavable bond. In some embodiments, sequencing uses oligonucleotides, such as during sequencing by ligation. Oligonucleotides for use in sequencing by ligation can be less than about five base pairs, less than about 8 base pairs, less than about 10 base pairs, or less than about 20 base pairs. Oligonucleotides for use in sequencing may also be labeled as described for nucleotides.

In some embodiments, sequencing can be performed on molecules individually immobilized to the bottom of a zero mode waveguide, allowing selective detection of fluorescently labeled nucleotides present in the active site of the sequencing polymerase. Nucleotides that are incorporated into the elongating strand can be detected and distinguished from nucleotides only transiently present in the active site. After incorporation, the fluorescent label can be removed or destroyed prior to incorporation of the next nucleotide.

In some embodiments, the labeled nucleotide contains a FRET pair comprising a fluorophore and a quencher. Upon incorporation of the nucleotide into the elongating strand, the fluorophore is unquenched. The unquenched fluorophore can then be detected to determine the target sequence. In some embodiments, the labeled nucleotide contains a chemiluminescent label. Upon incorporation of the nucleotide into the elongating strand, the label is unquenched and through a chain of reactions or directly light is release and detected to determine the target sequence. In one embodiment, the change in pH by the sequencing reaction is measured electronically. In one embodiment, the strand of DNA is moved through a nanopore or nanostructure and the sequence detected.

In some embodiments, sequencing can be performed in wells containing picoliter volumes. Populations of molecules amplified from a single molecule of a sequencing library can be segregated within individual wells with a polymerizing enzyme. Nucleotides can be sequentially flowed across arrays of wells. Upon incorporation of a nucleotide, pyrophosphate is released. The released pyrophosphate can then be detected enzymatically, such as using a luciferase based assay. In one embodiment, the sequencing reaction includes ATP sulfurylase, luciferase, apyrase, and the substrates luciferin and adenosine 5' phosphosulfate. Pyrophosphates released by nucleotide incorporation can be converted to ATP by sulfurylase, and the ATP can then be used to produce oxyluciferin, which can be detected as visible light.

In some embodiments, sequencing can be performed in the amplification module. As one example, after bridge PCR amplification, sequencing can be directly performed on the immobilized, amplified molecules. In one embodiment, the amplified molecules comprise two complementary strands immobilized on the surface of a flow cell. One of the complementary strands can be removed from the flowcell by selectively cleaving one of the two primers used for amplification and washing the cleaved strand out of the flow cell. The remaining strand can then be sequenced by any of the methods described herein, such as sequencing by synthesis with fluorescent detection. In one embodiment, microfluidic valves and pumps control the flow of reagent to the flowcell. In one embodiment, the library construction or nucleic acid occurs in the flow cell.

In some embodiments, sequencing can be performed by binding beads from the amplification step to a solid surface, such as a slide. Sequencing of the immobilized amplified molecules can be performed by sequencing by the ligation, such as by using sets of short, fluorescently labeled oligonucleotide probes to detect specific dinucleotide base pairs. Upon ligation of a labeled probe, a portion of the probe, including the fluorescent label can be cleaved off, and a new set of oligonucleotide probes used to detect another portion of the target sequence. Multiple rounds of detection using different initiating primers can be used to detect different subsets of the target sequence.

[In some embodiments, ion semiconductor sequencing can be used. Changes in electrical charges or proton concentrations resulting from nucleotide incorporation can be detected, for example by using CMOS chips. In one embodiment, individual molecules are separated into different nanowells, and a single type of nucleotide added into the wells. Without being bound by any particular theory, upon incorporation of one or more of the nucleotide, hydrogen ions are released and can be detected. Multiple incorporations can result in a higher signal. The nanowells can be sequentially exposed to the different nucleotides, which allows detection of the target sequence. The nanowells can be formed in valves with detection either through the activation layer or the fluidic layer or through an end of a layer.

In some embodiments, the amplified nucleic acids are sequentially cleaved, such as with an exonuclease. The cleaved nucleotides can be detected, for example by mass spectrometry, or by detecting fluorescent labels unique to each type of nucleotide. In some embodiments, the amplified nucleic acid may be passed through a nanopore, and the sequence of the target nucleic acid detected by detecting changes in an electric current or other measurements as the nucleic acid is passed across the nanopore.

Automation

The invention provides for automated methods for analyzing a sample. The automated method can be an automated sequencing method. In some embodiments, a first instruction is provided to a first module for preparing a sample for sequencing. The first instructions can include instructions for one or more of the following steps: lysing cells, isolating nucleic acids, fragmenting the isolated nucleic acids, adding adapters to the fragmented nucleic acids to create a library of nucleic acid templates, and amplifying the library of nucleic acid templates. The first module can include a sample processing module, a library construction module, and an amplification module. A second instruction can then be provided to the first module and/or a second module to transfer the fragmented nucleic acids to a second module. A third instruction can be provided to the second module for performing a sequencing reaction.

In some embodiments, an automated step or method can be performed without user intervention, or without the use of a hand-operated pipette. In some embodiments, an automated step or method can be performed by a robot.

Kits

The invention provides for kits for performing an automated sequencing reaction. The kit can include one or more of the following components: a cartridge, a microfluidic chip, and reagents. The cartridge can have one or more reaction chambers that can hold a macrofluidic volume. A macrofluidic volume can be a volume of liquid that is about or greater than about 10, 50, 100, 500, 1000, 1500, or 2000 microliters. A microfluidic chip can be a device with one or more channels with micron or sub-micron sized dimensions. The microfluidic chip can also have one or more pneumatically actuated valves. The reagents can include one or more of any reagent described herein, for example, adapters, polymerases, primers, magnetic beads, enzymes, chemicals, and buffers. In some embodiments, separate kits may be provided for sample processing modules and for a sequencing module.

EXAMPLES

Example 1

Sample Processing

Cell lysis of 1 mL samples can be carried out using heat treatment at 95° C. for 5 min; the heat is provided by resistive heating through metal blocks with thermocouple feedback. Paramagnetic bead-based purification can be used to purify and concentrate the DNA from the lysates. Optimization can include enhanced focusing of magnetic fields to localize and concentrate magnetic forces. Fluid and bead handling can be controlled to minimize losses and maximize low level sample detection. DNA can be sheared and optimized to produce a narrow distribution of DNA between, for example, 500 and 800 bp. The device can be designed to recover and shear DNA from as low as 10 organisms per mL.

Example 2

Nucleic Acid Fragmentation

Genomic DNA was repeatedly pumped under high pressure (500 psi) by syringes 3 and 6 between wells 2 and 5 through shearing region 4 of the device shown in FIG. 6. The channel was 50 microns deep and 100 microns wide.

Figure 7:
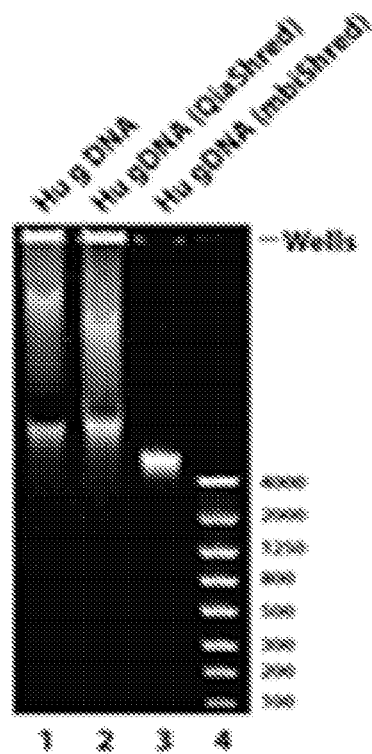
FIG. 7 shows an image of an agarose gel showing results from DNA shearing.

FIG. 7 shows the results of the nucleic acid fragmentation on an agarose gel. The gel is a 1.2% agarose gel. Lane 4 contains DNA markers. Lane 1 shows human genomic DNA. Lane 2 shows human genomic DNA sheared using QiaShred. Lane 3 shows human genomic DNA sheared using the device depicted in FIG. 6. Most unsheared human genomic DNA (lanes 1 and 2) remained caught in the electrophoresis gel wells. Some entered the gel during electrophoresis, resulting in the smear and a band running at about 10 kb. Sheared DNA (lane 3) ran in a tight band at approximately 5 kb. DNA was cycled 20 times between well 1 and well 2.

Example 3

Library Construction

Processing times to perform the reactions can be minimized by enhancing the full volume chemistry with optimal enzyme concentrations, minimizing reaction volumes (consistent with system performance), and maximizing the size of diaphragm (pneumatically actuated) pumps to decrease times for mixing and pumping. Modifications facilitating full system integration can be designed and integrated into the module.

Example 4

Emulsion Rolling Circle Amplification

The emRCA module can be designed to mix the circularized DNA, capture beads and silicon oil in a volume capable of generating the number of beads needed for adequate DNA sequencing throughput, which can be about 2 million. The emRCA Module can create, incubate, disrupt the emulsion, and provide washed beads with immobilized amplified nucleic acid for DNA sequencing.

An incubation device, including a disposable cartridge, and an emulsion generator/cleanup device can be integrated. A custom interface can be designed and built to deliver both fluids and electrical power to the device.

Example 5

Bridge Amplification

The amplification module can be designed to perform bridge amplification in the flowcell. The DNA is added to the flowcell and attaches to the primers attached to the flowcell surface. Primers, polymerase, master mix is added to the flow cell and PCR or other amplification performed to create sufficient DNA for adequate DNA sequencing. The amplification module can adjust the temperate for thermal cycling and isothermal reactions.

An incubation device, including a disposable cartridge, can be integrated. A custom interface can be designed and built to deliver both fluids and electrical power to the device.

Example 6

Sequencing

The sequencing module can be built with a 2 MP CMOS image sensor capable of interrogating 500,000 wells. This can correspond to 250 Mbases per run with 500 bp reads per well. The system can be modular with each CMOS sensor representing a single core. In this way, multiple 250 Mbase "cores" can be ganged together in a single system utilizing the same fluidics system. This can allow for significant throughput increases fairly seamlessly without incurring significant penalties in terms of increased system bulkiness.

Fluidics that can allow for the aforementioned "impulse" reagent delivery can be integrated into this system. All sequence data generated by the advanced sequencing module, which can be a super pyro sequencing module, can be analyzed and evaluated using standardized methods. Further refinements on the error model of sequencing data can be carried out. The sequencing module can produce data (using a modified Viterbi algorithm-based base caller) that has >99% single raw read accuracy at 500 base pairs.

Example 7

Integration

The upstream modules, the Sample Processing Module and the Library Construction Module, can be combined into a Unified Sample Preparation Module (USPM). The emRCA and SuperPyroSequencing Modules can also be combined. The USPM and the emRCA and sequencing modules can be integrated together.

The Sample Processing Module and the Library Construction Module can be combined into a single Unified Sample Preparation Module that uses a single sample preparation cartridge. The combined Unified Sample Preparation Module can unify the common components of each module, i.e. solenoids, I/O boards, temperature controllers, into a single module that fully integrates the functions of the separate microchips of each module into a single cartridge. The DevLink software integration can control both modules using a unified script.

The single-use cartridge can contain microchips with diaphragm valves that direct fluids, on-board reagents, and the combined functionality of the Sample Processing Module and the Library Construction Module, i.e. lysis, bead-based DNA purification, fragmentation, circularization, and isolation of single-stranded circular templates.

For the integrated system breadboard, the cartridge can be fabricated by machining plastics or rapid prototyping using stereolithography/3D printing (e.g. SLA) combined with microchips having pneumatically actuated valves. The cartridge can minimize losses that occur onto surfaces and can perform as many processes as possible in a common reaction. Lengths of interconnection channels can be minimized. The devices can also be manufactured using high volume manufacturing technologies, such as injection molding.

The amplified product on beads can be transferred from the amplification module to the sequencing module using a peristaltic pump in the sequencing Module or by microfluidic pumps. The pump can pull the prepared beads from the amplification module and distribute them into the picotiter wells for analysis.

The software integration can 'wrap' the amplification and sequencing modules with DevLink software using 'handles' that allow each one to manipulated with command line interfaces. DevLink software can be a single interface to operate all modules by sequentially evoking scripts that operate the individual modules from a single GUI. The software can wrap the sequencing program analysis software to produce FASTA files or other formats. The software can wrap internal databases or interfaces to external databases.

The integration can combine amplification/sequencing modules with the Unified Sample Preparation Module. The fluidic connection can be tubing from the Unified Sample Preparation Module to the amplification/sequencing module. The unified upstream module can deliver circularized templates or linear templates with adapters in approximately 1 mL volume to the amplification module using pressure-assisted diaphragm pumps on the Unified Sample Preparation Module.

The integrated system can be used to sequence single organisms at different titers in buffer at the success rates, read lengths, and detection limits discussed herein. This single organism can include organisms with lambda DNA or other bacteriophages, and bacteria. The system can be used to sequence mixtures of bacteria. Sequence data can be BLASTed.

Example 8

Using a Linear Array to Perform Next Generation Sequencing Library Preparation

This example describes a method of performing NGS library preparation from DNA fragments using a module containing a linear array.

An example of a device containing a linear array can be used to prepare an adaptor-linked DNA library from a sample of DNA fragments. FIG. 17 shows the architecture of such a fluidic device. The device is organized as an array of non-branching, linear valve arrays. Each valve array comprises valves P1, P2, P3, P4, and P5, labeled as 2021, 2022, 2023, 2024, and 2025, respectively. The device shown here has three valve arrays operated in parallel. Each valve array comprises an isolation valve 2030 on one side of a first terminal valve and another isolation valve 2035 on one side of a second terminal valve. The isolation valves control fluidic access to the valve array. Also, each valve array is fluidically connected through the isolation valves to reagent rails 2080 and 2090, configured to provide liquids through ports in the device to the valve array, respectively.

Creation of an adaptor library from DNA fragments includes three enzymatic steps: (1) end repair (e.g. rendering the ends of the DNA fragments blunt and 5' phosphorylated), (2) A-tailing the end-repaired fragments, and (3) adaptor ligation to the A-tailed fragments. DNA purification can be performed after each enzymatic step. Non-microfluidic volumes can be loaded into non-microfluidic compartments unless otherwise noted. Loading can be performed by a fluidics robot. Typically, when a fluid is to be added into the array, the system is first primed with the liquid by pumping from a source reservoir through the channels to a designated waste port. For simplicity, these steps are not mentioned in the list of steps below. Note that each enzymatic step (and any associated DNA purification) is carried out in a similar fashion, with the biggest differences being the location of the master mix reservoir and the location of the starting material for the step. For example, in the first enzymatic step, the Sample reservoir is the location of the starting material. Tri subsequent steps, the starting material is located in one of the valve chambers of the array. The description below describes a single cycle of reaction mixing, incubation, and DNA purification. Cascading three such cycles, with the small changes noted above for subsequent cycles, can accomplish NGS library preparation.

The steps described below are one example of a sequence of actions to perform a single cycle of reaction mixing, incubation, and DNA purification. Other sequences to perform the same method will be apparent to one skilled in the art.

Reaction Mixing, Incubation, and SPRI DNA Purification

Sample comprising DNA fragment is loaded into sample reservoirs 2040, SPRI beads are loaded in reservoir 2084, end repair master mix is loaded in reservoir 2094, A-tailing master mix is loaded into reservoir 2092, ligation master mix is loaded into reservoir 2096, wash solution is loaded in reservoir 2086, and elution solution (e.g., TE) is loaded in reservoir 2088. The default system state is where all valves are closed. The protocol then proceeds as follows:

1. Transfer and isolate an aliquot (a valve chamber volume) of Sample in P1 by (i) opening sample valves 2041, (ii) opening P1, and (iii) closing sample valves 2041.
2. Transfer Sample into valve chamber P2 by simultaneously closing P1 and opening P2.
3. Transfer and isolate an aliquot of end-repair master mix to P1 by (i) opening rail valve 2095, opening isolation valves 2030, (iii) opening P1, (iv) closing rail valve 2095, and (v) closing isolation valves 2030.
4. Mix Sample and end-repair master mix aliquots by repeatedly cycling them across the valve array in ping-pong fashion as follows: Ping=(i) close P1/open P3, (ii) close P2/open P4, (iii) close P3/open P5; Pong=(i) close P5/open P3, (ii) close P4/open P2, (iii) close P3/open P1.
5. Incubate reaction. Ping-pong mixing may optionally be continued throughout the reaction incubation period (1-30 minutes at room temperature).
6. Load and isolate SPRI Bead Mix in P4 and P5 by (i) opening rail valve 2085, opening isolation valves 2035, (iii) opening P5, (iv) opening P4, (v) closing isolation valves 2035, and (vi) closing rail valve 2085.
7. Transfer SPRI bead mix to P3 and P4 by simultaneously closing P5 and opening P3.

8. Mix completed reaction with SPRI bead mix by repeatedly cycling across the valve array in ping-pong fashion as follows: Ping=close P1/open P5; Pong=close p5/open P1.
9. Open P5 by (i) opening a rail valve connected to an empty rail reservoir (e.g. reservoir 2088), (ii) opening the corresponding isolation valve(s) (e.g. valves 2035), and (iii) opening P5.
10. Capture the beads (and bound DNA) in P5 by generating a magnetic field gradient at P5, and pumping the contents of P1-P4 through P5 to a designated (rail) waste reservoir.
11. Isolate an aliquot of wash solution in P1 by: (i) opening rail valve 2087, (ii) open isolation valves 2035, (iii) open P1, (iv) close rail valve 2087, (v) close isolation valves 2030.
12. Transfer wash solution to P4 by: (i) close P1/open P2, (ii) close P2/open P3, (iii) close P3/open P4.
13. Transfer wash solution to P5 (washing beads) by: (i) opening isolation valves 2035, (ii) opening rail valve 2083, (iii) close P4.
14. Repeat steps 11-13 until wash solution is exhausted, and then pump air by repeating steps 11-13 until beads are dry.
15. Introduce elution buffer into P5 by: (i) closing P5, (ii) opening rail valve 2089, (iii) opening isolation valves 2035, (iv) opening P5.
16. Remove the magnetic field gradient from P5, and mix beads and elution buffer by transferring eluate and beads to P4 by: close P5/open P4.
17. Recapture beads in P5 by: (i) restoring magnetic field gradient to P5, (ii) close P4/open P5. Separate eluate (containing DNA) from beads by transferring eluate to P4 by: close P5/open P4.
18. Resuspend beads in P5 by: (i) removing the magnetic field gradient from P5, (ii) introducing elution buffer into P5 (as in step 15 above).
19. Transfer resuspended beads to a designated waste reservoir by: (i) opening isolation valves 2035, (ii) opening rail valve 2083, (iii) closing P5. Repeat steps 18-19 until P5 is clear of beads.
20. Transfer eluate (containing DNA) to P2 by: (i) close P4/open P3, (ii) close P3/open P2.

After the final purification step of the last enzymatic cycle (e.g. ligating to adapter molecules), a second bead-based purification step can optionally be performed to select ligated DNA of a target length range.

Example 9

Using Biotinylated Nucleotides to Label Sequencing Libraries

Short RNA can be mixed with reverse transcriptase, dNTPs, and suitable buffers to perform a reverse transcription reaction. The dCTP used in the reaction contains a biotin label (bdCTP). After reverse transcription, the product contains the short RNA bound to a cDNA strand labeled with biotin at each location where the cDNA contains a cytosine. The double-stranded nucleic acid is denatured, and the labeled cDNA is purified from the rest of the reagents by binding to streptavidin-labeled beads. Subsequently, unlabeled dNTPs are added with a DNA polymerase and suitable buffers for second strand DNA synthesis, resulting in a double-stranded DNA molecule, where one strand contains bdCTP. The double-stranded molecule can then be end-repaired, A-tailed, and otherwise modified in preparation for ligation to an unlabeled adapter nucleic acid. Additional purification steps between these modification steps can further remove any contaminating free bdCTP from the reaction mixture. Ligation can then be performed using a ligase and ATP. Streptavidin beads can then be used to selective bind the labeled nucleic acids, allowing the unligated adapters to be washed away. In some cases, trace amounts of unligated target molecules may also bind to the beads. However, because they do not contain the adapter sequence that contains the primer-binding sequence, they will generally not have a significant effect on the sequencing reaction. The steps described can be performed in a linear array as described in Example 7, or can be performed in any other microfluidic library preparation module as described herein.

Example 10

Reaction Cleanup by Removing Enzymes

During sequencing library preparation, instead of purifying the nucleic acid sample from a reaction mixture after each reaction step, reaction cleanup can be performed. Reaction cleanup can be performed in a module of an integrated sample-to-sequence system, such as a library preparation module or an amplification module as described herein. To perform reaction cleanup, reactions can be performed where some or all of the enzymes used during the preparation steps can be labeled with an affinity tag such as a hexa-Histidine tag (His6). For example, during end-repair, an affinity tagged DNA polymerase such as His-tagged T4 DNA polymerase and an affinity tagged kinase such as His-tagged T4 polynucleotide kinase (PNK) can be added to the reaction along with all the substrates and reagents necessary for end-repair. After end-repair, beads that bind His6, such as magnetic Ni-NTA beads, can be added to the reaction to bind the labeled enzymes. The beads, bound to the enzymes, can then be removed using magnetic force, leaving a reaction mixture that contains the product and other substrates, but is substantially depleted of the enzymes. The resulting depleted mixture can be concentrated or directly used in the next library preparation step. For example, A-tailing can then be performed using His6-tagged Klenow fragment and dATP, and the tagged Klenow fragment similarly removed by binding to Ni-NTA beads, and the depleted mixture optionally concentrated. Ligase and adapter molecules can then be added to A-tailed nucleic acid mixture. The final sequencing library product can then be purified from the reaction mixture by SPRI or other suitable methods. The sequencing library product can then be used for amplification or sequencing, such as by transferring the library from a library preparation module to an amplification or sequencing module. Reaction cleanup can also optionally be performed in an amplification module to remove the polymerases used in amplification prior to sequencing. In another embodiment, the enzymes are immobilized on the bead, particle, or nanoparticle and can be added or removed from the reactions by manipulating the bead, particle, or nanoparticle.

Example 11

Using an Integrated Sample-to-Sequence System

An integrated sequence-to-sample system can be used to sequence bacteria at a sample concentration of 10 cells per 1 mL sample. Gram positive and gram negative model organisms for testing can be *Staphylococcus epidermidis* and *Escherichia coli*, respectively. Organisms are grown and harvested in log phase, then aliquoted in appropriate media at a set of dilutions for quantitation. Cell samples are then diluted to an appropriate concentration for testing.

FIG. 19 depicts a schematic for the steps performed by one embodiment of the ISS of this invention. 1 mL samples of the model organisms are input into sample processing module via a sample port. The user can start automated sample processing and sequencing through a user interface that interacts with the programmable control module. Optionally, the user can select a specific protocol or input information regarding the samples through the interface. Additional input from the user is not required for the system to obtain sequence information from the input samples.

The sample processing module can lyse the cells of the input sample, for example by using a lysis submodule, such as a bead beater. Lysis protocols can be adjusted or selected for optimal release of genomic DNA while minimizing degradation. Nucleic acids, such as DNA or RNA, can then be purified from the lysed sample, such as by using non-sequence specific SPRI beads, or the surface of channels or capillaries. In some embodiments, sequence-specific purification protocols may be used, such as hybridization to oligonucleotides on beads, nanoparticles or surfaces. Purification or other steps can be performed in a linear array. Optionally, whole genome amplification can be performed on the purified nucleic acids, which is particularly useful for low sample concentrations.

The fragmented nucleic acids can be transferred to a library preparation module, which can contain a linear array. The nucleic acids can be fragmented, such as by shearing into smaller fragments. For example, the nucleic acid fragments can be about 25 base pairs in length or 300 base pairs in length or other lengths as programmed. The library preparation module can perform an automated sequence of reactions in a microfluidic device, for example at room temperature. The library preparation module can mix the nucleic acid fragments with a polymerase and a polynucleotide kinase (PNK), such as biotin-labeled T4 polymerase and biotin-labeled T4 (PNK) to perform end repair on the fragmented nucleic acids. After end repair, the labeled enzymes can be removed from the reaction mixture, for example by binding to streptavidin-labeled magnetic beads. The end-repaired nucleic acids can then be A-tailed by mixing with dATP and a polymerase, such as Taq polymerase. The dATP can be labeled, such as with a biotin derivative so that A-tailing incorporates biotin into the target nucleic acid. The labeled, A-tailed target nucleic acid can then be purified, such as by SPRI to remove the biotin-labeled nucleotides and Taq polymerase. Next, the library preparation module can mix the sample with a ligase, such as a T4 ligase and an adapter oligonucleotide containing a T overhang to ligate with the A-tailed sample. The ligated target nucleic acid can then be purified from the unlabeled adapter nucleotide and T4 ligase, such as by binding to streptavidin-labeled beads, removing the remainder of the reaction mixture, and eluting the nucleic acids from the sample to form a sequencing library. Size selection of the sequencing library can be performed, such as by using SPRI.

Next, the sequencing library can optionally be transferred to a normalization module. The normalization module can quantify the nucleic acid concentration of the sequencing library, for example by taking an aliquot of the sequencing library, mixing with a dye that fluoresces upon binding to DNA, and detecting with a fluorimeter. The normalization module can then dilute or concentrate the remaining sequencing library sample to an appropriate concentration for amplification and sequencing. In some embodiments, the normalization module can combine multiple sequencing library samples.

The normalized sequencing library can then be transferred to an amplification or sequencing module. In some cases, the amplification and sequencing modules can be combined within a single module. For example, the module can be a commercially available sequencer, such as an Illumina MiSeq sequencer. Individual molecules of the sequencing library can be immobilized in a reaction chamber, such as on different spots on the surface of a flow cell of the sequencing module. The module can perform bridge amplification on the immobilized molecules to form dense regions on the surface of the flow cell comprising multiple copies of both strands of the target nucleic acid. The module can then remove one of the two strands from the surface of the flow cell. The module can use a polymerase and reversibly terminated, fluorescently labeled nucleotides to perform sequencing by synthesis on the strand remaining on the surface of the flow cell. The resulting sequence information can then be optionally analyzed by the computing module and displayed on the user interface, saved to memory, or output to another device.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein can be employed in practicing the invention. It is intended that the following claims define the scope of the invention and that methods and structures within the scope of these claims and their equivalents be covered thereby.

What is claimed is:

1. A device comprising:
one or more modules, wherein each of said one or more modules comprises:
(a) one or more valve arrays, each comprising a series of valves connected through fluidic connections, each of said series of valves comprising, in order, a first terminal valve, at least three intermediate valves and a second terminal valve;
(b) a plurality of first ports, each fluidically connected through a separate control valve to a common rail, said common rail fluidically connected to each of the first terminal valves of said valve arrays; and
(c) a plurality of second ports, each fluidically connected through a separate control valve to a common rail, said common rail fluidically connected to each of the second terminal valves of said valve arrays,
wherein each of said first terminal valves, said second terminal valves and said intermediate valves of said valve arrays comprises a valve with a valve chamber.

2. The device of claim 1 wherein the fluidic connections are unbranched.

3. The device of claim 1, wherein each of said valve arrays further comprises a movable magnet that is adjacent to a given valve in said series of valves.

4. The device of claim 1, wherein each of said modules further comprises at least one port that is fluidically connected through a separate control valve to each of said first terminal valves.

5. The device of claim 4, wherein said at least one port is fluidically connected to a temperature-controlled channel.

6. The device of claim 4, wherein each of said modules further comprises at least one additional port that is fluidically connected through a separate control valve to each of said second terminal valves.

7. The device of claim 1, wherein said one or more valve arrays is a plurality of valve arrays.

8. The device of claim 1, wherein said one or more modules is a plurality of modules in fluidic connection with each other.

9. The device of claim 8, further comprising at least one additional common rail, wherein said plurality of modules is in fluidic connection with each other through said at least one additional common rail.

10. The device of claim 9, wherein said at least one additional common rail comprises a plurality of additional common rails, and wherein said plurality of modules is in fluidic connection with each other through said plurality of additional common rails.

11. The device of claim 10, wherein each of said first terminal valves is in fluidic connection with a first subset of said plurality of additional common rails.

12. The device of claim 10, wherein each of said second terminal valves is in fluidic connection with a second subset of said plurality of additional common rails.

13. The device of claim 8, wherein each of said plurality of modules comprises a plurality of valve arrays.

14. The device of claim 1, further comprising an actuating module configured to actuate said valve arrays.

* * * * *